(12) United States Patent  
Braje et al.

(10) Patent No.: US 8,314,120 B2
(45) Date of Patent: Nov. 20, 2012

(54) SMALL MOLECULE POTENTIATORS OF METABOTROPIC GLUTAMATE RECEPTORS

(75) Inventors: Wilfried Braje, Ludwigshafen (DE); Katja Jantos, Ludwigshafen (DE); Hervé Geneste, Ludwigshafen (DE); Mario Mezler, Ludwigshafen (DE); Margaretha Henrica Maria Bakker, Ludwigshafen (DE)

(73) Assignee: Abbott GmbH & Co. KG, Wiesbaden (DE)

( * ) Notice: Subject to any disclaimer, the term of this patent is extended or adjusted under 35 U.S.C. 154(b) by 0 days.

(21) Appl. No.: 13/073,087

(22) Filed: Mar. 28, 2011

(65) Prior Publication Data

US 2011/0245247 A1 Oct. 6, 2011

Related U.S. Application Data

(60) Provisional application No. 61/319,065, filed on Mar. 30, 2010.

(51) Int. Cl.
*A61K 31/4375* (2006.01)
*A61K 31/4725* (2006.01)
*A61K 31/403* (2006.01)
*C07D 471/04* (2006.01)
*C07D 217/22* (2006.01)
*C07D 487/04* (2006.01)
*C07D 209/46* (2006.01)

(52) U.S. Cl. ........ 514/299; 514/414; 546/123; 546/141; 548/453; 548/465; 548/472

(58) Field of Classification Search .................. 514/299, 514/412; 548/453, 472; 546/123, 141
See application file for complete search history.

(56) References Cited

U.S. PATENT DOCUMENTS

2009/0270418 A1* 10/2009 Sloss et al. ............... 514/255.05
2009/0275578 A1  11/2009 Clayton et al.

FOREIGN PATENT DOCUMENTS

| WO | 2006/015158 | 2/2006 |
|---|---|---|
| WO | 2006/020879 | 2/2006 |
| WO | 2006/030032 | 3/2006 |
| WO | 2006/047237 | 5/2006 |
| WO | 2006/057860 | 6/2006 |
| WO | 2006/057869 | 6/2006 |
| WO | 2006/057870 | 6/2006 |
| WO | 2006/091496 | 8/2006 |
| WO | 2007/021308 | 2/2007 |
| WO | 2007/021309 | 2/2007 |
| WO | 2008145616 | 12/2008 |

OTHER PUBLICATIONS

Fraley, Positive allosteric modulators of the metabotropic glutamate receptor 2 for the treatment of schizophrenia, 2009, Expert Opin. Ther. Patents, vol. 19(9), p. 1259-1275.*

Bayrakdarian, STN Record of WO 2008/136756, CA Plus DN 149:5556642, entry date: Nov. 13, 2008; Cited compounds, entry date: Dec. 9, 2008.*

Bonnefous et al., Biphenyl-indanones: Allosteric potentiators of the metabotropic glutamate subtype 2 receptor, Bioorganic & Medicinal Chemistry Letters, 15, 2005, 4354-4358.

Cube et al., 3-(2-Ethoxy-4-{4-[3-hydroxy-2-methyl-4-(3-methylbutanoyl)-phenoxy]butoxy}phenyl)propanoic acid: a brain penetrant allosteric potentiator at the metabotropic glutamate receptor 2 (mGluR2), Bioorganic & Medicinal Chemistry Letters, 15, 2005, 2389-2393.

Govek et al., Benzazoles as allosteric potentiators of metabotropic glutamate receptor 2 (mGluR2): Efficacy in an animal model for schizophrenia., Bioorganic & Medicinal Chemistry Letters, 15, 2005, 4068-4072.

(Continued)

*Primary Examiner* — Golam M M Shameem
*Assistant Examiner* — Karen Cheng
(74) *Attorney, Agent, or Firm* — Lisa V. Mueller; Michael Best & Friedrich LLP

(57) ABSTRACT

The present invention relates to small molecule potentiators of metabotropic receptors, in particular of the mGlu2 receptor. The present invention also relates to the use of these compounds for the prevention or treatment of neurological and psychiatric disorders associated with glutamate dysfunction and diseases in which metabotropic glutamate receptors are involved. The present invention thus provides compounds of formula I

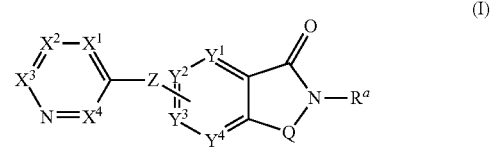

(I)

wherein $X^1$ is N or $C-R^1$, $X^2$ is N or $C-R^2$, $X^3$ is N or $C-R^3$, $X^4$ is N or $C-R^4$ provided that none or one of $X^1$, $X^2$, $X^3$ or $X^4$ is N; $Y^1$ is N, C or $C-R^5$, $Y^2$ is N, C or $C-R^6$, $Y^3$ is $Y^1$, $Y^2$, N, C or $C-R^7$, $Y^4$ is N, C or $C-R^8$ provided that only the moiety $Y^1$, $Y^2$, $Y^3$ or $Y^4$ to which Z is bound is C and further provided at most one of $Y^1$, $Y^2$, $Y^3$ or $Y^4$ is N; Z is O, S, S(O), $S(O)_2$ or $NR^Z$; Q is $CH_2$ or $CH_2CH_2$, where one or two of the hydrogen atoms in $CH_2$ or $CH_2CH_2$ may be replaced by halogen, $C_1$-$C_4$-alkyl or $C_1$-$C_4$-haloalkyl; $R^1$ is inter alia hydrogen, halogen, $C_1$-$C_6$-alkyl, $C_1$-$C_6$-haloalkyl, $C_1$-$C_6$-alkoxy, $C_1$-$C_4$-haloalkoxy, $C_3$-$C_8$-cycloalkyl, a radical $NR^{1a}R^{1b}$, C-bound 3- to 7-membered, saturated heterocyclyl having 1 or 2 nitrogen atoms and 0 or 1 heteroatoms, selected from O and S, as ring members, aryl, aryl-$CH_2$, aryloxy, hetaryl, hetaryloxy or hetaryl-$CH_2$, wherein the heterocyclyl, aryl and hetaryl rings ring in the last six radicals themselves are unsubstituted or carry 1, 2, 3, 4 or 5 identical or different radicals $R^{1c}$; $R^2$ has one of the meanings given for $R^1$; $R^3$ and $R^4$ are, inter alia, selected from hydrogen, halogen, $C_1$-$C_4$-alkyl, $C_1$-$C_4$-haloalkyl, $C_3$-$C_6$-cycloalkyl, $C_1$-$C_4$-alkoxy, $C_1$-$C_4$-alkoxy-$C_1$-$C_4$-alkyl, phenyl, $C_1$-$C_4$-haloalkoxy, a radical $(CH_2)_n NR'R''$; $R^5$, $R^6$, $R^7$, $R^8$ are, independently of each other, selected from hydrogen, halogen, etc.; $R^a$ is $C_3$-$C_6$-cycloalkyl, $C_1$-$C_6$-haloalkyl or $C_1$-$C_6$-alkyl, which is unsubstituted or carries one radical selected from $C_1$-$C_4$-alkoxy, $C_1$-$C_4$-haloalkoxy and a radical $NR^{a1}R^{a2}$; and the N-oxides and the pharmaceutically acceptable salts thereof.

32 Claims, No Drawings

OTHER PUBLICATIONS

Hu et al., Pyrimidine methyl anilines: selective potentiators for the metabotropic glutamate 2 receptor., Bigoorganic & Medicinal Chemistry Letters, 14, 2004, 5071-5074.

Pinkerton et al., Allosteric potentiators of the metabotropic glutamate receptor 2 (mGlu2). Part 1: Identification and synthesis of phenyl-tetrazolyl acetophenones., Biooorganic & Medicinal Chemistry Letters, 14, 2004, 5329-5332.

Pinkerton et al., Allosteric potentiators of the metabotropic glutamate receptor 2 (mGlu2). Part 2: 4-Thiopyridyl acetophenones as non-tetrazole containing mGlu2 receptor potentiators., Biooorganic & Medicinal Chemistry Letters, 14, 2004, 5867-5872.

Pinkerton et al., Allosteric potentiators of the metabotropic glutamate receptor 2 (mGlu2). Part 3: Identification and biological activity of indanone containing mGlu2 receptor potentiators., Biooorganic & Medicinal Chemistry Letters, 15, 2005, 1565-1571.

Pinkerton et al., Phenyl-tetrazolyl Acetophenones: Discovery of Positive Allosteric Potentiatiors for the Metaboreopic Glumate 2 Receptor, J. Med. Chem., 2004, 47, 4595-4599.

Conn and Pin, Annu. Rev. Pharmacol. Toxicol. 37, 205-37, 1997).

Prezeau et al., Mol. Pharmacol. 49, 422-429, 1996.

Soloviev et al., Biochimica et Biophysica Acta 1446, 161-166, 1999.

Pin and Duvoisin, Neuropharmacol. 34, 1-26, 1995.

Nakanishi et al., Brain Res. Rev. 26, 230-235, 1998).

Fagni et al., TINS 23 (2), 80-88, 2000.

Shigemoto et al., J. Neurosci. 17,7503-7522,1997.

Cartmell & Schoepp, J. Neurochem. 75(3), 889-907, 2000.

Monn et al., J. Med. Chern. 39(15), 2990-3000, 1996.

Trombley and Westbrook, J. Neurosci. 12(6), 2043-50, 1992.

Barda, et al., Bioorganic and Medicinal Chemistry Letters, 14, 3099, 3102, 2004.

Brauner-Osborne et al., J. Med. Chem. 43 (14),2609-2645, 2000.

Monn et al., J. Med. Chem. 40(4), 528-37, 1997.

Monn et al., J. Med. Chem. J. Med. Chern. 42(6), 1027-40, 1999.

Nakazato et al., J. Med. Chem. 43(25), 4893-909, 2000.

Kingston et al., Neuropharmacology 37(1), 1-12, 1998.

Johnson et al., Neuropharmacology 38(10),1519-29, 1999.

Johnson et al., J. Med. Chem. 46(15), 3189-92, 2003.

Schaffhauser et al., Mol. Pharmacol. 64(4), 798-810, 2003.

Galici et al., JPET 315(3), 1181-1187, 2005.

Johnson et al. Psychopharmacol, 179(1), 271-83, 2005.

Higgins et al., Neuropharmaco. 146, 907-917, 2004.

Moghaddam and Adams, Science 281(5381), 1349, 1998.

\* cited by examiner

SMALL MOLECULE POTENTIATORS OF METABOTROPIC GLUTAMATE RECEPTORS

CROSS-REFERENCE TO RELATED APPLICATION

This is the non-provisional of U.S. Provisional Patent Application No. 61/319,065, filed on Mar. 30, 2010, the contents of which are hereby incorporated by reference.

The present invention relates to small molecule potentiators of metabotropic receptors, in particular of the mGlu2 receptor. The present invention also relates to the use of these compounds for the prevention or treatment of neurological and psychiatric disorders associated with glutamate dysfunction and diseases in which metabotropic glutamate receptors are involved.

BACKGROUND OF THE INVENTION

Glutamate, the major excitatory neurotransmitter in the brain, elicits its effects by activating ligand-gated cation channels, termed ionotropic glutamate receptors (iGluRs), as well as metabotropic glutamate receptors (mGlu receptors). The latter belong to the G-Protein coupled receptor (GPCR) family 3 (Conn and Pin, Annu. Rev. Pharmacol. Toxicol. 37, 205-37, 1997) and are coupled through heterotrimeric G-proteins to intracellular effector systems. These receptor types exert multiple modulatory effects within the central nervous system (CNS). Eight mGlu receptor subtypes have been cloned from mammalian brain to date. Depending on their G-protein coupling profile, pharmacology and sequence identity, these receptors are classified into three groups (Conn and Pin, Annu. Rev. Pharmacol. Toxicol. 37, 205-37, 1997). Group I mGlu receptors primarily couple through Gq to increases in phosphoinositide hydrolysis and the cellular $Ca^{2+}$-system via phospholipase C (PLC), and include the mGlu1 receptor and mGlu5 receptor. Group II mGlu receptors, which include mGlu2 and mGlu3, inhibit adenylylcyclase (AC), just as group III mGlu receptors, which comprise mGlu4, mGlu6, mGlu7 and mGlu8. Thereby, in groups II and III, the pertussis-toxin sensitive G-protein Gi is involved in signal transduction. However, group II and group III mGlu receptors differ in their sequence identity and pharmacological profile.

Of the 8 mGlu receptor subtypes various splice variants exist. Within group I mGlu receptors the splicing variability is most pronounced. MGlu 1 exists in 6 different splicing forms. The receptors mGlu1a/a, 1b/b, 1c, 1d and 1f all differ in their C-terminal, intracellular domain (Prezeau et al., Mol. Pharmacol. 49, 422-429, 1996; Soloviev et al., Biochimica et Biophysica Acta 1446, 161-166, 1999), and mGlu1e is truncated N-terminally, lacking most of the protein coding region (Pin and Duvoisin, Neuropharmacol. 34, 1-26, 1995). So far of mGlu5 (group I), and the group III receptors mGlu4, mGlu7 and mGlu8 two splicing variants have been demonstrated. mGlu6, which is located solely in ON-bipolar cells of the retina (Nakanishi et al., Brain Res. Rev. 26, 230-235, 1998), only has one isoform. The same holds for mGlu2 and mGlu3 receptors (Fagni et al., TINS 23 (2), 80-88, 2000).

The synaptic localization of group I mGlu receptors and group II/III mGlu receptors differs. While group I receptors are located predominantly postsynaptically, group III mGlu receptors rather show a presynaptic localization (Shigemoto et al., J. Neurosci. 17, 7503-7522, 1997; Cartmell & Schoepp, J. Neurochem. 75(3), 889-907, 2000). Group II receptors seem to be located pre- and postsynaptically, depending on brain region and synapse-type. A perisynaptic localization of mGlu2 has also been demonstrated. In this case the receptor might only be activated under high frequency stimulation, then preventing further transmitter release and thus reducing pathologically high levels of glutamate within the synaptic cleft. Autoreceptor function (medial perforant path, mossy fiber-CA3, spinal cord synapse, corticostriatal synapse) and heteroreceptor functions have been demonstrated for group II mGlu receptors at synapses in diverse brain regions. The pre- and perisynaptic localization of group II mGlu receptors, combined with their auto- and heteroreceptor function and their coupling to inhibitory intracellular signalling cascades implies an important role of this receptor type for the regulation of excitatory neurotransmission.

The first compounds which discriminated between the 3 different groups of mGlu receptors were low affinity agonists: 3,5-dihydroxyphenylglycine (3,4-DHPG), which selectively stimulates the group 1 mGlu receptors; (2R,4R)-4-aminopyrrolidine-carboxylic acid (2R,4R-APDC) activating group II mGlu receptors (Monn et al., J. Med. Chem. 39(15), 2990-3000, 1996) and L-Amino-4-phosphonobutyrate (L-AP4, Trombley and Westbrook, J. Neurosci. 12(6), 2043-50, 1992) for the activation of group III mGlu receptors. All these compounds have been valuable tools for the investigation of the various functions of mGlu receptors by in vitro studies, but none of these compounds has been shown to exert potent central effects after systemic administration. Other early compounds, which have mainly been used for in vitro studies, turned out to activate ionotropic glutamate receptors as well. For the widely used group II mGlu receptor agonist (2S,1′R, 2′R,3′R)-2-(2′,3′-dicarboxypropyl)glycine also activates NMDA receptors.

For studying the in vivo effects and therapeutic applications of group II agonists, the breakthrough came from the discovery of LY354740 and LY379268 (Formulae given e.g. in D. A. Barda et al., Bioorganic and Medicinal Chemistry Letters, 14, 3099-3102, 2004). These two compounds are highly specific group II receptor agonists with only very low affinity to other mGlu receptors or ionotropic glutamate receptors. They have $EC_{50}$ values of 10 and 20 nM (LY354740) and 3 and 5 nM (LY379268), for mGlu2 and 3 respectively. While a differentiation between the two group II receptors is not possible, a specificity of >1:30.000 towards group I receptors and between 1:100 (mGlu6) to >1:30.000 (mGlu7) to group III receptors offers a high discrimination potential to these receptor types (Cartmell and Schoepp, J. Neurochem. 75(3), 889-907, 2000; Brauner-Osborne et al., J. Med. Chem. 43 (14), 2609-2645, 2000). Both compounds were designed as conformationally constrained analogues of glutamate (Monn et al., J. Med. Chem. 40(4), 528-37, 1997; J. Med. Chem. 42(6), 1027-40, 1999), and represent competitive agonists at the glutamate binding site. Furthermore these two compounds are systemically active.

Derivatives of these compounds, MGS 0008 and MGS 0028 (Nakazato et al., J. Med. Chem. 43(25), 4893-909, 2000) and have a higher oral availability. They also show increased antagonistic effects on PCP-induced head-weaving and hyperactivity in rats. Recently also a highly selective antagonist for group II mGlu receptors has been identified (Kingston et al., Neuropharmacology 37(1), 1-12, 1998; Johnson et al., Neuropharmacology 38(10), 1519-29, 1999). No appreciable specific binding of the radio-ligand [3H]-LY341495 (formula given in D. A. Barda et al. 2004) was found in membranes of cells expressing human mGlu1a, mGlu5a, mGlu4a, mGlu6, or mGlu1a receptors. Many effects induced by group II receptor agonists could be reversed by this compound. Thus LY341495 also represents a highly selective tool compound.

Positive modulators activate the mGlu2 receptor dependent on the presence of glutamate (potentiators). Thus, the compound "sensitizes" the receptor to react already at lower concentrations of the ligand. Positive modulators can also activate the mGlu2 receptor directly. The mGlu receptors consist of a large extracellular N-terminal domain, which binds the natural ligand, glutamate, which is homologous to the periplasmatic amino acid binding proteins from bacteria. This domain is linked to a 7-transmembrane domain. This canonical domain, common to all G-protein coupled receptors, contains the canonical ligand binding site for GPCRs (compare rhodopsin in retinal). In the mGluRs this site is free and may play a role as modulatory site for positive and negative allosteric compounds.

A hint for the exact amino acid sites responsible for ligand binding of a model potentiator (LY487379, see Johnson et al., J. Med. Chem. 46(15), 3189-92, 2003) come from the amino acid comparison between mGlu2 receptor and mGluR3 in this region. As the potentiator is specific for mGlu2 receptor, the binding should not take place at mGluR3 and the responsible amino acids should be exactly the ones which differ between the two receptors. Recently the binding site of a model potentiator (LY487379) has been mapped by site directed mutagenesis. The binding site seems to be within the transmembrane domain of mGlu2 receptor (Schaffhauser et al., Mol. Pharmacol. 64(4), 798-810, 2003). In particular the amino acids 688, 689 and 735 are indicated for binding.

MGlu2 receptor is expressed in both separate and overlapping circuits of relevance for neuropsychiatric and neurological disorders. This includes expression in neocortex, thalamus, striatum, amygdala and hippocampus. Within these circuits mGlu2 receptor is mainly expressed presynaptically. As a consequence of this expression pattern it has been shown that excitatory transmitter release is regulated by group II agonists in diverse brain regions. For, it has been demonstrated that group II agonists normalize PCP-induced increase of glutamate in the prefrontal cortex (PFC) and that dopamine is regulated by group II agonists in a region-specific manner. As one function group II agonists increase dopamine and metabolites in the PFC. Also serotonin and metabolites are regulated in the PFC. This has further been demonstrated by a functional antagonism of 5-HT2A receptors in this brain region.

These data indicate that the mGlu2 receptor approach may normalize a number of de-regulated transmitters in schizophrenia. The mGlu2 receptor agonist/potentiator concept will likely give rise to the opportunity to normalize
  positive symptoms, due to regulation of glutamate,
  negative symptoms, due to regulation of dopamine and serotonin, and
  cognitive symptoms, due to regulation of acetylcholine in the PFC.
Besides schizophrenia, drug abuse may be an interesting disease indication, as group II agonists block of expression of locomotor sensitization by amphetamine, among a multitude of other described effects. The usefulness of such compounds is not limited to the disease states described above.

The potentiator concept for mGlu2 receptor is relatively new (Barda et al., 2004), but necessary to evaluate the relevance of mGlu2 receptor versus mGluR3. This is of note, as the group II agonists described above do cross react with both receptor types. Within the recent year, reports directly demonstrate the relevance of mGlu2 receptor in psychosis models in rodents by describing function of mGlu2 receptor potentiators in models of PCP-induced hyperlocomotion, amphetamine-induced hyperlocomotion, and reversal of amphetamine-induced disruption of PPI in mice (Galici et al., JPET 315(3), 1181-1187, 2005).

Beyond these data, indicating a relevance of mGlu2 receptor potentiators in schizophrenia, new reports furthermore demonstrate efficacy of mGlu2 receptor potentiators in anxiety, as potentiators have been shown to be efficacious in rat fear-potentiated startle and stress-induced hyperthermia in mice (Johnson et al. Psychopharmacol., 179(1), 271-83, 2005).

A pure NMDA activation approach (the "glutamatergic hypothesis of schizophrenia") may result in side effect liabilities. In particular, excitotoxicity is a relevant side effect which needs to be considered early within a potential screening cascade of such projects. This side effect liability may limit the usefulness of such approaches.

As described above, the mGlu2 receptor positive modulator approach does not purely rely on the glutamatergic hypothesis, but likely is involved in the normalization of release of a number of excitatory neurotransmitters. Consequently, to date there is no evidence for excitotoxic liability of group II agonists or mGlu2 receptor positive modulators. Group II agonists even show the opposite effects. They are neuroprotective in the MPTP model of Parkinson's disease, they reduce low $Mg^{2+}$-induced epileptiform discharges in slice preparations and they have anticonvulsant action in acute seizure models.

As a relevant side effect, a negative influence on cognition was described for group II agonists (Higgins et al., Neuropharmacol. 46, 907-917, 2004). However, to date this finding is controversial in the literature. While one group finds a reversal of cognitive deficits induced by PCP (Moghaddam and Adams, Science 281(5381), 1349-52, 1998), a second group finds a reduction of DNMTP performance with the mGlu2 receptor agonist LY354740, which is not present in mGlu2 receptor knockout mice (Higgins et al., Neuropharmacol. 46, 907-917, 2004). This finding contrasts to the data from Moghaddam and Adams and would also contradict the normalization of ACh release in the PFC by this compound (see above).

WO 2006/015158 and WO 2006/047237 describe heterocyclic compounds carrying an indanone moiety, the compounds being potentiators of metabotropic glutamate receptors, including the mGlu2 receptor.

WO 2006/030032 describes pyridinone compounds which are potentiators of metabotropic glutamate receptors, including the mGlu2 receptor.

WO 2006/049969 describes N-(phenyl)aminoalkyl substituted pyrimidine compounds, which are potentiators of metabotropic glutamate receptors, including the mGlu2 receptor.

WO 2006/057860, WO 2006/057869 and WO 2006/057870 describe compounds carrying a 4-acyl-3-hydroxyphenyl moiety. The compounds are suggested to be potentiators of metabotropic glutamate receptors, including the mGlu2 receptor.

WO 2006/091496 describes compounds carrying a benzazole moiety, the compounds being suggested as potentiators of metabotropic glutamate receptors, including the mGlu2 receptor.

WO 2006/020879, WO2007/021308 and WO 2007/021309 disclose isoindolone compounds, which are suggested as potentiators of metabotropic glutamate receptors, including the mGlu2 receptor.

WO 2008/145616 discloses heterocyclic compounds which are positive modulators of metabotropic receptors, including the mGlu2 receptor.

Although the compounds of prior art have a high affinity with regard to the mGlu2 receptor, their receptor binding profile and/or their pharmacological profile is not always satisfactory. In particular, the compounds often have poor selectivity with regard to mGlu2 receptor in comparison with mGlu3 or group III mGlu receptors or are glutamate agonists. Moreover the potentiators are in terms of (i) binding affinity, (ii) receptor potentiation and/or stimulation profile, (iii) selectivity versus other receptors, (iv) physicochemical properties, (v) in vitro microsomal stability and (vi) pharmacokinetic parameters not satisfactory.

It is an object of the present invention to provide further compounds which are potentiators of metabotropic glutamate receptors, in particular of the mGlu2 receptor, and which thus are useful in the treatment or prevention of neurological and psychiatric disorders associated with glutamate dysfunction and diseases in which metabotropic glutamate receptors are involved. In particular, such diseases are central nervous system disorders selected from the group of schizophrenia, drug abuse, anxiety, migraine, depression and epilepsy and the like.

These and further objects are solved by the compounds of the general formula I, as described herein, as well as by the tautomers thereof, and by their pharmaceutically acceptable salts.

SUMMARY OF THE INVENTION

The present invention thus provides compounds of formula I

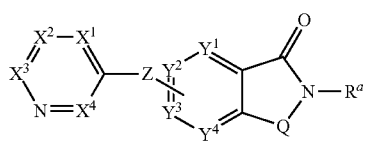

(I)

wherein
$X^1$ is N or C—$R^1$
$X^2$ is N or C—$R^2$
$X^3$ is N or C—$R^3$
$X^4$ is N or C—$R^4$
provided that none or one of $X^1$, $X^2$, $X^3$ or $X^4$ is N;
$Y^1$ is N, C or C—$R^5$
$Y^2$ is N, C or C—$R^6$
$Y^3$ is N, C or C—$R^7$
$Y^4$ is N, C or C—$R^8$
provided that only the moiety $Y^1$, $Y^2$, $Y^3$ or $Y^4$ to which Z is bound is C and $Y^2$, further provided that 0, 1 or 2, preferably at most one of $Y^1$, $Y^2$, $Y^3$ or $Y^4$ is N;
Z is a covalent bond, $CR^{Za}R^{Zb}$, O, S, S(O), S(O)$_2$ or $NR^{Zc}$;
$R^{Za}$, $R^{Zb}$ are independently of each other selected from hydrogen, halogen and $C_1$-$C_4$-alkyl;
$R^{Zc}$ is hydrogen, $C_1$-$C_4$-haloalkyl, $C_3$-$C_6$-cycloalkyl, $C_3$-$C_6$-cycloalkylmethyl, $C_1$-$C_4$-alkyl, which is unsubstituted or carries one radical selected from $C_1$-$C_4$-alkoxy and $NR^{Z1}R^{Z2}$;
where $R^{Z1}$ and $R^{Z2}$ are independently of each other selected from hydrogen, $C_3$-$C_6$-cycloalkyl, $C_3$-$C_6$-cycloalkylmethyl, $C_1$-$C_4$-alkyl and $C_1$-$C_4$-alkoxy-$C_1$-$C_4$-alkyl, or
$R^{Z1}$ and $R^{Z2}$ together with the nitrogen to which they are attached form a 5- or 6-membered N-bound saturated heterocycle, which, in addition to the nitrogen atom may comprise a further heteroatom, selected from O, S and N, as ring member and which is unsubstituted or carries 1, 2, 3 or 4 $C_1$-$C_4$-alkyl radicals;
or $R^{Zc}$ is a radical S(O)$_2$$R^{Z3}$ or a radical S(O)$_2$$NR^{Z4}R^{Z5}$, where $R^{Z3}$ is $C_1$-$C_4$-alkyl, $C_1$-$C_4$-alkoxy-$C_1$-$C_4$-alkyl, $C_1$-$C_4$-haloalkyl, $C_3$-$C_6$-cycloalkyl, $C_3$-$C_6$-cycloalkylmethyl, phenyl or benzyl, wherein the phenyl ring in the last two mentioned radicals itself is unsubstituted or carries 1, 2, 3, 4 or 5 identical or different radicals selected from halogen, $C_1$-$C_4$-alkyl, $C_1$-$C_4$-haloalkyl, $C_1$-$C_4$-alkoxy and $C_1$-$C_4$-haloalkoxy,
$R^{Z4}$ and $R^{Z5}$ have one of the meanings given for $R^{Z3}$ or $R^{Z4}$ and $R^{Z5}$ together with the nitrogen to which they are attached form a 5- or 6-membered N-bound saturated heterocycle, which, in addition to the nitrogen atom may comprise a further heteroatom, selected from O, S and N as ring member and which is unsubstituted or carries 1, 2, 3 or 4 $C_1$-$C_4$-alkyl radicals;
Q is CH$_2$ or CH$_2$CH$_2$, where one or two of the hydrogen atoms in CH$_2$ or CH$_2$CH$_2$ may be replaced by halogen, $C_1$-$C_4$-alkyl or $C_1$-$C_4$-haloalkyl;
$R^1$ is selected from hydrogen, halogen, $C_1$-$C_6$-alkyl, which is unsubstituted or carries one $C_1$-$C_4$-alkoxy radical, $C_1$-$C_6$-haloalkyl, $C_1$-$C_6$-alkoxy, $C_1$-$C_4$-haloalkoxy, $C_3$-$C_8$-cycloalkyl, a radical $NR^{1a}R^{1b}$, a radical $CH_2NR^{1a}R^{1b}$, C-bound 3- to 10-membered, saturated heterocyclyl having 1 or 2 nitrogen atoms and 0 or 1 heteroatoms, selected from O and S, as ring members, aryl, aryl-CH$_2$, aryloxy, hetaryl, hetaryloxy or hetaryl-CH$_2$, wherein the aryl, heterocyclyl and hetaryl rings ring in the last seven radicals themselves are unsubstituted or carry 1, 2, 3, 4 or 5 identical or different radicals $R^{1c}$;
$R^{1a}$ is hydrogen, $C_1$-$C_8$-alkyl, $C_1$-$C_8$-haloalkyl, $C_1$-$C_4$-alkoxy-$C_1$-$C_4$-alkyl, $C_3$-$C_8$-cycloalkyl, $C_1$-$C_8$-alkylcarbonyl, $C_1$-$C_8$-alkoxycarbonyl, benzyl, phenyl or 5- or 6-membered hetaryl, wherein the phenyl and hetaryl rings in the last three radicals itself are unsubstituted or carry 1, 2, 3, 4 or 5 identical or different radicals $R^{1c}$;
$R^{1b}$ is hydrogen or $C_1$-$C_4$-alkyl; or
$NR^{1a}R^{1b}$ is a 5- to 10-membered mono- or bicyclic N-bound saturated heterocycle, which, in addition to the nitrogen atom may comprise a further heteroatom, selected from O, S and N as ring member and which is unsubstituted or carries 1, 2, 3 or 4 $C_1$-$C_4$-alkyl radicals;
$R^{1c}$ is selected from the group consisting of halogen, CN, OH, $C_1$-$C_4$-alkyl, $C_3$-$C_6$-cycloalkyl, $C_1$-$C_4$-haloalkyl, $C_1$-$C_4$-alkoxy and $C_1$-$C_4$-haloalkoxy;
$R^2$ has one of the meanings given for $R^1$ provided that $R^2$ is different from hydrogen, if $X^1$ is N or CH, further provided that $R^1$ is different from hydrogen, if $X^2$ is N;
$R^3$ and $R^4$ are independently of each other, selected from hydrogen, halogen, $C_1$-$C_4$-alkyl, $C_1$-$C_4$-haloalkyl, $C_3$-$C_6$-cycloalkyl, $C_1$-$C_4$-alkoxy, $C_1$-$C_4$-alkoxy-$C_1$-$C_4$-alkyl, phenyl, $C_1$-$C_4$-haloalkoxy, a radical (CH$_2$)$_n$NR'R", where R' and R" have one of the meanings given for $R^{Z1}$ and $R^{Z2}$ and wherein n is 0, 1, 2, 3 or 4, or C-bound 3- to 7-membered, saturated heterocyclyl having 1 or 2 nitrogen atoms and 0 or 1 heteroatoms, selected from O and S, as ring members, where the heterocyclyl itself is unsubstituted or carries 1, 2, 3, 4 or 5 identical or different radicals $R^{6c}$, where $R^{6c}$ has one of the meanings given for $R^{1c}$;

$R^2$ and $R^3$ can form together with the carbon atoms, to which they are bound, a fused 5- to 6-membered ring, which is itself unsubstituted or carries 1, 2, 3 or 4 identical or different radicals $R^{23a}$;

$R^{23a}$ is selected from the group consisting of halogen, CN, OH, $C_1$-$C_4$-alkyl, $C_3$-$C_6$-cycloalkyl, $C_1$-$C_4$-haloalkyl, $C_1$-$C_4$-alkoxy and $C_1$-$C_4$-haloalkoxy;

$R^5$ is hydrogen, halogen, CN, $C_1$-$C_4$-alkyl, $C_1$-$C_4$-haloalkyl, $C_1$-$C_4$-alkoxy, $C_1$-$C_4$-alkoxy-$C_1$-$C_4$-alkyl, $C_1$-$C_4$-haloalkoxy, $(CH_2)_n NR'R''$, where R' and R'' have one of the meanings given for $R^{Z1}$ and $R^{Z2}$ and wherein n is 0, 1, 2, 3 or 4,
or C-bound 3- to 7-membered, saturated heterocyclyl having 1 or 2 nitrogen atoms and 0 or 1 heteroatoms, selected from O and S, as ring members, where the heterocyclyl itself is unsubstituted or carries 1, 2, 3, 4 or 5 identical or different radicals $R^{5c}$, where $R^{5c}$ has one of the meanings given for $R^{1c}$;

$R^6$, $R^7$, $R^8$ are, independently of each other, selected from hydrogen, halogen, CN, $C_1$-$C_4$-alkyl, $C_1$-$C_4$-haloalkyl, $C_1$-$C_4$-alkoxy, $C_1$-$C_4$-haloalkyoxy, $C_1$-$C_4$-alkoxy-$C_1$-$C_4$-alkyl, $(CH_2)_n NR'R''$, where R' and R'' have one of the meanings given for $R^{Z1}$ and $R^{Z2}$ and wherein n is 0, 1, 2, 3 or 4, or C-bound 3- to 7-membered, saturated heterocyclyl having 1 or 2 nitrogen atoms and 0 or 1 heteroatoms, selected from O and S, as ring members, where the heterocyclyl itself is unsubstituted or carries 1, 2, 3, 4 or 5 identical or different radicals $R^{6c}$, where $R^{6c}$ has one of the meanings given for $R^{1c}$;

$R^a$ is $C_3$-$C_6$-cycloalkyl, $C_1$-$C_6$-haloalkyl or $C_1$-$C_6$-alkyl, which is unsubstituted or carries one radical selected from $C_1$-$C_4$-alkoxy, $C_1$-$C_4$-haloalkoxy and a radical $NR^{a1}R^{a2}$,
where $R^{a1}$ and $R^{a2}$ are independently of each other selected from hydrogen, $C_1$-$C_4$-alkyl, $C_3$-$C_6$-cycloalkyl, $C_3$-$C_6$-cycloalkylmethyl and $C_1$-$C_4$-alkoxy-$C_1$-$C_4$-alkyl,
a radical $NR^{a3}R^{a4}$ or a radical $N=C(R^{a5})R^{a6}$, where $R^{a3}$ and $R^{a5}$ are independently of each other selected from hydrogen, $C_1$-$C_4$-alkyl, $C_1$-$C_4$-haloalkyl, $C_3$-$C_6$-cycloalkyl, $C_3$-$C_6$-cycloalkylmethyl and $C_1$-$C_4$-alkoxy-$C_1$-$C_4$-alkyl;
$R^{a4}$ and $R^{a6}$ are independently of each other selected from hydrogen, $C_1$-$C_4$-alkyl, $C_1$-$C_4$-haloalkyl, $C_3$-$C_6$-cycloalkyl, $C_3$-$C_6$-cycloalkylmethyl, $C_1$-$C_4$-alkoxy-$C_1$-$C_4$-alkyl, C-bound 3- to 7-membered, saturated heterocyclyl, 3- to 7-membered, saturated heterocyclylmethyl, where heterocyclyl in the last two mentioned radicals has 1 or 2 nitrogen atoms and 0 or 1 heteroatoms, selected from O and S, as ring members,
aryl, aryl-$CH_2$, hetaryl and hetaryl-$CH_2$, wherein the heterocycicyl, aryl and hetaryl rings ring in the last six radicals themselves are unsubstituted or carry 1, 2, 3, 4 or 5 identical or different radicals $R^{ac}$ where $R^{ac}$ has one of the meanings given for $R^{1c}$;

and the pharmaceutically acceptable salts and the N-oxides thereof.

The compounds of the present invention are potentiators of metabotropic glutamate (mGlu) receptor function, in particular they are potentiators of mGlu2 receptors. That is, the compounds of the present invention do not appear to bind at the glutamate recognition site on the mGlu receptor, but in the presence of glutamate or a glutamate agonist, the compounds of the present invention increase mGlu receptor response. The present potentiators are expected to have their effect at mGlu receptors by virtue of their ability to increase the response of such receptors to glutamate or glutamate agonists, enhancing the function of the receptors. It is recognized that the compounds of the present invention would be expected to increase the effectiveness of glutamate and glutamate agonists of the mGlu2 receptor. Thus, the compounds of the present invention are expected to be useful in the treatment of various neurological and psychiatric disorders associated with glutamate dysfunction described to be treated herein and others that can be treated by such positive modulators as are appreciated by those skilled in the art.

The present invention also relates to pharmaceutical compositions comprising at least one compound of the formula I, an N-oxide thereof and/or a pharmaceutically acceptable salt thereof, optionally together with at least one physiologically acceptable carrier or auxiliary substance.

The present invention also relates to a method for treating a medical disorder, selected from neurological and psychiatric disorders associated with glutamate dysfunction, said method comprising administering an effective amount of at least one compound of the formula I, an N-oxide thereof and/or a pharmaceutically acceptable salt thereof to a subject in need thereof.

The present invention also relates to a method for potentiation of metabotropic glutamate receptor activity in a mammal which comprises administering an effective amount of at least one compound of the formula I, an N-oxide thereof and/or a pharmaceutically acceptable salt thereof.

The present invention also relates to the use of the compounds of formula I, an N-oxide thereof and/or a pharmaceutically acceptable salt thereof, in therapy of a disease mentioned herein.

The compounds of the formula I, their N-oxides and their pharmaceutically acceptable salts are particularly useful for preparing
a medicament for treating, controlling, ameliorating or reducing the risk of anxiety in a mammalian;
a medicament for preparing a medicament for treating, controlling, ameliorating or reducing the risk of depression in a mammalian; a medicament for treating, controlling, ameliorating or reducing the risk of migraine in a mammalian;
a medicament for treating, controlling, ameliorating or reducing the risk of schizophrenia in a mammalian;
a medicament for treating, controlling, ameliorating or reducing the risk of epilepsy in a mammalian;
a medicament for treating or ameliorating the symptoms associated with substance-related disorders in a mammalian.

The present invention also relates to
a method for treating, controlling, ameliorating or reducing the risk of anxiety in a mammalian;
a method for treating, controlling, ameliorating or reducing the risk of depression in a mammalian;
a method for treating, controlling, ameliorating or reducing the risk of schizophrenia in a mammalian;
a method for treating, controlling, ameliorating or reducing the risk of epilepsy in a mammalian;
a method for treating, controlling, ameliorating or reducing the risk of migraine in a mammalian;
a method for treating or ameliorating the symptoms associated with substance-related disorders in a mammalian;
which methods comprising administering an effective amount of at least one compound of the formula I, an N-oxide thereof and/or a pharmaceutically acceptable salt thereof to a mammal in need thereof.

DETAILED DESCRIPTION OF THE INVENTION

The compounds of the present invention may contain one or more asymmetric centers and can thus occur as racemates and racemic mixtures, single enantiomers, diastereomeric mixtures and individual diastereomers. Additional asymmetric centers may be present depending upon the nature of the various substituents on the molecule. Each such asymmetric center will independently produce two optical isomers and it is intended that all of the possible optical isomers and diastereomers in mixtures and as pure or partially purified compounds are included within the ambit of this invention. The present invention is meant to comprehend all such isomeric forms of these compounds. The independent syntheses of these diastereomers or their chromatographic separations may be achieved as known in the art by appropriate modification of the methodology disclosed herein. Their absolute stereochemistry may be determined by the x-ray crystallography of crystalline products or crystalline intermediates which are derivatized, if necessary, with a reagent containing an asymmetric center of known absolute configuration.

If desired, racemic mixtures of the compounds may be separated, so that the individual enantiomers are isolated. The separation can be carried out by methods well known in the art, such as the conversion of the enantiomeric mixture of compounds I into a diastereomeric mixture, e.g. by reaction with a chiral auxiliary, such as a chiral acid or base, followed by separation of the individual diastereomers by standard methods, such as fractional crystallization or chromatography. The enantiomeric mixture of the compounds can also be separated directly by chromatographic methods utilizing chiral stationary phases, which methods are well known in the art. Alternatively, any enantiomer of a compound may be obtained by stereoselective synthesis using optically pure starting materials or reagents of known configuration by methods well known in the art.

The term "pharmaceutically acceptable salts" refers to cationic or anionic salts compounds, wherein the counter ion is derived from pharmaceutically acceptable non-toxic bases or acids including inorganic or organic bases and inorganic or organic acids.

When the compound of formula I is acidic, salts may be prepared from pharmaceutically acceptable non-toxic bases, including inorganic and organic bases. Salts derived from inorganic bases include salts, wherein the counter ion is aluminium, ammonium, calcium, copper, ferric, ferrous, lithium, magnesium, manganic, manganous, potassium, sodium, zinc ion and the like. Particularly preferred are the ammonium, calcium, magnesium, potassium, and sodium ions. Salts derived from pharmaceutically acceptable organic non-toxic bases include salts of primary, secondary, and tertiary amines, substituted amines including naturally occurring substituted amines, cyclic amines, and basic ion exchange resins, such as arginine, betaine, caffeine, choline, dibenzylethylene-diamine, diethylamine, 2-diethylaminoethanol, 2-dimethylaminoethanol, ethanolamine, ethylenediamine, N-ethyl-morpholine, N-ethylpiperidine, glucamine, glucosamine, histidine, hydrabamine, isopropylamine, lysine, methylglucamine, morpholine, piperazine, piperidine, polyamine resins, procaine, purines, theobromine, triethylamine, trimethylamine, tripropylamine, tromethamine, and the like.

When the compound of the present invention is basic, salts may be prepared from pharmaceutically acceptable non-toxic acids, including inorganic and organic acids. Such acids include acetic, trifluoroacetic acid, benzenesulfonic, benzoic, camphorsulfonic, citric, ethanesulfonic, fumaric, gluconic, glutamic, hydrobromic, hydrochloric, isethionic, lactic, maleic, malic, mandelic, methanesulfonic, mucic, nitric, pamoic, pantothenic, phosphoric, succinic, sulfuric, tartaric, p-toluenesulfonic acid, and the like. Particularly preferred are citric, hydrobromic, hydrochloric, maleic, phosphoric, sulfuric, fumaric, and tartaric acids. It will be understood that, as used herein, references to the compounds of formula I are meant to also include the pharmaceutically acceptable salts.

The present invention moreover relates to compounds of formula I as defined above, wherein at least one of the atoms has been replaced by its stable, non-radioactive isotope (e.g., hydrogen by deuterium, $^{12}C$ by $^{13}C$, $^{14}N$ by $^{15}N$, $^{16}O$ by $^{18}O$) and preferably wherein at least one hydrogen atom has been replaced by a deuterium atom.

Of course, the compounds according to the invention contain more of the respective isotope than this naturally occurs and thus is anyway present in the compounds I.

The compounds of the formula I and their salts in the solid form may exist in more than one crystal structure (polymorphism), and may also be in the form of hydrates or other solvates. The present invention includes any polymorph of the compound I or its salt as well as any hydrate or other solvate.

The organic moieties mentioned in the above definitions of the variables are—like the term halogen—collective terms for individual listings of the individual group members. The prefix $C_n$-$C_m$ indicates in each case the possible number of carbon atoms in the group.

The term "halogen" denotes in each case fluorine, bromine, chlorine or iodine, in particular fluorine, chlorine or bromine.

The term "alkyl" as used herein and in the alkyl moieties of alkoxyalkyl, alkylamino, dialkylamino and alkylsulfonyl denotes in each case a straight-chain or branched alkyl group having usually from 1 to 8 carbon atoms, frequently from 1 to 6 carbon atoms, preferably 1 to 4 carbon atoms, in particular 1 to 2 carbon atoms. Examples of an alkyl group are methyl, ethyl, n-propyl, iso-propyl, n-butyl, 2-butyl, iso-butyl, tert-butyl, n-pentyl, 1-methylbutyl, 2-methylbutyl, 3-methylbutyl, 2,2-dimethylpropyl, 1-ethylpropyl, n-hexyl, 1,1-dimethylpropyl, 1,2-dimethylpropyl, 1-methylpentyl, 2-methylpentyl, 3-methylpentyl, 4-methylpentyl, 1,1-dimethylbutyl, 1,2-dimethylbutyl, 1,3-dimethylbutyl, 2,2-dimethylbutyl, 2,3-dimethylbutyl, 3,3-dimethylbutyl, 1-ethylbutyl, 2-ethylbutyl, 1,1,2-trimethylpropyl, 1,2,2-trimethylpropyl, 1-ethyl-1-methylpropyl, 1-ethyl-2-methylpropyl, n-heptyl, 1-methylhexyl, 2-methylhexyl, 3-methylhexyl, 4-methylhexyl, 5-methylhexyl, 1-ethylpentyl, 2-ethylpentyl, 3-ethylpentyl, 1-propylpentyl, n-octyl, 1-methyloctyl, 2-methylheptyl, 1-ethylhexyl, 2-ethylhexyl, 1,2-dimethylhexyl, 1-propylpentyl and 2-propylpentyl.

The term "haloalkyl" as used herein and in the haloalkyl moieties of haloalkylsulfonyl, denotes in each case a straight-chain or branched alkyl group having usually from 1 to 8 carbon atoms, frequently from 1 to 6 carbon atoms, preferably 1 to 4 carbon atoms, in particular 1 to 2 carbon atoms, wherein the hydrogen atoms of this group are partially or totally replaced with halogen atoms. Preferred haloalkyl moieties are selected from $C_1$-$C_4$-haloalkyl, more preferably from $C_1$-$C_2$-haloalkyl, in particular from $C_1$-$C_2$-fluoroalkyl, such as fluoromethyl, difluoromethyl, trifluoromethyl, 1-fluoroethyl, 2-fluoroethyl, 2,2-difluoroethyl, 2,2,2-trifluoroethyl, pentafluoroethyl or $C_1$-$C_4$-fluoroalkyl, such as fluoromethyl, difluoromethyl, trifluoromethyl, 1-fluoroethyl, 2-fluoroethyl, 2,2-difluoroethyl, 2,2,2-trifluoroethyl, pentafluoroethyl, 2-fluoro-1-methylethyl, 2,2-difluoro-1-methylethyl, 2,2,2-trifluoro-1-methylethyl, 2,2,2-trifluoro-1-trifluormethylethyl, 3,3,3-trifluoropropyl, 4,4,4-trifluorobutyl and the like.

The term "alkoxy" as used herein denotes in each case a straight-chain or branched alkyl group which is bound via an oxygen atom and has usually from 1 to 8 carbon atoms, frequently from 1 to 6 carbon atoms, preferably 1 to 4 carbon atoms. Examples of an alkoxy group are methoxy, ethoxy, n-propoxy, iso-propoxy, n-butyloxy, 2-butyloxy, iso-butyloxy, tert-butyloxy, pentyloxy, 1-methylbutyloxy, 2-methylbutyloxy, 3-methylbutyloxy, 2,2-dimethylpropyloxy, 1-ethylpropyloxy, hexyloxy, 1,1-dimethylpropyloxy, 1,2-dimethylpropyloxy, 1-methylpentyloyx, 2-methylpentyloxy, 3-methylpentyloxy, 4-methylpentyloxy, 1,1-dimethylbutyloyx, 1,2-dimethylbutyloxy, 1,3-dimethylbutyloxy, 2,2-dimethylbutyloxy, 2,3-dimethyl-butyloyx, 3,3-dimethylbutyloxy, 1-ethylbutyloxy, 2-ethylbutyloxy, 1,1,2-trimethylpropyloxy, 1,2,2-trimethylpropyloxy, 1-ethyl-1-methylpropyloxy, 1-ethyl-2-methylpropyloxy n-heptyloxy, 1-methylhexyloxy, 2-methylhexyloxy, 3-methylhexyloxy, 4-methylhexyloxy, 5-methylhexyloxy, 1-ethylpentyloxy, 2-ethylpentyloxy, 3-ethylpentyloxy, 1-propylpentyloxy, n-octyloxy, 1-methyloctyloxy, 2-methylheptyloxy, 1-ethylhexyloxy, 2-ethylhexyloxy, 1,2-dimethylhexyloxy, 1-propylpentoxy and 2-propylpentyloxy.

The term "haloalkoxy" as used herein denotes in each case a straight-chain or branched alkoxy group having from 1 to 8 carbon atoms, frequently from 1 to 6 carbon atoms, preferably 1 to 4 carbon atoms, in particular 1 or 2 carbon atoms, wherein the hydrogen atoms of this group are partially or totally replaced with halogen atoms, in particular fluorine atoms. Preferred haloalkoxy moieties include $C_1$-$C_4$-haloalkoxy, in particular $C_1$-$C_2$-fluoroalkoxy, such as fluoromethoxy, difluoromethoxy, trifluoromethoxy, 1-fluoroethoxy, 2-fluoroethoyx, 2,2-difluoroethoyx, 2,2,2-trifluoroethoxy, 2-chloro-2-fluoroethoxy, 2-chloro-2,2-difluoroethoxy, 2,2-dichloro-2-fluorethoxy, 2,2,2-trichloroethoxy, pentafluoroethoxy and the like.

The term "$C_1$-$C_4$-alkoxy-$C_1$-$C_4$-alkyl" as used herein denotes in each case a straight-chain or branched alkyl group which is bound via an oxygen atom to another alkyl group. Both alkyl groups have usually from 1 to 4 carbon atoms, frequently from 1 to 3 carbon atoms, preferably 1 to 2-carbon atoms. Examples are methoxymethyl, methoxyethyl, methoxy-n-propyl, methoxy-n-butyl, ethoxymethyl, ethoxyethyl, ethoxy-n-propyl, ethoxy-n-butyl, n-propoxymethyl, n-propoxyethyl, n-propoxy-n-propyl, n-propoxy-n-butyl, n-butoxymethyl, n-butoxyethyl, n-butoxy-n-propyl, n-butoxy-n-butyl.

The term "cycloalkyl" as used herein denotes in each case a mono- or bicyclic cycloaliphatic radical having usually from 3 to 8 C atoms or 3 to 6 C atoms, such as cyclopropyl, cyclobutyl, cyclopentyl, cyclohexyl, cycloheptyl, cyclooctyl, bicyclo[2.1.1]hexyl, bicyclo[3.1.1]heptyl, bicyclo[2.2.1]heptyl, and bicyclo[2.2.2]octyl.

The term "cycloalkylmethyl" as used herein denotes in each case a methyl radical which is bound to a cycloalkyl group as defined above. Examples are cyclopropylmethyl, cyclobutylmethyl, cyclopentylmethyl, especially cyclopropylmethyl.

The term "aryl" as used herein denotes in each case a cyclic radical selected from the group consisting of mono-, bi- or tricyclic aromatic radicals. Examples are phenyl, naphthyl and anthracyl, especially phenyl.

The term "aryl-$CH_2$" as used herein denotes in each case a methyl radical, which is bound to an aryl group as described above. Examples are benzyl, naphthylmethyl and anthracylmethyl, especially benzyl.

The term "aryloxy" as used herein denotes in each case an aryl group which is bound via an oxygen atom. Examples are phenoxy, naphthoxy and anthracyloxy, especially phenoxy.

The term "hetaryl" as used herein denotes in each case a heterocyclic radical selected from the group consisting of monocyclic 5- or 6-membered heteroaromatic radicals comprising as ring members 1, 2 or 3 heteroatoms selected from N, O and S. Examples of 5- or 6-membered heteroaromatic radicals include pyridyl, i.e. 2-, 3-, or 4-pyridyl, pyrimidinyl, i.e. 2-, 4- or 5-pyrimidinyl, pyrazinyl, pyridazinyl, i.e. 3- or 4-pyridazinyl, thienyl, i.e. 2- or 3-thienyl, furyl, i.e. 2- or 3-furyl, pyrrolyl, i.e. 2- or 3-pyrrolyl, oxazolyl, i.e. 2-, 3- or 5-oxazolyl, isoxazolyl, i.e. 3-, 4- or 5-isoxazolyl, thiazolyl, i.e. 2-, 3- or 5-thiazolyl, isothiazolyl, i.e. 3-, 4- or 5-isothiazolyl, pyrazolyl, i.e. 1-, 3-, 4- or 5-pyrazolyl, i.e. 1-, 2-, 4- or 5-imidazolyl, oxadiazolyl, e.g. 2- or 5-[1,3,4]oxadiazolyl, 4- or 5-(1,2,3-oxadiazol)yl, 3- or 5-(1,2,4-oxadiazol)yl, 2- or 5-(1,3,4-oxadiazol)yl, thiadiazolyl, e.g. 2- or 5-(1,3,4-thiadiazol)yl, 4- or 5-(1,2,3-thiadiazol)yl, 3- or 5-(1,2,4-thiadiazol)yl, triazolyl, e.g. 1H-, 2H- or 3H-1,2,3-triazol-4-yl, 2H-triazol-3-yl, 1H-, 2H-, or 4H-1,2,4-triazolyl and tetrazolyl, i.e. 1H- or 2H-tetrazolyl.

The term "hetaryl-$CH_2$" as used herein denotes in each case a methyl radical, which is bound to a hetaryl group as described above. Examples are methylpyridyl, i.e. 2-, 3-, or 4-methylpyridyl, methylpyrimidinyl, i.e. 2-, 4- or 5-methylpyrimidinyl, methylpyrazinyl, methylpyridazinyl, i.e. 3- or 4-methylpyridazinyl, methylthienyl, i.e. 2- or 3-methylthienyl, methylfuryl, i.e. 2- or 3-methylfuryl, methylpyrrolyl, i.e. 2- or 3-methylpyrrolyl, methyloxazolyl, i.e. 2-, 3- or 5-methyloxazolyl, methylisoxazolyl, i.e. 3-, 4- or 5-methylisoxazolyl, methylthiazolyl, i.e. 2-, 3- or 5-methylthiazolyl, methylisothiazolyl, i.e. 3-, 4- or 5-methylisothiazolyl, methylpyrazolyl, i.e. 1-, 3-, 4- or 5-methylpyrazolyl, i.e. 1-, 2-, 4- or 5-methylimidazolyl, methyloxadiazolyl, methylthiadiazolyl, methyltriazolyl and methyltetrazolyl, i.e. 1H- or 2H-tetrazolyl.

N-bound heterocycles comprise saturated, non-aromatic heterocyclic rings, which are bound via the nitrogen-ring atom. It is 3- to 10-membered and mono- or bicyclic, especially it is a 3- to 7-membered monocyclic ring. Examples therefore include aziridinyl, azetidinyl, azepanyl, azocanyl, azonanyl, azecanyl, pyrrolidinyl, piperidinyl, imidazolidinyl, pyrazolidinyl, piperazinyl, diazepanyl, diazocanyl, diazonanyl, diazecanyl, oxazolidinyl, isoxazolidinyl, morpholinyl, oxazinanyl, oxazepanyl, oxazocanyl, oxazonanyl, oxazecanyl, thiazolidinyl, isothiazolidinyl, thiazinanyl, thiomorpholinyl, thiazepanyl, thiazocanyl, thiazonanyl, thiazecanyl, oxadiazinanyl, oxadiazepanyl, oxadiazocanyl, oxadiazonanyl, oxadiazecanyl, thiodiazinanyl, thiadiazepanyl, thiadiazocanyl, thiadiazonanyl, thiadiazecanyl, decahydroquinolinyl, decahydroquinazolinyl, deachydronathyridinyl and the like.

The term "C-bound saturated heterocyclyl" as used herein denotes in each case a C-bound heterocyclic radical which is 3- to 10-membered, saturated and having 1 or 2 nitrogen atoms and 0 or 1 heteroatoms, selected from O and S, as ring members. Especially it is 3- to 7-membered, monocyclic radical having 1 or 2 nitrogen atoms and 0 or 1 heteroatoms, selected from O and S, as ring members. The heterocyclyl itself can be unsubstituted or substituted. Examples therefore include aziridinyl, azetidinyl, azepanyl, azocanyl, azonanyl, azecanyl, pyrrolidinyl, piperidinyl, imidazolidinyl, pyrazolidinyl, piperazinyl, diazepanyl, diazocanyl, diazonanyl, diazecanyl, oxazolidinyl, isoxazolidinyl, morpholinyl, oxazinanyl, oxazepanyl, oxazocanyl, oxazonanyl, oxazecanyl, thiazolidinyl, isothiazolidinyl, thiazinanyl, thiomorpholinyl, thiazepanyl, thiazocanyl, thiazonanyl, thiazecanyl, oxadiazinanyl, oxadiazepanyl, oxadiazocanyl, oxadiazonanyl, oxadiazecanyl, thiodiazinanyl, thiadiazepanyl, thiadiazocanyl, thiadiazonanyl, thiadiazecanyl, decahydroquinolinyl, decahydroquinazolinyl, deachydronathyridinyl and the like.

The term "$C_1$-$C_4$-hydrazide" as used herein denotes in each case a hydrazinyl group which is bound to a $C_1$-$C_4$-acyl group. Examples are formic acid hydrozide, acetic acid hydrozide, propionic acid hydrazide and butanoic acid hydrazide.

The term "covalent bond" as used in the definition of Z has to be understood as a covalent single bond.

Preferred compounds of the invention are those, wherein the variables $R^a$, Q, Z, $X^1$, $X^2$, $X^3$ and $X^4$ in formula I independently of each other preferably in any combination have one of the following meanings.

In a particular embodiment of the invention $X^1$ is C—$R^1$. In this embodiment the radical $R^1$ is defined as above. In particular $R^1$ is selected from the group consisting of hydrogen, halogen, in particular chlorine or bromine, $C_1$-$C_6$-alkyl, in particular branched $C_3$-$C_6$-alkyl, such as isopropyl, isobutyl or tert.-butyl, $C_1$-$C_6$-haloalkyl, in particular $C_1$-$C_2$-fluoroalkyl, such as $CF_3$, $CHF_2$, $CH_2CF_3$ or $CF_2CF_3$, $C_1$-$C_6$-alkoxy, in particular $C_1$-$C_3$-alkoxy such as methoxy, ethoxy, n-propoxy, isopropoxy, $C_1$-$C_4$-haloalkoxy, in particular $C_1$-$C_2$-fluoroalkoxy such as $OCF_3$ or $OCHF_2$, $C_3$-$C_8$-cycloalkyl, in particular $C_3$-$C_6$-cycloalkyl such as cyclopropyl, cyclobutyl, cyclopentyl or cyclohexyl, a radical $NR^{1a}R^{1b}$, wherein $R^{1a}$ and $R^{1b}$ are as defined above and wherein at least one of $R^{1a}$ and $R^{1b}$ in particular both $R^{1a}$ and $R^{1b}$, are different from hydrogen, aryl, in particular phenyl, aryl-$CH_2$, in particular benzyl, aryloxy, in particular phenoxy, and hetaryl, in particular pyridinyl, pyrimidinyl, thienyl or furyl, wherein the aryl, in particular phenyl, and hetaryl rings in the last 4 mentioned radicals itself is unsubstituted or carries 1, 2, 3, 4 or 5 identical or different radicals $R^{1c}$.

In this particular embodiment, preference is given to compound, wherein $R^1$ is selected from the group consisting of phenyl, benzyl and phenoxy, wherein the phenyl ring in the last three radicals itself is unsubstituted or carries 1, 2, 3, 4 or 5 identical or different radicals $R^{1c}$.

Likewise preference is given to compounds, wherein $R^1$ is selected from the group consisting of branched $C_3$-$C_6$-alkyl, $C_3$-$C_6$-cycloalkyl and $C_1$-$C_6$-haloalkyl, in particular $C_1$-$C_2$-fluoroalkyl, such as $CF_3$, $CHF_2$, $CH_2CF_3$ or $CF_2CF_3$.

Particular examples of $R^1$ include $CF_3$, chlorine, amino, benzylamino, phenylamino, 4-methylpiperazin-1-yl, 4-morpholinyl, 1-piperazinyl, 1-piperidinyl, 4-methylmorpholinyl, 4-methylpiperidin-1-yl, 1-methylpiperidinyl, phenoxy, phenyl, 4-cyanophenyl, 4-trifluoromethylphenyl, cyclobutyl, cyclopropyl, cyclopentyl, cyclohexyl and 4-fluorophenyl.

In a further particular embodiment of the invention, $R^1$ is a radical $NR^{1a}R^{1b}$ or C-bound 3- to 10-membered, in particular 3- to 7-membered saturated heterocyclyl having 1 or 2 nitrogen atoms and 0 or 1 heteroatom, selected from O and S, as ring members, where the heterocyclyl itself is unsubstituted or carries 1, 2, 3, 4 or 5 identical or different radicals $R^{1c}$. In this further particular embodiment, $R^1$ is especially a radical $NR^{1a}R^{1b}$, where $R^{1a}$ is selected from 2-methoxyethyl, 3-methoxy-n-propyl or 2-ethoxyethyl while $R^{1b}$ is methyl or ethyl or the radical $NR^{1a}R^{1b}$ is morpholinyl, 1,4-oxazepan-4-yl, 4-methylpiperazinyl, 1-pyrrolidinyl or 1-piperidinyl or $R^1$ is 4-methylpiperidin-1-yl or 3-methylpyrrolidin-1-yl.

Particular examples of $R^1$ include $CF_3$, chloro, fluoro, amino, tert.-butyl, benzylamino, phenylamino, phenoxy, phenyl, 4-cyanophenyl, 4-trifluoromethylphenyl, 4-chlorophenyl, 4-fluorophenyl, cyclopropyl, cyclobutyl, cyclopentyl, cyclohexyl, morpholinyl, 1,4-oxazepan-4-yl, 4-methylpiperazinyl, 1-pyrrolidinyl, 1-piperidinyl, 4-methylpiperidin-1-yl, 3-methylpyrrolidin-1-yl, N-(2-methoxyethyl)-N-methylamino, N-(3-methoxy-n-propyl)-N-methylamino, N-(2-ethoxyethyl)-N-methylamino, N-(2-methoxyethyl)-N-ethylamino, N-(3-methoxy-n-propyl)-N-ethylamino and N-(2-ethoxyethyl)-N-ethylamino.

In the radical $NR^{1a}R^{1b}$, wherein at least one of $R^{1a}$ and $R^{1b}$, in particular both $R^{1a}$ and $R^{1b}$, are different from hydrogen, the variable $R^{1a}$ is particularly selected from the group consisting of hydrogen, $C_3$-$C_8$-cycloalkyl, benzyl, phenyl or 5- or 6-membered hetaryl, wherein the phenyl and hetaryl rings in the last three radicals itself are unsubstituted or carries 1, 2, 3, 4 or 5 identical or different radicals $R^{1c}$.

In the radical $NR^{1a}R^{1b}$ the variable $R^{1b}$ is preferably hydrogen or $C_1$-$C_4$-alkyl.

Where present, $NR^{1a}R^{1b}$ may also preferably be a 5- to 10-membered, in particular 5- or 6-membered, mono- or bicyclic N-bound saturated heterocycle, which, in addition to the nitrogen atom, may comprise a further heteroatom selected from O, S and N as ring member and which is unsubstituted or carries 1, 2, 3 or 4 $C_1$-$C_4$-alkyl radicals, examples including 4-morpholinyl, 4-thiomorpholinyl, 1-piperidinyl, 1-pyrrolidinyl, N-methylpiperazin-1-yl, 1,4-oxazepan-4-yl, 4-methylpiperidin-1-yl, or 3-methylpyrrolidin-1-yl.

In a further particular embodiment, $R^1$ is especially a radical $NR^{1a}R^{1b}$ where $R^{1a}$ is selected from 2-methoxyethyl, 3-methoxy-n-propyl or 2-ethoxyethyl while $R^{1b}$ is methyl or ethyl. Examples are N-(2-methoxyethyl)-N-methylamino, N-(3-methoxy-n-propyl)-N-methylamino, N-(2-ethoxyethyl)-N-methylamino, N-(2-methoxyethyl)-N-ethylamino, N-(3-methoxy-n-propyl)-N-ethylamino, N-(2-ethoxyethyl)-N-ethylamino.

Where present, $R^{1c}$ is selected from the group consisting of halogen, CN, OH, $C_1$-$C_4$-alkyl, such as methyl, ethyl, n-propyl or isopropyl, $C_3$-$C_6$-cycloalkyl, in particular cyclopropyl, cyclobutyl, cyclopentyl or cyclohexyl, $C_1$-$C_4$-haloalkyl, in particular $CHF_2$, $CF_3$, $CH_2CF_3$ or $CF_2CF_3$, $C_1$-$C_4$-alkoxy, in particular methoxy or ethoxy, and $C_1$-$C_4$-haloalkoxy.

In a particular embodiment of the invention, $X^2$ is C—$R^2$. In this embodiment, the radical $R^2$ is defined as above. In particular, $R^2$ is selected from the group consisting of hydrogen, halogen, in particular chlorine, $C_1$-$C_6$-alkyl, in particular branched $C_3$-$C_6$-alkyl, such as isopropyl, isobutyl or tert.-butyl, $C_1$-$C_6$-haloalkyl, in particular $C_1$-$C_2$-fluoroalkyl, such as $CF_3$, $CHF_2$, $CH_2CF_3$ or $CF_2CF_3$, $C_1$-$C_6$-alkoxy, in particular $C_1$-$C_3$-alkoxy, such as methoxy, ethoxy, n-propoxy, isopropoxy, $C_1$-$C_4$-haloalkoxy, in particular $C_1$-$C_2$-fluoroalkoxy, such as $OCF_3$ or $OCHF_2$, $C_3$-$C_8$-cycloalkyl, in particular $C_3$-$C_6$-cycloalkyl, such as cyclopropyl, cyclobutyl, cyclopentyl or cyclohexyl, a radical $(CH_2)_nNR^{2a}R^{2b}$, wherein n is 0 or 1 and $R^{ea}$ has one of the meanings given for $R^{1a}$ and $R^{2b}$ has one of the meanings given for $R^{1b}$, aryl, in particular phenyl, aryl-$CH_2$, in particular benzyl, aryloxy, in particular phenoxy, hetaryl, in particular pyridinyl, pyrimidinyl, thienyl or furyl, wherein the aryl, in particular phenyl, and hetaryl rings in the last 4 mentioned radicals itself is unsubstituted or carries 1, 2, 3, 4 or 5 identical or different radicals $R^{2c}$, where $R^{2c}$ has one of the meanings given for $R^{1c}$.

In a particular embodiment of the invention, $R^2$ is selected from the group consisting of aryl, in particular from phenyl, arylmethyl, in particular from benzyl and aryloxy, in particular from phenoxy, wherein the aryl ring in the aforementioned radicals itself is unsubstituted or carries 1, 2, 3, 4 or 5 identical or different radicals R.

In another particular embodiment of the invention, $R^2$ is selected from the group consisting of branched $C_3$-$C_6$-alkyl, $C_3$-$C_6$-cycloalkyl and $C_1$-$C_6$-haloalkyl, in particular $C_1$-$C_2$-fluoroalkyl, such as $CF_3$, $CHF_2$, $CH_2CF_3$ or $CF_2CF_3$.

Particular examples of $R^2$ include $CF_3$, chlorine, amino, benzylamino, phenylamino, 4-methylpiperazin-1-yl, 4-morpholinyl, 1-piperidinyl, 4-methylmorpholinyl, 1-methylpiperidinyl, phenoxy, phenyl, 4-cyanophenyl, 4-trifluoromethylphenyl, cyclobutyl, cyclopropyl, cyclopentyl, cyclohexyl, 4-fluorophenyl.

In a further particular embodiment of the invention, $R^2$ is a radical $NR^{2a}R^{2b}$ or C-bound 3- to 10-membered, in particular 3- to 7-membered saturated heterocyclyl having 1 or 2 nitrogen atoms and 0 or 1 heteroatom, selected from O and S, as ring members, where the heterocyclyl itself is unsubstituted or carries 1, 2, 3, 4 or 5 identical or different radicals $R^{2c}$. In this further particular embodiment, $R^2$ is especially a radical $NR^{2a}R^{2b}$ where $R^{2a}$ is selected from 2-methoxyethyl, 3-methoxy-n-propyl or 2-ethoxyethyl while $R^{1b}$ is methyl or ethyl or the radical $NR^{2a}R^{2b}$ is morpholinyl, 1,4-oxazepan-4-yl, 4-methylpiperazinyl, 1-pyrrolidinyl or 1-piperidinyl or $R^2$ is 4-methylpiperidin-1-yl or 3-methylpyrrolidin-1-yl.

Particular examples of $R^2$ include $CF_3$, chloro, fluoro, amino, tert.-butyl, benzylamino, phenylamino, phenoxy, phenyl, 4-cyanophenyl or 4-trifluoromethylphenyl, 4-chlorophenyl, 4-fluorophenyl, cyclopropyl, cyclobutyl, cyclopentyl, cyclohexyl, morpholinyl, 1,4-oxazepan-4-yl, 4-methylpiperazinyl, 1-pyrrolidinyl or 1-piperidinyl, 4-methylpiperidin-1-yl, 3-methylpyrrolidin-1-yl, N-(2-methoxyethyl)-N-methylamino, N-(3-methoxy-n-propyl)-N-methylamino, N-(2-ethoxyethyl)-N-methylamino, N-(2-methoxyethyl)-N-ethylamino, N-(3-methoxy-n-propyl)-N-ethylamino or N-(2-ethoxyethyl)-N-ethylamino.

In the radical $NR^{2a}R^{2b}$, wherein at least one of $R^{2a}$ and $R^{2b}$, in particular both $R^{2a}$ and $R^{2b}$, are different from hydrogen, the variable $R^{2a}$ is particularly selected from the group consisting of hydrogen, $C_3$-$C_8$-cycloalkyl, benzyl, phenyl or 5- or 6-membered hetaryl, wherein the phenyl and hetaryl rings in the last three radicals itself are unsubstituted or carries 1, 2, 3, 4 or 5 identical or different radicals $R^{2c}$.

In the radical $NR^{2a}R^{2b}$ the variable $R^{2b}$ is preferably hydrogen or $C_1$-$C_4$-alkyl.

Where present, $NR^{2a}R^{2b}$ may also preferably be a 5- to 10-membered, in particular 5- or 6-membered, mono- or bicyclic N-bound saturated heterocycle, which, in addition to the nitrogen atom, may comprise a further heteroatom selected from O, S and N as ring member and which is unsubstituted or carries 1, 2, 3 or 4 $C_1$-$C_4$-alkyl radicals, examples including 4-morpholinyl, 4-thiomorpholinyl, 1-piperidinyl, 1-pyrrolidinyl, N-methylpiperazin-1-yl, 1,4-oxazepan-4-yl, 4-methylpiperidin-1-yl or 3-methylpyrrolidin-1-yl. In a further particular embodiment, $R^2$ is especially a radical $NR^{2a}R^{2b}$, where $R^{2a}$ is selected from 2-methoxyethyl, 3-methoxy-n-propyl or 2-ethoxyethyl while $R^{2b}$ is methyl or ethyl. Examples are N-(2-methoxyethyl)-N-methylamino, N-(3-methoxy-n-propyl)-N-methylamino, N-(2-ethoxyethyl)-N-methylamino, N-(2-methoxyethyl)-N-ethylamino, N-(3-methoxy-n-propyl)-N-ethylamino, N-(2-ethoxyethyl)-N-ethylamino.

Where present, $R^{2c}$ is selected from the group consisting of halogen, CN, OH, $C_1$-$C_4$-alkyl, such as methyl, ethyl, n-propyl or isopropyl, $C_3$-$C_6$-cycloalkyl, in particular cyclopropyl, cyclobutyl, cyclopentyl or cyclohexyl, $C_1$-$C_4$-haloalkyl, in particular $CHF_2$, $CF_3$, $CH_2CF_3$ or $CF_2CF_3$, $C_1$-$C_4$-alkoxy, in particular methoxy or ethoxy, and $C_1$-$C_4$-haloalkoxy.

In a further particular embodiment of the invention, $R^2$ and $R^3$ can together with the carbon atoms to which they are bound, form a fused 5- or 6-membered ring, which itself is unsubstituted or carries 1, 2, 3 or 4 identical or different radicals $R^{23a}$. More preferably, $R^2$ and $R^3$ can together with the carbon atoms to which they are bound, form a fused benzene ring which may be unsubstituted or carry 1 or 2 identical or different radicals $R^{23a}$.

In a particular embodiment, $X^1$ is CH, i.e. $R^1$ is hydrogen, and $X^2$ is C—$R^2$, where $R^2$ is as defined above. In particular, $R^2$ is selected from aryl, $CH_2$-aryl, aryloxy, wherein the aryl ring in the last three radicals itself is unsubstituted or carries 1, 2, 3, 4 or 5 identical or different radicals $R^{1c}$, branched $C_3$-$C_6$-alkyl, $C_1$-$C_6$-haloalkyl or $C_3$-$C_6$-cycloalkyl. In this embodiment $R^2$ is different from hydrogen. Especially, $R^2$ is selected from a group consisting of phenyl, benzyl, phenoxy, wherein the phenyl ring in the last three radicals itself is unsubstituted or carries 1, 2, 3, 4 or 5 identical or different radicals $R^{1c}$.

In a further embodiment, $X^1$ is N while $X^2$ is C—$R^2$, wherein $R^2$ is aryl, $CH_2$-aryl, aryloxy, branched $C_3$-$C_6$-alkyl, $C_1$-$C_6$-haloalkyl or $C_3$-$C_6$-cycloalkyl. In this particular embodiment, $R^2$ is in particular selected from a group consisting of phenyl, benzyl, phenoxy.

In a particular embodiment, $X^2$ is CH or N while $X^1$ is $CR^1$, where $R^1$ is different from hydrogen and else wise defined as above.

$X^3$ is in particular C—$R^3$, where $R^3$ is as defined above and wherein $R^3$ is in $R^{3i}$ particular selected from the group consisting of hydrogen, halogen, $C_1$-$C_4$-alkyl and $C_1$-$C_4$-alkoxy. Especially $R^3$ is selected from the group consisting of hydrogen, chlorine, methyl and trifluoromethyl.

$X^4$ is in particular C—$R^4$, where $R^4$ is as defined above and wherein $R^4$ is in particular selected from the group consisting of hydrogen, halogen, $C_1$-$C_4$-alkyl and $C_1$-$C_4$-alkoxy. Especially $R^4$ is selected from the group consisting of hydrogen, chlorine, methyl and trifluoromethyl.

The radical $R^a$ is selected from the group consisting of $C_3$-$C_6$-cycloalkyl, in particular $C_3$-$C_4$-cycloalkyl, such as cyclopropyl, $C_1$-$C_6$-haloalkyl, in particular $C_1$-$C_2$-fluoroalkyl, such as $CF_3$, $CHF_2$, $CH_2CF_3$, $CF_2CF_3$, $C_1$-$C_6$-alkyl, in particular $C_2$-$C_6$-alkyl, especially $C_3$-$C_6$-alkyl, such as n-propyl, n-butyl, iso-butyl, n-pentyl, the aforementioned alkyl radical can be unsubstituted or carries one radical selected from the group consisting of $C_1$-$C_4$-alkoxy and $C_1$-$C_4$-haloalkoxy, in particular methoxy, ethoxy or $OCF_3$. In particular, $R^a$ is selected from the group consisting of ethyl, n-propyl, n-butyl, cyclopropyl, 2-methoxyethyl, 2-ethoxyethyl, 2,2,2-trifluoroethyl and 2-trifluoromethoxyethyl. In a particular embodiment of the invention, $R^a$ is $C_2$-$C_6$-alkyl, especially $C_2$-$C_4$-alkyl which carries one radical selected from the group consisting of $C_1$-$C_4$-alkoxy and $C_1$-$C_4$-haloalkoxy, in particular methoxy, ethoxy or $OCF_3$, such as 2-methoxyethyl, 2-ethoxyethyl, 2,2,2-trifluoroethyl and 2-trifluoromethoxyethyl. In another particular embodiment, $R^a$ is a radical $NR^{a3}R^{a4}$, where $R^{a3}$ has one of the aforementioned meanings and is in particular selected from hydrogen, $C_1$-$C_4$-alkyl, $C_1$-$C_4$-haloalkyl, $C_3$-$C_6$-cycloalkyl, $C_3$-$C_6$-cycloalkylmethyl and $C_1$-$C_4$-alkoxy-$C_1$-$C_4$-alkyl, while $R^{a4}$ has one of the aforementioned meanings and is in particular selected from hydrogen, $C_1$-$C_4$-alkyl, $C_1$-$C_4$-haloalkyl, $C_3$-$C_6$-cycloalkyl, $C_3$-$C_6$-cycloalkylmethyl, $C_1$-$C_4$-alkoxy-$C_1$-$C_4$-alkyl, C-bound 3- to 7-membered, saturated heterocyclyl, 3- to 7-membered, saturated heterocyclylmethyl, where heterocyclyl in the last two mentioned radicals has 1 or 2 nitrogen atoms and 0 or 1 heteroatom, selected from O and S, as ring members, aryl, aryl-$CH_2$, hetaryl and hetaryl-$CH_2$, wherein the heterocyclyl, aryl and hetaryl rings in the last six radicals themselves are unsubstituted or carry 1, 2, 3, 4 or 5 identical or different radicals $R^{ac}$, where $R^{ac}$ has one of the meanings given for $R^{1c}$.

Where present, $R^{a1}$ and $R^{a2}$ are independently of each other in particular selected from hydrogen, $C_1$-$C_4$-alkyl, $C_3$-$C_6$-cycloalkyl, $C_3$-$C_6$-cycloalkylmethyl and $C_1$-$C_4$-alkoxy-$C_1$-$C_4$-alkyl. Especially, $R^{a1}$ is selected from hydrogen, $C_1$-$C_4$-alkyl, $C_3$-$C_6$-cycloalkyl and $C_1$-$C_4$-alkoxy-$C_1$-$C_4$-alkyl, while $R^{a2}$ is selected from hydrogen and $C_1$-$C_4$-alkyl.

Where present, $R^{a3}$ is selected from hydrogen, $C_1$-$C_4$-alkyl, $C_1$-$C_4$-haloalkyl, $C_3$-$C_6$-cycloalkyl, $C_3$-$C_6$-cycloalkylmethyl and $C_1$-$C_4$-alkoxy-$C_1$-$C_4$-alkyl.

Where present, $R^{a4}$ is selected from hydrogen, $C_1$-$C_4$-alkyl, $C_1$-$C_4$-haloalkyl, $C_3$-$C_6$-cycloalkyl, $C_3$-$C_6$-cycloalkylmethyl, $C_1$-$C_4$-alkoxy-$C_1$-$C_4$-alkyl, C-bound 3 to 10 membered, saturated heterocyclyl, 3- to 7-membered, saturated heterocyclylmethyl, where heterocyclyl in the last two mentioned radicals has 1 or 2 nitrogen atoms and 0 or 1 heteroatoms, selected from O and S, as ring members, aryl, aryl-$CH_2$, hetaryl and hetaryl-$CH_2$, wherein the heterocyclyl, aryl and hetaryl rings in the last six radicals themselves are unsubstituted or carry 1, 2, 3, 4 or 5 identical or different radicals $R^{ac}$, where $R^{ac}$ has one of the meanings given for $R^{1c}$.

The radical Z is selected from the group consisting of a covalent bond, $CR^{Za}R^{Zb}$, O, S or $NR^{Zc}$, in particular a covalent bond, O and NH, especially O and NH.

If Z is a radical $CR^{Za}R^{Zb}$, $R^{Za}$ and $R^{Zb}$ are in particular selected from the group consisting of hydrogen, halogen and $C_1$-$C_4$-alkyl. Especially $R^{Za}$ and $R^{Zb}$ are hydrogen.

If Z is a radical $NR^{Zc}$, $R^{Zc}$ is in particular selected from the group consisting of hydrogen, $C_1$-$C_4$-haloalkyl, $C_3$-$C_6$-cycloalkyl, $C_3$-$C_6$-cycloalkylmethyl, $C_1$-$C_4$-alkyl, which is unsubstituted or carries one radical selected from $C_1$-$C_4$-alkoxy and $NR^{Z1}R^{Z2}$, $S(O)_2R^{Z3}$ or a radical $S(O)_2NR^{Z4}R^{Z5}$.

Where present, $R^{Z1}$ and $R^{Z2}$ are independently of each other in particular selected from the group consisting of hydrogen, $C_3$-$C_6$-cycloalkyl, $C_3$-$C_6$-cycloalkylmethyl, $C_1$-$C_4$-alkyl and $C_1$-$C_4$-alkoxy-$C_1$-$C_4$-alkyl. In particular, $R^{Z1}$ and $R^{Z2}$ may also form together with the nitrogen to which they are attached a 5- or 6-membered N-bound saturated heterocycle, which, in addition to the nitrogen atom, may comprise a further heteroatom, selected from O, S and N as ring member and which is unsubstituted or carries 1, 2, 3 or 4 $C_1$-$C_4$-alkyl radicals, examples including 4-morpholinyl, 4-thiomorpholinyl, 1-piperidinyl, 1-pyrrolidinyl or N-methylpiperazin-1-yl.

Where present, $R^{Z3}$ is in particular selected from $C_3$-$C_6$-cycloalkyl, $C_3$-$C_6$-cycloalkylmethyl, $C_1$-$C_4$-alkyl, phenyl or benzyl, wherein the phenyl ring in the last two mentioned itself is unsubstituted or carries 1, 2, 3, 4 or 5 identical or different radicals selected from halogen, $C_1$-$C_4$-alkyl, $C_1$-$C_4$-haloalkyl, $C_1$-$C_4$-alkoxy and $C_1$-$C_4$-haloalkoxy. Especially, $R^{Z3}$, where present, is $C_1$-$C_4$-alkyl such as methyl.

Where present, $R^{Z4}$ and $R^{Z5}$ have in particular one of the particular meanings given for $R^{Z1}$ and $R^{Z2}$.

In a particular embodiment Z is O or NH.

In another embodiment Z is a covalent bond.

Q is $CH_2$ or $CH_2CH_2$. In a particular embodiment Q is $CH_2$. In another particular embodiment Q is $CH_2CH_2$.

A particular embodiment of the invention relates to compounds according to formula I, their salts and N-oxides, where $X^1$, $X^2$, $X^3$ and $X^4$ are $CR^1$, $CR^2$, $CR^3$ and $CR^4$, respectively, wherein $R^1$, $R^2$, $R^3$ and $R^4$ are as defined above. According to the invention $R^2$ is different from hydrogen, if $R^1$ is hydrogen, while $R^1$ is different from hydrogen, if $R^2$ is hydrogen. In particular, one of W and $R^2$ is hydrogen. In this particular embodiment, $R^3$ is in particular selected from the group consisting of hydrogen, halogen, $C_1$-$C_4$-alkyl and $C_1$-$C_4$-alkoxy, especially from the group consisting of hydrogen, chlorine, methyl and trifluoromethyl. In this particular embodiment, $R^4$ is in particular selected from the group consisting of hydrogen, halogen, $C_1$-$C_4$-alkyl and $C_1$-$C_4$-alkoxy, especially from the group consisting of hydrogen, chlorine, methyl and trifluoromethyl. Especially one or both of the radicals $R^3$ and $R^4$ are different from hydrogen with a particular preference given to compounds, wherein $R^3$ is hydrogen and $R^4$ is halogen, such as chlorine.

A further particular embodiment of the invention relates to compounds according to formula I, their salts and N-oxides, where $X^1$ is N while $X^2$, $X^3$ and $X^4$ are $CR^2$, $CR^3$ and $CR^4$, respectively, wherein $R^2$, $R^3$ and $R^4$ are as defined above. In this particular embodiment, $R^2$ is different from hydrogen. In this particular embodiment, $R^3$ is in particular selected from the group consisting of hydrogen, halogen, $C_1$-$C_4$-alkyl and $C_1$-$C_4$-alkoxy, especially from the group consisting of hydrogen, chlorine, methyl and trifluoromethyl. In this particular embodiment, $R^4$ is in particular selected from the group consisting of hydrogen, halogen, $C_1$-$C_4$-alkyl and $C_1$-$C_4$-alkoxy, especially from the group consisting of hydrogen, chlorine, methyl and trifluoromethyl. Especially one or both of the radicals $R^3$ and $R^4$ are different from hydrogen with a particular preference given to compounds, wherein $R^3$ is hydrogen and $R^4$ is halogen, such as chlorine.

Another particular embodiment of the invention relates to compounds according to formula I, their salts and N-oxides, where $X^2$ is N while $X^1$, $X^3$ and $X^4$ are $CR^1$, $CR^3$ and $CR^4$, respectively, wherein $R^1$, $R^3$ and $R^4$ are as defined above. In this particular embodiment, $R^1$ is different from hydrogen and $R^3$ is in particular selected from the group consisting of hydrogen, halogen, $C_1$-$C_4$-alkyl and $C_1$-$C_4$-alkoxy, especially from the group consisting of hydrogen, chlorine, methyl and trifluoromethyl. In this particular embodiment, $R^4$ is in particular selected from the group consisting of hydrogen, halogen, $C_1$-$C_4$-alkyl and $C_1$-$C_4$-alkoxy, especially from the group consisting of hydrogen, chlorine, methyl and trifluoromethyl. Especially one or both of the radicals $R^3$ and $R^4$ are different from hydrogen with a particular preference given to compounds, wherein $R^3$ is hydrogen and $R^4$ is halogen, such as chlorine.

Another particular embodiment of the invention relates to compounds according to formula I, their salts and N-oxides, where $X^3$ is N while $X^1$, $X^2$ and $X^4$ are $CR^1$, $CR^2$ and $CR^4$, respectively, wherein $R^1$, $R^2$ and $R^4$ are as defined above. According to the invention $R^2$ is different from hydrogen, if $R^1$ is hydrogen, while $R^1$ is different from hydrogen, if $R^2$ is hydrogen. In particular, one of $R^1$ and $R^2$ is hydrogen. In this particular embodiment, $R^4$ is in particular selected from the group consisting of hydrogen, halogen, $C_1$-$C_4$-alkyl and $C_1$-$C_4$-alkoxy, especially from the group consisting of hydrogen, chlorine, methyl and trifluoromethyl.

Another particular embodiment of the invention relates to compounds according to formula I, their salts and N-oxides, where $X^4$ is N while $X^1$, $X^2$ and $X^3$ are $CR^1$, $CR^2$ and $CR^3$, respectively, wherein $R^1$, $R^2$, and $R^3$ are as defined above. According to the invention, $R^2$ is different from hydrogen, if $R^1$ is hydrogen, while $R^1$ is different from hydrogen, if $R^2$ is hydrogen. In particular, one of $R^1$ and $R^2$ is hydrogen. In this particular embodiment, $R^3$ is in particular selected from the group consisting of hydrogen, halogen, $C_1$-$C_4$-alkyl and $C_1$-$C_4$-alkoxy, especially from the group consisting of hydrogen, chlorine, methyl and trifluoromethyl.

Furthermore, one embodiment of the invention relates to compounds of formula I, their salts and N-oxides, wherein Z is bound to $Y^1$, i.e. $Y^1$ is C, $Y^2$ is C—$R^6$, $Y^3$ is C—$R^7$ and $Y^4$ is C—$R^8$ or one of $Y^2$, $Y^3$ or $Y^4$ may also be N. Where occurring, $R^6$, $R^7$ and $R^8$ are independently of each other selected from hydrogen, halogen, $C_1$-$C_4$-alkyl, $C_1$-$C_4$-alkoxy-$C_1$-$C_4$-alkyl, CN, $(CH_2)_n$NR'R'', $C_1$-$C_4$-haloalkyl, $C_1$-$C_4$-alkoxy and $C_1$-$C_4$-haloalkoxy, in particular from hydrogen, halogen, $C_1$-$C_4$-alkyl and $C_1$-$C_4$-alkoxy. In this particular embodiment, preference is given to those compounds, wherein $Y^2$ is C—$R^6$, $Y^3$ is C—$R^7$ and $Y^4$ is C—$R^8$. In this particular embodiment, $R^6$, $R^7$ and $R^8$ are especially hydrogen.

Another embodiment of the invention relates to compounds of formula I, their salts and N-oxides, wherein Z is bound to $Y^2$, i.e. $Y^2$ is C, $Y^1$ is C—$R^5$, $Y^3$ is C—$R^7$ and $Y^4$ is C—$R^8$ or one of $Y^1$, $Y^3$ or $Y^4$ may also be N. Where occurring, $R^5$, $R^7$ and $R^8$ are independently of each other preferably selected from hydrogen, halogen, $C_1$-$C_4$-alkyl, $C_1$-$C_4$-alkoxy-$C_1$-$C_4$-alkyl, CN, $(CH_2)_n$NR'R'', $C_1$-$C_4$-haloalkyl, $C_1$-$C_4$-alkoxy and $C_1$-$C_4$-haloalkoxy, in particular from hydrogen, halogen, $C_1$-$C_4$-alkyl and $C_1$-$C_4$-alkoxy. In this particular embodiment, preference is given to those compounds, wherein $Y^1$ is C—$R^5$, $Y^3$ is C—$R^7$ and $Y^4$ is C—$R^8$. In this particular embodiment, $R^5$ is in particular hydrogen, chlorine, methyl, or methoxy, especially hydrogen. In this particular embodiment, $R^7$ and $R^8$ are especially hydrogen.

Another embodiment of the invention relates to compounds of formula I, their salts and N-oxides, wherein Z is bound to $Y^3$, i.e. $Y^3$ is C, $Y^1$ is C—$R^5$, $Y^2$ is C—$R^6$ and $Y^4$ is C—$R^8$ or one of $Y^1$, $Y^3$ or $Y^4$ may also be N. Where occurring, $R^5$, $R^7$ and $R^8$ are independently of each other preferably selected from hydrogen, halogen, $C_1$-$C_4$-alkyl, $C_1$-$C_4$-alkoxy-$C_1$-$C_4$-alkyl, CN, $(CH_2)_n$NR'R'', $C_1$-$C_4$-haloalkyl, $C_1$-$C_4$-alkoxy and $C_1$-$C_4$-haloalkoxy, in particular from hydrogen, halogen, $C_1$-$C_4$-alkyl and $C_1$-$C_4$-alkoxy. In this particular embodiment, preference is given to those compounds, wherein $Y^1$ is C—$R^5$, $Y^2$ is C—$R^6$ and $Y^4$ is C—$R^8$. In this particular embodiment, $R^5$ is in particular hydrogen, chlorine, methyl, or methoxy, especially hydrogen. In this particular embodiment, $R^6$ and $R^8$ are especially hydrogen.

Another embodiment of the invention relates to compounds of formula I, their salts and N-oxides, wherein Z is bound to $Y^4$, i.e. $Y^4$ is C, $Y^1$ is C—$R^5$, $Y^2$ is C—$R^6$ and $Y^3$ is C—$R^7$ or one of $Y^1$, $Y^2$ or $Y^3$ may also be N. Where occurring, $R^5$, $R^6$ and $R^7$ are independently of each other preferably selected from hydrogen, halogen, $C_1$-$C_4$-alkyl, $C_1$-$C_4$-alkoxy-$C_1$-$C_4$-alkyl, CN, $(CH_2)_n$NR'R'', $C_1$-$C_4$-haloalkyl, $C_1$-$C_4$-alkoxy and $C_1$-$C_4$-haloalkoxy, in particular from hydrogen, halogen, $C_1$-$C_4$-alkyl and $C_1$-$C_4$-alkoxy. In this particular embodiment, preference is given to those compounds, wherein $Y^1$ is C$R^5$, $Y^2$ is C$R^6$ and $Y^3$ is C—$R^7$. In this particular embodiment, $R^5$ is in particular hydrogen, chlorine, methyl, or methoxy, especially hydrogen. In this particular embodiment, $R^6$ and $R^7$ are especially hydrogen.

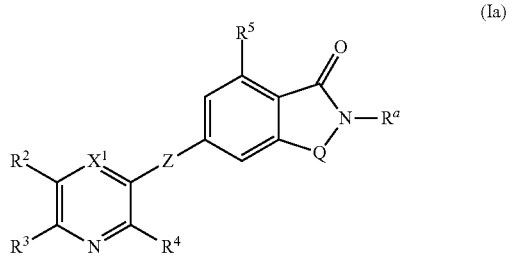
(Ia)

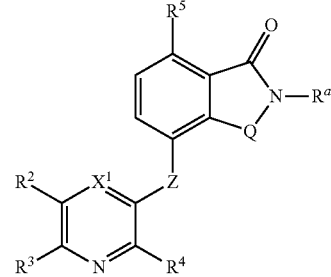
(Ib)

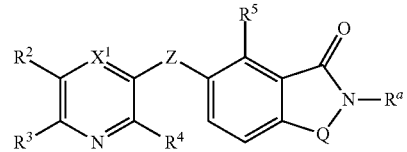
(Ic)

The compounds of the general formulae Ia, Ib and Ic, wherein Z, Q, $X^1$, $R^2$, $R^3$, $R^4$, $R^5$ and $R^a$ are as defined above and their pharmaceutically acceptable salts, represent per se preferred embodiments of the present invention.

A particular embodiment of the invention relates to compounds of formulae Ia, Ib, and Ic, wherein $X^1$ is CH and Z, Q, $R^2$, $R^3$, $R^4$, $R^5$ and $R^a$ are as defined above, but $R^2$ is not hydrogen. In particular Q is $CH_2$ or $CH_2CH_2$. Preferably $R^5$ is hydrogen. In particular Z is O, NH, $CH_2$ or a covalent bond, especially O or NH.

A further embodiment of the invention relates to compounds of formulae Ia, Ib and Ic, wherein $X^1$ is N and Z, Q, $R^2$, $R^3$, $R^4$, $R^5$ and $R^a$ are as defined above, but $R^2$ is not hydrogen. In particular Q is $CH_2$ or $CH_2CH_2$. Preferably $R^5$ is hydrogen. In particular Z is O, NH, $CH_2$ or a covalent bond, especially O or NH.

More preferably are compounds of the general formulae Ia, Ib and Ic which are indicated in the Tables 1 to 296 below. The meanings for $X^1$, $R^2$; $R^3$ and $R^4$ indicated in the Tables A, B and C below represent embodiments of the invention which are likewise preferred independently of one another and especially in combination.

Table 1

Compounds of the formulae Ia, Ib and Ic, in which Z is O, Q is $CH_2$, $R^a$ is $C_2H_5$, $R^3$ is hydrogen, $R^5$ is hydrogen and $X^1$ is C—$R^1$ and the combination of $R^1$, $R^2$ and $R^4$ for a compound in each case corresponds to one row of Table A.

Table 2

Compounds of the formulae Ia, Ib and Ic, in which Z is O, Q is $CH_2$, $R^a$ is $C_2H_5$, $R^3$ is methyl, $R^5$ is hydrogen and $X^1$ is C—$R^1$ and the combination of $R^1$, $R^2$ and $R^4$ for a compound in each case corresponds to one row of Table A.

Table 3

Compounds of the formulae Ia, Ib and Ic, in which Z is O, Q is $CH_2$, $R^a$ is $C_2H_5$, $R^3$ is hydrogen, $R^5$ is methyl and $X^1$ is C—$R^1$ and the combination of $R^1$, $R^2$ and $R^4$ for a compound in each case corresponds to one row of Table A.

Table 4

Compounds of the formulae Ia, Ib and Ic, in which Z is O, Q is $CH_2$, $R^a$ is $C_2H_5$, $R^3$ is methyl, $R^5$ is methyl and $X^1$ is C—$R^1$ and the combination of $R^1$, $R^2$ and $R^4$ for a compound in each case corresponds to one row of Table A.

Table 5

Compounds of the formulae Ia, Ib and Ic, in which Z is O, Q is $CH_2$, $R^a$ is $C_2H_5$, $R^3$ is chlorine, $R^5$ is hydrogen and $X^1$ is C—R¹ and the combination of R¹, R² and R⁴ for a compound in each case corresponds to one row of Table A.

Table 6
Compounds of the formulae Ia, Ib and Ic, in which Z is O, Q is $CH_2$, $R^a$ is $C_2H_5$, $R^3$ is hydrogen, $R^5$ is chlorine and $X^1$ is C—$R^1$ and the combination of $R^1$, $R^2$ and $R^4$ for a compound in each case corresponds to one row of Table A.

Table 7
Compounds of the formulae Ia, Ib and Ic, in which Z is O, Q is $CH_2$, $R^a$ is $C_2H_5$, $R^3$ is chlorine, $R^5$ is chlorine and $X^1$ is C—$R^1$ and the combination of $R^1$, $R^2$ and $R^4$ for a compound in each case corresponds to one row of Table A.

Table 8
Compounds of the formulae Ia, Ib and Ic, in which Z is O, Q is $CH_2$, $R^a$ is $C_2H_5$, $R^3$ is methyl, $R^5$ is chlorine and $X^1$ is C—$R^1$ and the combination of $R^1$, $R^2$ and $R^4$ for a compound in each case corresponds to one row of Table A.

Table 9
Compounds of the formulae Ia, Ib and Ic, in which Z is O, Q is $CH_2$, $R^a$ is $C_2H_5$, $R^3$ is chlorine, $R^5$ is methyl and $X^1$ is C—$R^1$ and the combination of $R^1$, $R^2$ and $R^4$ for a compound in each case corresponds to one row of Table A.

Table 10
Compounds of the formulae Ia, Ib and Ic, in which Z is O, Q is $CH_2$, $R^a$ is n-$C_3H_7$, $R^3$ is hydrogen, $R^5$ is hydrogen and $X^1$ is C—$R^1$ and the combination of $R^1$, $R^2$ and $R^4$ for a compound in each case corresponds to one row of Table A.

Table 11
Compounds of the formulae Ia, Ib and Ic, in which Z is O, Q is $CH_2$, $R^a$ is n-$C_3H_7$, $R^3$ is methyl, $R^5$ is hydrogen and $X^1$ is C—$R^1$ and the combination of $R^1$, $R^2$ and $R^4$ for a compound in each case corresponds to one row of Table A.

Table 12
Compounds of the formulae Ia, Ib and Ic, in which Z is O, Q is $CH_2$, $R^a$ is n-$C_3H_7$, $R^3$ is hydrogen, $R^5$ is methyl and $X^1$ is C—$R^1$ and the combination of $R^1$, $R^2$ and $R^4$ for a compound in each case corresponds to one row of Table A.

Table 13
Compounds of the formulae Ia, Ib and Ic, in which Z is O, Q is $CH_2$, $R^a$ is n-$C_3H_7$, $R^3$ is methyl, $R^5$ is methyl and $X^1$ is C—$R^1$ and the combination of $R^1$, $R^2$ and $R^4$ for a compound in each case corresponds to one row of Table A.

Table 14
Compounds of the formulae Ia, Ib and Ic, in which Z is O, Q is $CH_2$, $R^a$ is n-$C_3H_7$, $R^3$ is chlorine, $R^5$ is hydrogen and $X^1$ is C—$R^1$ and the combination of $R^1$, $R^2$ and $R^4$ for a compound in each case corresponds to one row of Table A.

Table 15
Compounds of the formulae Ia, Ib and Ic, in which Z is O, Q is $CH_2$, $R^a$ is n-$C_3H_7$, $R^3$ is hydrogen, $R^5$ is chlorine and $X^1$ is C—$R^1$ and the combination of $R^1$, $R^2$ and $R^4$ for a compound in each case corresponds to one row of Table A.

Table 16
Compounds of the formulae Ia, Ib and Ic, in which Z is O, Q is $CH_2$, $R^a$ is n-$C_3H_7$, $R^3$ is chlorine, $R^5$ is chlorine and $X^1$ is C—$R^1$ and the combination of $R^1$, $R^2$ and $R^4$ for a compound in each case corresponds to one row of Table A.

Table 17
Compounds of the formulae Ia, Ib and Ic, in which Z is O, Q is $CH_2$, $R^a$ is n-$C_3H_7$, $R^3$ is methyl, $R^5$ is chlorine and $X^1$ is C—$R^1$ and the combination of $R^1$, $R^2$ and $R^4$ for a compound in each case corresponds to one row of Table A.

Table 18
Compounds of the formulae Ia, Ib and Ic, in which Z is O, Q is $CH_2$, $R^a$ is n-$C_3H_7$, $R^3$ is chlorine, $R^5$ is methyl and $X^1$ is C—$R^1$ and the combination of $R^1$, $R^2$ and $R^4$ for a compound in each case corresponds to one row of Table A.

Table 19
Compounds of the formulae Ia, Ib and Ic, in which Z is O, Q is $CH_2$, $R^a$ is n-$C_4H_9$, $R^3$ is hydrogen, $R^5$ is hydrogen and $X^1$ is C—$R^1$ and the combination of $R^1$, $R^2$ and $R^4$ for a compound in each case corresponds to one row of Table A.

Table 20
Compounds of the formulae Ia, Ib and Ic, in which Z is O, Q is $CH_2$, $R^a$ is n-$C_4H_9$, $R^3$ is methyl, $R^5$ is hydrogen and $X^1$ is C—$R^1$ and the combination of $R^1$, $R^2$ and $R^4$ for a compound in each case corresponds to one row of Table A.

Table 21
Compounds of the formulae Ia, Ib and Ic, in which Z is O, Q is $CH_2$, $R^a$ is n-$C_4H_9$, $R^3$ is hydrogen, $R^5$ is methyl and $X^1$ is C—$R^1$ and the combination of $R^1$, $R^2$ and $R^4$ for a compound in each case corresponds to one row of Table A.

Table 22
Compounds of the formulae Ia, Ib and Ic, in which Z is O, Q is $CH_2$, $R^a$ is n-$C_4H_9$, $R^3$ is methyl, $R^5$ is methyl and $X^1$ is C—$R^1$ and the combination of $R^1$, $R^2$ and $R^4$ for a compound in each case corresponds to one row of Table A.

Table 23
Compounds of the formulae Ia, Ib and Ic, in which Z is O, Q is $CH_2$, $R^a$ is n-$C_4H_9$, $R^3$ is chlorine, $R^5$ is hydrogen and $X^1$ is C—$R^1$ and the combination of $R^1$, $R^2$ and $R^4$ for a compound in each case corresponds to one row of Table A.

Table 24
Compounds of the formulae Ia, Ib and Ic, in which Z is O, Q is $CH_2$, $R^a$ is n-$C_4H_9$, $R^3$ is hydrogen, $R^5$ is chlorine and $X^1$ is C—$R^1$ and the combination of $R^1$, $R^2$ and $R^4$ for a compound in each case corresponds to one row of Table A.

Table 25
Compounds of the formulae Ia, Ib and Ic, in which Z is O, Q is $CH_2$, $R^a$ is n-$C_4H_9$, $R^3$ is chlorine, $R^5$ is chlorine and $X^1$ is C—$R^1$ and the combination of $R^1$, $R^2$ and $R^4$ for a compound in each case corresponds to one row of Table A.

Table 26
Compounds of the formulae Ia, Ib and Ic, in which Z is O, Q is $CH_2$, $R^a$ is n-$C_4H_9$, $R^3$ is methyl, $R^5$ is chlorine and $X^1$ is C—$R^1$ and the combination of $R^1$, $R^2$ and $R^4$ for a compound in each case corresponds to one row of Table A.

Table 27
Compounds of the formulae Ia, Ib and Ic, in which Z is O, Q is $CH_2$, $R^a$ is n-$C_4H_9$, $R^3$ is chlorine, $R^5$ is methyl and $X^1$ is C—$R^1$ and the combination of $R^1$, $R^2$ and $R^4$ for a compound in each case corresponds to one row of Table A.

Table 28
Compounds of the formulae Ia, Ib and Ic, in which Z is O, Q is $CH_2$, $R^a$ is 2-methoxyethyl, $R^3$ is hydrogen, $R^5$ is hydrogen and $X^1$ is C—$R^1$ and the combination of $R^1$, $R^2$ and $R^4$ for a compound in each case corresponds to one row of Table A.

Table 29
Compounds of the formulae Ia, Ib and Ic, in which Z is O, Q is $CH_2$, $R^a$ is 2-methoxyethyl, $R^3$ is methyl, $R^5$ is hydrogen and $X^1$ is C—$R^1$ and the combination of $R^1$, $R^2$ and $R^4$ for a compound in each case corresponds to one row of Table A.

Table 30
Compounds of the formulae Ia, Ib and Ic, in which Z is O, Q is $CH_2$, $R^a$ is 2-methoxyethyl, $R^3$ is hydrogen, $R^5$ is methyl and $X^1$ is C—$R^1$ and the combination of $R^1$, $R^2$ and $R^4$ for a compound in each case corresponds to one row of Table A.

Table 31
Compounds of the formulae Ia, Ib and Ic, in which Z is O, Q is $CH_2$, $R^a$ is 2-methoxyethyl, $R^3$ is methyl, $R^5$ is methyl and $X^1$ is C—$R^1$ and the combination of $R^1$, $R^2$ and $R^4$ for a compound in each case corresponds to one row of Table A.

Table 32
Compounds of the formulae Ia, Ib and Ic, in which Z is O, Q is $CH_2$, $R^a$ is 2-methoxyethyl, $R^3$ is chlorine, $R^5$ is hydrogen and $X^1$ is C—$R^1$ and the combination of $R^1$, $R^2$ and $R^4$ for a compound in each case corresponds to one row of Table A.

Table 33
Compounds of the formulae Ia, Ib and Ic, in which Z is O, Q is $CH_2$, $R^a$ is 2-methoxyethyl, $R^3$ is hydrogen, $R^5$ is chlorine and $X^1$ is C—$R^1$ and the combination of $R^1$, $R^2$ and $R^4$ for a compound in each case corresponds to one row of Table A.

Table 34
Compounds of the formulae Ia, Ib and Ic, in which Z is O, Q is $CH_2$, $R^a$ is 2-methoxyethyl, $R^3$ is chlorine, $R^5$ is chlorine and $X^1$ is C—$R^1$ and the combination of $R^1$, $R^2$ and $R^4$ for a compound in each case corresponds to one row of Table A.

Table 35
Compounds of the formulae Ia, Ib and Ic, in which Z is O, Q is $CH_2$, $R^a$ is 2-methoxyethyl, $R^3$ is methyl, $R^5$ is chlorine and $X^1$ is C—$R^1$ and the combination of $R^1$, $R^2$ and $R^4$ for a compound in each case corresponds to one row of Table A.

Table 36
Compounds of the formulae Ia, Ib and Ic, in which Z is O, Q is $CH_2$, $R^a$ is 2-methoxyethyl, $R^3$ is chlorine, $R^5$ is methyl and $X^1$ is C—$R^1$ and the combination of $R^1$, $R^2$ and $R^4$ for a compound in each case corresponds to one row of Table A.

Table 37
Compounds of the formulae Ia, Ib and Ic, in which Z is O, Q is $CH_2CH_2$, $R^a$ is $C_2H_5$, $R^3$ is hydrogen, $R^5$ is hydrogen and $X^1$ is C—$R^1$ and the combination of $R^1$, $R^2$ and $R^4$ for a compound in each case corresponds to one row of Table A.

Table 38
Compounds of the formulae Ia, Ib and Ic, in which Z is O, Q is $CH_2CH_2$, $R^a$ is $C_2H_5$, $R^3$ is methyl, $R^5$ is hydrogen and $X^1$ is C—$R^1$ and the combination of $R^1$, $R^2$ and $R^4$ for a compound in each case corresponds to one row of Table A.

Table 39
Compounds of the formulae Ia, Ib and Ic, in which Z is O, Q is $CH_2CH_2$, $R^a$ is $C_2H_5$, $R^3$ is hydrogen, $R^5$ is methyl and $X^1$ is C—$R^1$ and the combination of $R^1$, $R^2$ and $R^4$ for a compound in each case corresponds to one row of Table A.

Table 40
Compounds of the formulae Ia, Ib and Ic, in which Z is O, Q is $CH_2CH_2$, $R^a$ is $C_2H_5$, $R^3$ is methyl, $R^5$ is methyl and $X^1$ is C—$R^1$ and the combination of $R^1$, $R^2$ and $R^4$ for a compound in each case corresponds to one row of Table A.

Table 41
Compounds of the formulae Ia, Ib and Ic, in which Z is O, Q is $CH_2CH_2$, $R^a$ is $C_2H_5$, $R^3$ is chlorine, $R^5$ is hydrogen and $X^1$ is C—$R^1$ and the combination of $R^1$, $R^2$ and $R^4$ for a compound in each case corresponds to one row of Table A.

Table 42
Compounds of the formulae Ia, Ib and Ic, in which Z is O, Q is $CH_2CH_2$, $R^a$ is $C_2H_5$, $R^3$ is hydrogen, $R^5$ is chlorine and $X^1$ is C—$R^1$ and the combination of $R^1$, $R^2$ and $R^4$ for a compound in each case corresponds to one row of Table A.

Table 43
Compounds of the formulae Ia, Ib and Ic, in which Z is O, Q is $CH_2CH_2$, $R^a$ is $C_2H_5$, $R^3$ is chlorine, $R^5$ is chlorine and $X^1$ is C—$R^1$ and the combination of $R^1$, $R^2$ and $R^4$ for a compound in each case corresponds to one row of Table A.

Table 44
Compounds of the formulae Ia, Ib and Ic, in which Z is O, Q is $CH_2CH_2$, $R^a$ is $C_2H_5$, $R^3$ is methyl, $R^5$ is chlorine and $X^1$ is C—$R^1$ and the combination of $R^1$, $R^2$ and $R^4$ for a compound in each case corresponds to one row of Table A.

Table 45
Compounds of the formulae Ia, Ib and Ic, in which Z is O, Q is $CH_2CH_2$, $R^a$ is $C_2H_5$, $R^3$ is chlorine, $R^5$ is methyl and $X^1$ is C—$R^1$ and the combination of $R^1$, $R^2$ and $R^4$ for a compound in each case corresponds to one row of Table A.

Table 46
Compounds of the formulae Ia, Ib and Ic, in which Z is O, Q is $CH_2CH_2$, $R^a$ is n-$C_3H_7$, $R^3$ is hydrogen, $R^5$ is hydrogen and $X^1$ is C—$R^1$ and the combination of $R^1$, $R^2$ and $R^4$ for a compound in each case corresponds to one row of Table A.

Table 47
Compounds of the formulae Ia, Ib and Ic, in which Z is O, Q is $CH_2CH_2$, $R^a$ is n-$C_3H_7$, $R^3$ is methyl, $R^5$ is hydrogen and $X^1$ is C—$R^1$ and the combination of $R^1$, $R^2$ and $R^4$ for a compound in each case corresponds to one row of Table A.

Table 48
Compounds of the formulae Ia, Ib and Ic, in which Z is O, Q is $CH_2CH_2$, $R^a$ is n-$C_3H_7$, $R^3$ is hydrogen, $R^5$ is methyl and $X^1$ is C—$R^1$ and the combination of $R^1$, $R^2$ and $R^4$ for a compound in each case corresponds to one row of Table A.

Table 49
Compounds of the formulae Ia, Ib and Ic, in which Z is O, Q is $CH_2CH_2$, $R^a$ is n-$C_3H_7$, $R^3$ is methyl, $R^5$ is methyl and $X^1$ is C—$R^1$ and the combination of $R^1$, $R^2$ and $R^4$ for a compound in each case corresponds to one row of Table A.

Table 50
Compounds of the formulae Ia, Ib and Ic, in which Z is O, Q is $CH_2CH_2$, $R^a$ is n-$C_3H_7$, $R^3$ is chlorine, $R^5$ is hydrogen and $X^1$ is C—$R^1$ and the combination of $R^1$, $R^2$ and $R^4$ for a compound in each case corresponds to one row of Table A.

Table 51
Compounds of the formulae Ia, Ib and Ic, in which Z is O, Q is $CH_2CH_2$, $R^a$ is n-$C_3H_7$, $R^3$ is hydrogen, $R^5$ is chlorine and $X^1$ is C—$R^1$ and the combination of $R^1$, $R^2$ and $R^4$ for a compound in each case corresponds to one row of Table A.

Table 52
Compounds of the formulae Ia, Ib and Ic, in which Z is O, Q is $CH_2CH_2$, $R^a$ is n-$C_3H_7$, $R^3$ is chlorine, $R^5$ is chlorine and $X^1$ is C—$R^1$ and the combination of $R^1$, $R^2$ and $R^4$ for a compound in each case corresponds to one row of Table A.

Table 53
Compounds of the formulae Ia, Ib and Ic, in which Z is O, Q is $CH_2CH_2$, $R^a$ is n-$C_3H_7$, $R^3$ is methyl, $R^5$ is chlorine and $X^1$ is C—$R^1$ and the combination of $R^1$, $R^2$ and $R^4$ for a compound in each case corresponds to one row of Table A.

Table 54
Compounds of the formulae Ia, Ib and Ic, in which Z is O, Q is $CH_2CH_2$, $R^a$ is n-$C_3H_7$, $R^3$ is chlorine, $R^5$ is methyl and $X^1$ is C—$R^1$ and the combination of $R^1$, $R^2$ and $R^4$ for a compound in each case corresponds to one row of Table A.

Table 55
Compounds of the formulae Ia, Ib and Ic, in which Z is O, Q is $CH_2CH_2$, $R^a$ is n-$C_4H_9$, $R^3$ is hydrogen, $R^5$ is hydrogen and $X^1$ is C—$R^1$ and the combination of $R^1$, $R^2$ and $R^4$ for a compound in each case corresponds to one row of Table A.

Table 56
Compounds of the formulae Ia, Ib and Ic, in which Z is O, Q is $CH_2CH_2$, $R^a$ is n-$C_4H_9$, $R^3$ is methyl, $R^5$ is hydrogen and $X^1$ is C—$R^1$ and the combination of $R^1$, $R^2$ and $R^4$ for a compound in each case corresponds to one row of Table A.

Table 57
Compounds of the formulae Ia, Ib and Ic, in which Z is O, Q is $CH_2CH_2$, $R^a$ is n-$C_4H_9$, $R^3$ is hydrogen, $R^5$ is methyl and $X^1$ is C—$R^1$ and the combination of $R^1$, $R^2$ and $R^4$ for a compound in each case corresponds to one row of Table A.

Table 58
Compounds of the formulae Ia, Ib and Ic, in which Z is O, Q is $CH_2CH_2$, $R^a$ is n-$C_4H_9$, $R^3$ is methyl, $R^5$ is methyl and $X^1$ is C—R¹ and the combination of R¹, R² and R⁴ for a compound in each case corresponds to one row of Table A.

Table 59
Compounds of the formulae Ia, Ib and Ic, in which Z is O, Q is CH₂CH₂, R$^a$ is n-C₄H₉, R³ is chlorine, R⁵ is hydrogen and X¹ is C—R¹ and the combination of R¹, R² and R⁴ for a compound in each case corresponds to one row of Table A.

Table 60
Compounds of the formulae Ia, Ib and Ic, in which Z is O, Q is CH₂CH₂, R$^a$ is n-C₄H₉, R³ is hydrogen, R⁵ is chlorine and X¹ is C—R¹ and the combination of R¹, R² and R⁴ for a compound in each case corresponds to one row of Table A.

Table 61
Compounds of the formulae Ia, Ib and Ic, in which Z is O, Q is CH₂CH₂, R$^a$ is n-C₄H₉, R³ is chlorine, R⁵ is chlorine and X¹ is C—R¹ and the combination of R¹, R² and R⁴ for a compound in each case corresponds to one row of Table A.

Table 62
Compounds of the formulae Ia, Ib and Ic, in which Z is O, Q is CH₂CH₂, R$^a$ is n-C₄H₉, R³ is methyl, R⁵ is chlorine and X¹ is C—R¹ and the combination of R¹, R² and R⁴ for a compound in each case corresponds to one row of Table A.

Table 63
Compounds of the formulae Ia, Ib and Ic, in which Z is O, Q is CH₂CH₂, R$^a$ is n-C₄H₉, R³ is chlorine, R⁵ is methyl and X¹ is C—R¹ and the combination of R¹, R² and R⁴ for a compound in each case corresponds to one row of Table A.

Table 64
Compounds of the formulae Ia, Ib and Ic, in which Z is O, Q is CH₂CH₂, R$^a$ is 2-methoxyethyl, R³ is hydrogen, R⁵ is hydrogen and X¹ is C—R¹ and the combination of R¹, R² and R⁴ for a compound in each case corresponds to one row of Table A.

Table 65
Compounds of the formulae Ia, Ib and Ic, in which Z is O, Q is CH₂CH₂, R$^a$ is 2-methoxyethyl, R³ is methyl, R⁵ is hydrogen and X¹ is C—R¹ and the combination of R¹, R² and R⁴ for a compound in each case corresponds to one row of Table A.

Table 66
Compounds of the formulae Ia, Ib and Ic, in which Z is O, Q is CH₂CH₂, R$^a$ is 2-methoxyethyl, R³ is hydrogen, R⁵ is methyl and X¹ is C—R¹ and the combination of R¹, R² and R⁴ for a compound in each case corresponds to one row of Table A.

Table 67
Compounds of the formulae Ia, Ib and Ic, in which Z is O, Q is CH₂CH₂, R$^a$ is 2-methoxyethyl, R³ is methyl, R⁵ is methyl and X¹ is C—R¹ and the combination of R¹, R² and R⁴ for a compound in each case corresponds to one row of Table A.

Table 68
Compounds of the formulae Ia, Ib and Ic, in which Z is O, Q is CH₂CH₂, R$^a$ is 2-methoxyethyl, R³ is chlorine, R⁵ is hydrogen and X¹ is C—R¹ and the combination of R¹, R² and R⁴ for a compound in each case corresponds to one row of Table A.

Table 69
Compounds of the formulae Ia, Ib and Ic, in which Z is O, Q is CH₂CH₂, R$^a$ is 2-methoxyethyl, R³ is hydrogen, R⁵ is chlorine and X¹ is C—R¹ and the combination of R¹, R² and R⁴ for a compound in each case corresponds to one row of Table A.

Table 70
Compounds of the formulae Ia, Ib and Ic, in which Z is O, Q is CH₂CH₂, R$^a$ is 2-methoxyethyl, R³ is chlorine, R⁵ is chlorine and X¹ is C—R¹ and the combination of R¹, R² and R⁴ for a compound in each case corresponds to one row of Table A.

Table 71
Compounds of the formulae Ia, Ib and Ic, in which Z is O, Q is CH₂CH₂, R$^a$ is 2-methoxyethyl, R³ is methyl, R⁵ is chlorine and X¹ is C—R¹ and the combination of R¹, R² and R⁴ for a compound in each case corresponds to one row of Table A.

Table 72
Compounds of the formulae Ia, Ib and Ic, in which Z is O, Q is CH₂CH₂, R$^a$ is 2-methoxyethyl, R³ is chlorine, R⁵ is methyl and X¹ is C—R¹ and the combination of R¹, R² and R⁴ for a compound in each case corresponds to one row of Table A.

Tables 73 to 144
Compounds of the formulae Ia, Ib and Ic, in which Z is NH, Q, R$^a$, R³, R⁵ and X¹ correspond to those given in tables 1 to 72 and R¹, R² and R⁴ are as defined in one row of Table A.

Tables 145 to 216
Compounds of the formulae Ia, Ib and Ic, in which Z is CH₂, Q, R$^a$, R³, R⁵ and X¹ correspond to those given in tables 1 to 72 and R¹, R² and R⁴ are as defined in one row of Table A.

Tables 217 to 288
Compounds of the formulae Ia, Ib and Ic, in which Z is a covalent bond, Q, R$^a$, R³, R⁵ and X¹ correspond to those given in tables 1 to 72 and R¹, R² and R⁴ are as defined in one row of Table A.

TABLE A

| No. | R¹ | R² | R⁴ |
|---|---|---|---|
| A1 | H | H | H |
| A2 | CH₃ | H | H |
| A3 | C₂H₅ | H | H |
| A4 | n-C₃H₇ | H | H |
| A5 | CF₃ | H | H |
| A6 | CHF₂ | H | H |
| A7 | CH₂CF₃ | H | H |
| A8 | OCH₃ | H | H |
| A9 | OCH₂—CH₃ | H | H |
| A10 | OCF₃ | H | H |
| A11 | OCH₂—CF₃ | H | H |
| A12 | Phenyl | H | H |
| A13 | Phenoxy | H | H |
| A14 | Benzyl | H | H |
| A15 | Cl | H | H |
| A16 | Br | H | H |
| A17 | I | H | H |
| A18 | NH₂ | H | H |
| A19 | NH-Phenyl | H | H |
| A20 | CN | H | H |
| A21 | NH-Benzyl | H | H |
| A22 | 4-cyanophenyl | H | H |
| A23 | 4-Morpholinyl | H | H |
| A24 | 4-Methylpiperazin-1-yl | H | H |
| A25 | Piperazin-1-yl | H | H |
| A26 | [1,4]Oxazepan-4-yl | H | H |
| A27 | H | CH₃ | H |
| A28 | CH₃ | CH₃ | H |
| A29 | C₂H₅ | CH₃ | H |
| A30 | n-C₃H₇ | CH₃ | H |
| A31 | CF₃ | CH₃ | H |
| A32 | CHF₂ | CH₃ | H |
| A33 | CH₂CF₃ | CH₃ | H |
| A34 | OCH₃ | CH₃ | H |
| A35 | OCH₂—CH₃ | CH₃ | H |
| A36 | OCF₃ | CH₃ | H |
| A37 | OCH₂—CF₃ | CH₃ | H |
| A38 | Phenyl | CH₃ | H |
| A39 | Phenoxy | CH₃ | H |
| A40 | Benzyl | CH₃ | H |
| A41 | Cl | CH₃ | H |
| A42 | Br | CH₃ | H |

TABLE A-continued

| No. | $R^1$ | $R^2$ | $R^4$ |
|---|---|---|---|
| A43 | I | $CH_3$ | H |
| A44 | $NH_2$ | $CH_3$ | H |
| A45 | NH-Phenyl | $CH_3$ | H |
| A46 | CN | $CH_3$ | H |
| A47 | NH-Benzyl | $CH_3$ | H |
| A48 | 4-cyanophenyl | $CH_3$ | H |
| A49 | 4-Morpholinyl | $CH_3$ | H |
| A50 | 4-Methylpiperazin-1-yl | $CH_3$ | H |
| A51 | Piperazin-1-yl | $CH_3$ | H |
| A52 | [1,4]Oxazepan-4-yl | $CH_3$ | H |
| A53 | H | $C_2H_5$ | H |
| A54 | H | n-$C_3H_7$ | H |
| A55 | H | $CF_3$ | H |
| A56 | H | $CHF_2$ | H |
| A57 | H | $CH_2CF_3$ | H |
| A58 | H | $OCH_3$ | H |
| A59 | H | $OCH_2$—$CH_3$ | H |
| A60 | H | $OCF_3$ | H |
| A61 | H | $OCH_2$—$CF_3$ | H |
| A62 | H | Phenyl | H |
| A63 | H | Phenoxy | H |
| A64 | H | Benzyl | H |
| A65 | H | Cl | H |
| A66 | H | Br | H |
| A67 | H | I | H |
| A68 | H | $NH_2$ | H |
| A69 | H | NH-Phenyl | H |
| A70 | H | CN | H |
| A71 | H | NH-Benzyl | H |
| A72 | H | 4-cyanophenyl | H |
| A73 | H | 4-Morpholinyl | H |
| A74 | H | 4-Methylpiperazin-1-yl | H |
| A75 | H | Piperazin-1-yl | H |
| A76 | H | [1,4]Oxazepan-4-yl | H |
| A77 | $CH_3$ | $CH_3$ | H |
| A78 | $CH_3$ | $C_2H_5$ | H |
| A79 | $CH_3$ | n-$C_3H_7$ | H |
| A80 | $CH_3$ | $CF_3$ | H |
| A81 | $CH_3$ | $CHF_2$ | H |
| A82 | $CH_3$ | $CH_2CF_3$ | H |
| A83 | $CH_3$ | $OCH_3$ | H |
| A84 | $CH_3$ | $OCH_2$—$CH_3$ | H |
| A85 | $CH_3$ | $OCF_3$ | H |
| A86 | $CH_3$ | $OCH_2$—$CF_3$ | H |
| A87 | $CH_3$ | Phenyl | H |
| A88 | $CH_3$ | Phenoxy | H |
| A89 | $CH_3$ | Benzyl | H |
| A90 | $CH_3$ | Cl | H |
| A91 | $CH_3$ | Br | H |
| A92 | $CH_3$ | I | H |
| A93 | $CH_3$ | $NH_2$ | H |
| A94 | $CH_3$ | NH-Phenyl | H |
| A95 | $CH_3$ | CN | H |
| A96 | $CH_3$ | NH-Benzyl | H |
| A97 | $CH_3$ | 4-cyanophenyl | H |
| A98 | $CH_3$ | 4-Morpholinyl | H |
| A99 | $CH_3$ | 4-Methylpiperazin-1-yl | H |
| A100 | $CH_3$ | Piperazin-1-yl | H |
| A101 | $CH_3$ | [1,4]Oxazepan-1-yl | H |
| A102 | H | H | $CH_3$ |
| A103 | $CH_3$ | H | $CH_3$ |
| A104 | $C_2H_5$ | H | $CH_3$ |
| A105 | n-$C_3H_7$ | H | $CH_3$ |
| A106 | $CF_3$ | H | $CH_3$ |
| A107 | $CHF_2$ | H | $CH_3$ |
| A108 | $CH_2CF_3$ | H | $CH_3$ |
| A109 | $OCH_3$ | H | $CH_3$ |
| A110 | $OCH_2$—$CH_3$ | H | $CH_3$ |
| A111 | $OCF_3$ | H | $CH_3$ |
| A112 | $OCH_2$—$CF_3$ | H | $CH_3$ |
| A113 | Phenyl | H | $CH_3$ |
| A114 | Phenoxy | H | $CH_3$ |
| A115 | Benzyl | H | $CH_3$ |
| A116 | Cl | H | $CH_3$ |
| A117 | Br | H | $CH_3$ |
| A118 | I | H | $CH_3$ |
| A119 | $NH_2$ | H | $CH_3$ |
| A120 | NH-Phenyl | H | $CH_3$ |
| A121 | CN | H | $CH_3$ |
| A122 | NH-Benzyl | H | $CH_3$ |
| A123 | 4-cyanophenyl | H | $CH_3$ |
| A124 | 4-Morpholinyl | H | $CH_3$ |
| A125 | 4-Methylpiperazin-1-yl | H | $CH_3$ |
| A126 | Piperazin-1-yl | H | $CH_3$ |
| A127 | [1,4]Oxazepan-4-yl | H | $CH_3$ |
| A128 | H | $CH_3$ | $CH_3$ |
| A129 | $CH_3$ | $CH_3$ | $CH_3$ |
| A130 | $C_2H_5$ | $CH_3$ | $CH_3$ |
| A131 | n-$C_3H_7$ | $CH_3$ | $CH_3$ |
| A132 | $CF_3$ | $CH_3$ | $CH_3$ |
| A133 | $CHF_2$ | $CH_3$ | $CH_3$ |
| A134 | $CH_2CF_3$ | $CH_3$ | $CH_3$ |
| A135 | $OCH_3$ | $CH_3$ | $CH_3$ |
| A136 | $OCH_2$—$CH_3$ | $CH_3$ | $CH_3$ |
| A137 | $OCF_3$ | $CH_3$ | $CH_3$ |
| A138 | $OCH_2$—$CF_3$ | $CH_3$ | $CH_3$ |
| A139 | Phenyl | $CH_3$ | $CH_3$ |
| A140 | Phenoxy | $CH_3$ | $CH_3$ |
| A141 | Benzyl | $CH_3$ | $CH_3$ |
| A142 | Cl | $CH_3$ | $CH_3$ |
| A143 | Br | $CH_3$ | $CH_3$ |
| A144 | I | $CH_3$ | $CH_3$ |
| A145 | $NH_2$ | $CH_3$ | $CH_3$ |
| A146 | NH-Phenyl | $CH_3$ | $CH_3$ |
| A147 | CN | $CH_3$ | $CH_3$ |
| A148 | NH-Benzyl | $CH_3$ | $CH_3$ |
| A149 | 4-cyanophenyl | $CH_3$ | $CH_3$ |
| A150 | 4-Morpholinyl | $CH_3$ | $CH_3$ |
| A151 | 4-Methylpiperazin-1-yl | $CH_3$ | $CH_3$ |
| A152 | Piperazin-1-yl | $CH_3$ | $CH_3$ |
| A153 | [1,4]Oxazepan-4-yl | $CH_3$ | $CH_3$ |
| A154 | H | $C_2H_5$ | $CH_3$ |
| A155 | H | n-$C_3H_7$ | $CH_3$ |
| A156 | H | $CF_3$ | $CH_3$ |
| A157 | H | $CHF_2$ | $CH_3$ |
| A158 | H | $CH_2CF_3$ | $CH_3$ |
| A159 | H | $OCH_3$ | $CH_3$ |
| A160 | H | $OCH_2$—$CH_3$ | $CH_3$ |
| A161 | H | $OCF_3$ | $CH_3$ |
| A162 | H | $OCH_2$—$CF_3$ | $CH_3$ |
| A163 | H | Phenyl | $CH_3$ |
| A164 | H | Phenoxy | $CH_3$ |
| A165 | H | Benzyl | $CH_3$ |
| A166 | H | Cl | $CH_3$ |
| A167 | H | Br | $CH_3$ |
| A168 | H | I | $CH_3$ |
| A169 | H | $NH_2$ | $CH_3$ |
| A170 | H | NH-Phenyl | $CH_3$ |
| A171 | H | CN | $CH_3$ |
| A172 | H | NH-Benzyl | $CH_3$ |
| A173 | H | 4-cyanophenyl | $CH_3$ |
| A174 | H | 4-Morpholinyl | $CH_3$ |
| A175 | H | 4-Methylpiperazin-1-yl | $CH_3$ |
| A176 | H | Piperazin-1-yl | $CH_3$ |
| A177 | H | [1,4]Oxazepan-4-yl | $CH_3$ |
| A178 | $CH_3$ | $CH_3$ | $CH_3$ |
| A179 | $CH_3$ | $C_2H_5$ | $CH_3$ |
| A180 | $CH_3$ | n-$C_3H_7$ | $CH_3$ |
| A181 | $CH_3$ | $CF_3$ | $CH_3$ |
| A182 | $CH_3$ | $CHF_2$ | $CH_3$ |
| A183 | $CH_3$ | $CH_2CF_3$ | $CH_3$ |
| A184 | $CH_3$ | $OCH_3$ | $CH_3$ |
| A185 | $CH_3$ | $OCH_2$—$CH_3$ | $CH_3$ |
| A186 | $CH_3$ | $OCF_3$ | $CH_3$ |
| A187 | $CH_3$ | $OCH_2$—$CF_3$ | $CH_3$ |
| A188 | $CH_3$ | Phenyl | $CH_3$ |
| A189 | $CH_3$ | Phenoxy | $CH_3$ |
| A190 | $CH_3$ | Benzyl | $CH_3$ |
| A191 | $CH_3$ | Cl | $CH_3$ |
| A192 | $CH_3$ | Br | $CH_3$ |
| A193 | $CH_3$ | I | $CH_3$ |
| A194 | $CH_3$ | $NH_2$ | $CH_3$ |
| A195 | $CH_3$ | NH-Phenyl | $CH_3$ |
| A196 | $CH_3$ | CN | $CH_3$ |
| A197 | $CH_3$ | NH-Benzyl | $CH_3$ |
| A198 | $CH_3$ | 4-cyanophenyl | $CH_3$ |

TABLE A-continued

| No. | R$^1$ | R$^2$ | R$^4$ |
|---|---|---|---|
| A199 | CH$_3$ | 4-Morpholinyl | CH$_3$ |
| A200 | CH$_3$ | 4-Methylpiperazin-1-yl | CH$_3$ |
| A201 | CH$_3$ | Piperazin-1-yl | CH$_3$ |
| A202 | CH$_3$ | [1,4]Oxazepan-4-yl | CH$_3$ |
| A203 | H | H | Cl |
| A204 | CH$_3$ | H | Cl |
| A205 | C$_2$H$_5$ | H | Cl |
| A206 | n-C$_3$H$_7$ | H | Cl |
| A207 | CF$_3$ | H | Cl |
| A208 | CHF$_2$ | H | Cl |
| A209 | CH$_2$CF$_3$ | H | Cl |
| A210 | OCH$_3$ | H | Cl |
| A211 | OCH$_2$—CH$_3$ | H | Cl |
| A212 | OCF$_3$ | H | Cl |
| A213 | OCH$_2$—CF$_3$ | H | Cl |
| A214 | Phenyl | H | Cl |
| A215 | Phenoxy | H | Cl |
| A216 | Benzyl | H | Cl |
| A217 | Cl | H | Cl |
| A218 | Br | H | Cl |
| A219 | I | H | Cl |
| A220 | NH$_2$ | H | Cl |
| A221 | NH-Phenyl | H | Cl |
| A222 | CN | H | Cl |
| A223 | NH-Benzyl | H | Cl |
| A224 | 4-cyanophenyl | H | Cl |
| A225 | 4-Morpholinyl | H | Cl |
| A226 | 4-Methylpiperazin-1-yl | H | Cl |
| A227 | Piperazin-1-yl | H | Cl |
| A228 | [1,4]Oxazepan-4-yl | H | Cl |
| A229 | H | CH$_3$ | Cl |
| A230 | CH$_3$ | CH$_3$ | Cl |
| A231 | C$_2$H$_5$ | CH$_3$ | Cl |
| A232 | n-C$_3$H$_7$ | CH$_3$ | Cl |
| A233 | CF$_3$ | CH$_3$ | Cl |
| A234 | CHF$_2$ | CH$_3$ | Cl |
| A235 | CH$_2$CF$_3$ | CH$_3$ | Cl |
| A236 | OCH$_3$ | CH$_3$ | Cl |
| A237 | OCH$_2$—CH$_3$ | CH$_3$ | Cl |
| A238 | OCF$_3$ | CH$_3$ | Cl |
| A239 | OCH$_2$—CF$_3$ | CH$_3$ | Cl |
| A240 | Phenyl | CH$_3$ | Cl |
| A241 | Phenoxy | CH$_3$ | Cl |
| A242 | Benzyl | CH$_3$ | Cl |
| A243 | Cl | CH$_3$ | Cl |
| A244 | Br | CH$_3$ | Cl |
| A245 | I | CH$_3$ | Cl |
| A246 | NH$_2$ | CH$_3$ | Cl |
| A247 | NH-Phenyl | CH$_3$ | Cl |
| A248 | CN | CH$_3$ | Cl |
| A249 | NH-Benzyl | CH$_3$ | Cl |
| A250 | 4-cyanophenyl | CH$_3$ | Cl |
| A251 | 4-Morpholinyl | CH$_3$ | Cl |
| A252 | 4-Methylpiperazin-1-yl | CH$_3$ | Cl |
| A253 | Piperazin-1-yl | CH$_3$ | Cl |
| A254 | [1,4]Oxazepan-4-yl | CH$_3$ | Cl |
| A255 | H | C$_2$H$_5$ | Cl |
| A256 | H | n-C$_3$H$_7$ | Cl |
| A257 | H | CF$_3$ | Cl |
| A258 | H | CHF$_2$ | Cl |
| A259 | H | CH$_2$CF$_3$ | Cl |
| A260 | H | OCH$_3$ | Cl |
| A261 | H | OCH$_2$—CH$_3$ | Cl |
| A262 | H | OCF$_3$ | Cl |
| A263 | H | OCH$_2$—CF$_3$ | Cl |
| A264 | H | Phenyl | Cl |
| A265 | H | Phenoxy | Cl |
| A266 | H | Benzyl | Cl |
| A267 | H | Cl | Cl |
| A268 | H | Br | Cl |
| A269 | H | I | Cl |
| A270 | H | NH$_2$ | Cl |
| A271 | H | NH-Phenyl | Cl |
| A272 | H | CN | Cl |
| A273 | H | NH-Benzyl | Cl |
| A274 | H | 4-cyanophenyl | Cl |
| A275 | H | 4-Morpholinyl | Cl |
| A276 | H | 4-Methylpiperazin-1-yl | Cl |
| A277 | H | Piperazin-1-yl | Cl |
| A278 | H | [1,4]Oxazepan-4-yl | Cl |
| A279 | CH$_3$ | CH$_3$ | Cl |
| A280 | CH$_3$ | C$_2$H$_5$ | Cl |
| A281 | CH$_3$ | n-C$_3$H$_7$ | Cl |
| A282 | CH$_3$ | CF$_3$ | Cl |
| A283 | CH$_3$ | CHF$_2$ | Cl |
| A284 | CH$_3$ | CH$_2$CF$_3$ | Cl |
| A285 | CH$_3$ | OCH$_3$ | Cl |
| A286 | CH$_3$ | OCH$_2$—CH$_3$ | Cl |
| A287 | CH$_3$ | OCF$_3$ | Cl |
| A288 | CH$_3$ | OCH$_2$—CF$_3$ | Cl |
| A289 | CH$_3$ | Phenyl | Cl |
| A290 | CH$_3$ | Phenoxy | Cl |
| A291 | CH$_3$ | Benzyl | Cl |
| A292 | CH$_3$ | Cl | Cl |
| A293 | CH$_3$ | Br | Cl |
| A294 | CH$_3$ | I | Cl |
| A295 | CH$_3$ | NH$_2$ | Cl |
| A296 | CH$_3$ | NH-Phenyl | Cl |
| A297 | CH$_3$ | CN | Cl |
| A298 | CH$_3$ | NH-Benzyl | Cl |
| A299 | CH$_3$ | 4-cyanophenyl | Cl |
| A300 | CH$_3$ | 4-Morpholinyl | Cl |
| A301 | CH$_3$ | 4-Methylpiperazin-1-yl | Cl |
| A302 | CH$_3$ | Piperazin-1-yl | Cl |
| A303 | CH$_3$ | [1,4]Oxazepan-4-yl | Cl |

Table 289

Compounds of the formulae Ia, Ib and Ic, in which R$^5$ is hydrogen, X$^1$ is N, Z is O and Q is CH$_2$ and the combination of R$^2$, R$^4$ and R$^a$ for a compound in each case corresponds to one line of Table B.

Table 290

Compounds of the formulae Ia, Ib and Ic, in which R$^5$ is hydrogen, X$^1$ is N, Z is O and Q is CH$_2$CH$_2$ and the combination of R$^2$, R$^4$ and R$^a$ for a compound in each case corresponds to one line of Table B.

Table 291

Compounds of the formulae Ia, Ib and Ic, in which R$^5$ is hydrogen, X$^1$ is N, Z is NH and Q is CH$_2$ and the combination of R$^2$, R$^4$ and R$^a$ for a compound in each case corresponds to one line of Table B.

Table 292

Compounds of the formulae Ia, Ib and Ic, in which R$^5$ is hydrogen, X$^1$ is N, Z is NH and Q is CH$_2$CH$_2$ and the combination of R$^2$, R$^4$ and R$^a$ for a compound in each case corresponds to one line of Table B.

Table 293

Compounds of the formulae Ia, Ib and Ic in which R$^5$ is hydrogen, X$^1$ is N, Z is CH$_2$ and Q is CH$_2$ and the combination of R$^2$, R$^4$ and R$^a$ for a compound in each case corresponds to one line of Table B.

Table 294

Compounds of the formulae Ia, Ib and Ic, in which R$^5$ is hydrogen, X$^1$ is N, Z is CH$_2$ and Q is CH$_2$CH$_2$ and the combination of R$^2$, R$^4$ and R$^a$ for a compound in each case corresponds to one line of Table B.

Table 295

Compounds of the formulae Ia, Ib and Ic, in which R$^5$ is hydrogen, X$^1$ is N, Z is a covalent bond and Q is CH$_2$ and the combination of R$^2$, R$^4$ and R$^a$ for a compound in each case corresponds to one line of Table B.

Table 296

Compounds of the formulae Ia, Ib and Ic, in which R$^5$ is hydrogen, X$^1$ is N, Z is a covalent bond and Q is CH$_2$CH$_2$ and the combination of R$^2$, R$^4$ and R$^a$ for a compound in each case corresponds to one line of Table B.

TABLE B

| No. | R² | R⁴ | Rᵃ |
|---|---|---|---|
| B1 | CH₃ | H | C₂H₅ |
| B2 | n-C₂H₅ | H | C₂H₅ |
| B3 | n-C₃H₇ | H | C₂H₅ |
| B4 | CF₃ | H | C₂H₅ |
| B5 | CHF₂ | H | C₂H₅ |
| B6 | CH₂CF₃ | H | C₂H₅ |
| B7 | OCH₃ | H | C₂H₅ |
| B8 | OCH₂—CH₃ | H | C₂H₅ |
| B9 | OCF₃ | H | C₂H₅ |
| B10 | OCH₂—CF₃ | H | C₂H₅ |
| B11 | Phenyl | H | C₂H₅ |
| B12 | Phenoxy | H | C₂H₅ |
| B13 | Benzyl | H | C₂H₅ |
| B14 | Cl | H | C₂H₅ |
| B15 | Br | H | C₂H₅ |
| B16 | I | H | C₂H₅ |
| B17 | NH₂ | H | C₂H₅ |
| B18 | NH-Phenyl | H | C₂H₅ |
| B19 | CN | H | C₂H₅ |
| B20 | NH-Benzyl | H | C₂H₅ |
| B21 | 4-cyanophenyl | H | C₂H₅ |
| B22 | 4-Morpholinyl | H | C₂H₅ |
| B23 | 4-Methylpiperazin-1-yl | H | C₂H₅ |
| B24 | Piperazin-1-yl | H | C₂H₅ |
| B25 | CH₃ | CH₃ | C₂H₅ |
| B26 | n-C₂H₅ | CH₃ | C₂H₅ |
| B27 | n-C₃H₇ | CH₃ | C₂H₅ |
| B28 | CF₃ | CH₃ | C₂H₅ |
| B29 | CHF₂ | CH₃ | C₂H₅ |
| B30 | CH₂CF₃ | CH₃ | C₂H₅ |
| B31 | OCH₃ | CH₃ | C₂H₅ |
| B32 | OCH₂—CH₃ | CH₃ | C₂H₅ |
| B33 | OCF₃ | CH₃ | C₂H₅ |
| B34 | OCH₂—CF₃ | CH₃ | C₂H₅ |
| B35 | Phenyl | CH₃ | C₂H₅ |
| B36 | Phenoxy | CH₃ | C₂H₅ |
| B37 | Benzyl | CH₃ | C₂H₅ |
| B38 | Cl | CH₃ | C₂H₅ |
| B39 | Br | CH₃ | C₂H₅ |
| B40 | I | CH₃ | C₂H₅ |
| B41 | NH₂ | CH₃ | C₂H₅ |
| B42 | NH-Phenyl | CH₃ | C₂H₅ |
| B43 | CN | CH₃ | C₂H₅ |
| B44 | NH-Benzyl | CH₃ | C₂H₅ |
| B45 | 4-cyanophenyl | CH₃ | C₂H₅ |
| B46 | 4-Morpholinyl | CH₃ | C₂H₅ |
| B47 | 4-Methylpiperazin-1-yl | CH₃ | C₂H₅ |
| B48 | Piperazin-1-yl | CH₃ | C₂H₅ |
| B49 | CH₃ | Cl | C₂H₅ |
| B50 | n-C₂H₅ | Cl | C₂H₅ |
| B51 | n-C₃H₇ | Cl | C₂H₅ |
| B52 | CF₃ | Cl | C₂H₅ |
| B53 | CHF₂ | Cl | C₂H₅ |
| B54 | CH₂CF₃ | Cl | C₂H₅ |
| B55 | OCH₃ | Cl | C₂H₅ |
| B56 | OCH₂—CH₃ | Cl | C₂H₅ |
| B57 | OCF₃ | Cl | C₂H₅ |
| B58 | OCH₂—CF₃ | Cl | C₂H₅ |
| B59 | Phenyl | Cl | C₂H₅ |
| B60 | Phenoxy | Cl | C₂H₅ |
| B61 | Benzyl | Cl | C₂H₅ |
| B62 | Cl | Cl | C₂H₅ |
| B63 | Br | Cl | C₂H₅ |
| B64 | I | Cl | C₂H₅ |
| B65 | NH₂ | Cl | C₂H₅ |
| B66 | NH-Phenyl | Cl | C₂H₅ |
| B67 | CN | Cl | C₂H₅ |
| B68 | NH-Benzyl | Cl | C₂H₅ |
| B69 | 4-cyanophenyl | Cl | C₂H₅ |
| B70 | 4-Morpholinyl | Cl | C₂H₅ |
| B71 | 4-Methylpiperazin-1-yl | Cl | C₂H₅ |
| B72 | Piperazin-1-yl | Cl | C₂H₅ |
| B73 | CH₃ | H | n-C₄H₉ |
| B74 | n-C₂H₅ | H | n-C₄H₉ |
| B75 | n-C₃H₇ | H | n-C₄H₉ |
| B76 | CF₃ | H | n-C₄H₉ |
| B77 | CHF₂ | H | n-C₄H₉ |
| B78 | CH₂CF₃ | H | n-C₄H₉ |
| B79 | OCH₃ | H | n-C₄H₉ |
| B80 | OCH₂—CH₃ | H | n-C₄H₉ |
| B81 | OCF₃ | H | n-C₄H₉ |
| B82 | OCH₂—CF₃ | H | n-C₄H₉ |
| B83 | Phenyl | H | n-C₄H₉ |
| B84 | Phenoxy | H | n-C₄H₉ |
| B85 | Benzyl | H | n-C₄H₉ |
| B86 | Cl | H | n-C₄H₉ |
| B87 | Br | H | n-C₄H₉ |
| B88 | I | H | n-C₄H₉ |
| B89 | NH₂ | H | n-C₄H₉ |
| B90 | NH-Phenyl | H | n-C₄H₉ |
| B91 | CN | H | n-C₄H₉ |
| B92 | NH-Benzyl | H | n-C₄H₉ |
| B93 | 4-cyanophenyl | H | n-C₄H₉ |
| B94 | 4-Morpholinyl | H | n-C₄H₉ |
| B95 | 4-Methylpiperazin-1-yl | H | n-C₄H₉ |
| B96 | Piperazin-1-yl | H | n-C₄H₉ |
| B97 | CH₃ | CH₃ | n-C₄H₉ |
| B98 | n-C₂H₅ | CH₃ | n-C₄H₉ |
| B99 | n-C₃H₇ | CH₃ | n-C₄H₉ |
| B100 | CF₃ | CH₃ | n-C₄H₉ |
| B101 | CHF₂ | CH₃ | n-C₄H₉ |
| B102 | CH₂CF₃ | CH₃ | n-C₄H₉ |
| B103 | OCH₃ | CH₃ | n-C₄H₉ |
| B104 | OCH₂—CH₃ | CH₃ | n-C₄H₉ |
| B105 | OCF₃ | CH₃ | n-C₄H₉ |
| B106 | OCH₂—CF₃ | CH₃ | n-C₄H₉ |
| B107 | Phenyl | CH₃ | n-C₄H₉ |
| B108 | Phenoxy | CH₃ | n-C₄H₉ |
| B109 | Benzyl | CH₃ | n-C₄H₉ |
| B110 | Cl | CH₃ | n-C₄H₉ |
| B111 | Br | CH₃ | n-C₄H₉ |
| B112 | I | CH₃ | n-C₄H₉ |
| B113 | NH₂ | CH₃ | n-C₄H₉ |
| B114 | NH-Phenyl | CH₃ | n-C₄H₉ |
| B115 | CN | CH₃ | n-C₄H₉ |
| B116 | NH-Benzyl | CH₃ | n-C₄H₉ |
| B117 | 4-cyanophenyl | CH₃ | n-C₄H₉ |
| B118 | 4-Morpholinyl | CH₃ | n-C₄H₉ |
| B119 | 4-Methylpiperazin-1-yl | CH₃ | n-C₄H₉ |
| B120 | Piperazin-1-yl | CH₃ | n-C₄H₉ |
| B121 | CH₃ | Cl | n-C₄H₉ |
| B122 | n-C₂H₅ | Cl | n-C₄H₉ |
| B123 | n-C₃H₇ | Cl | n-C₄H₉ |
| B124 | CF₃ | Cl | n-C₄H₉ |
| B125 | CHF₂ | Cl | n-C₄H₉ |
| B126 | CH₂CF₃ | Cl | n-C₄H₉ |
| B127 | OCH₃ | Cl | n-C₄H₉ |
| B128 | OCH₂—CH₃ | Cl | n-C₄H₉ |
| B129 | OCF₃ | Cl | n-C₄H₉ |
| B130 | OCH₂—CF₃ | Cl | n-C₄H₉ |
| B131 | Phenyl | Cl | n-C₄H₉ |
| B132 | Phenoxy | Cl | n-C₄H₉ |
| B133 | Benzyl | Cl | n-C₄H₉ |
| B134 | Cl | Cl | n-C₄H₉ |
| B135 | Br | Cl | n-C₄H₉ |
| B136 | I | Cl | n-C₄H₉ |
| B137 | NH₂ | Cl | n-C₄H₉ |
| B138 | NH-Phenyl | Cl | n-C₄H₉ |
| B139 | CN | Cl | n-C₄H₉ |
| B140 | NH-Benzyl | Cl | n-C₄H₉ |
| B141 | 4-cyanophenyl | Cl | n-C₄H₉ |
| B142 | 4-Morpholinyl | Cl | n-C₄H₉ |
| B143 | 4-Methylpiperazin-1-yl | Cl | n-C₄H₉ |
| B144 | Piperazin-1-yl | Cl | n-C₄H₉ |

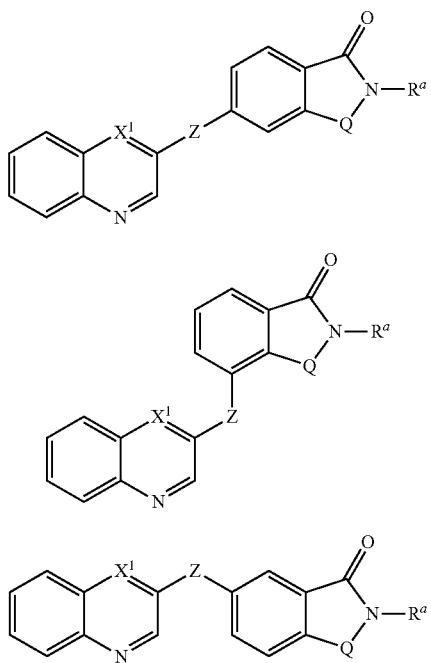

Table 297
Compounds of the formulae Id, Ie and If, in which $X^1$ is CH and the combination of Z, Q and $R^a$ for a compound in each case corresponds to one line of Table C.

Table 298
Compounds of the formulae Id, Ie and If, in which $X^1$ is N and the combination of Z, Q and $R^a$ for a compound in each case corresponds to one line of Table C.

TABLE C

| No. | Z | Q | $R^a$ |
|-----|---|---|-------|
| C1 | O | $CH_2$ | $C_2H_5$ |
| C2 | NH | $CH_2$ | $C_2H_5$ |
| C3 | $CH_2$ | $CH_2$ | $C_2H_5$ |
| C4 | covalent bond | $CH_2$ | $C_2H_5$ |
| C5 | O | $CH_2CH_2$ | $C_2H_5$ |
| C6 | NH | $CH_2CH_2$ | $C_2H_5$ |
| C7 | $CH_2$ | $CH_2CH_2$ | $C_2H_5$ |
| C8 | covalent bond | $CH_2CH_2$ | $C_2H_5$ |
| C9 | O | $CH_2$ | $C_4H_9$ |
| C10 | NH | $CH_2$ | $C_4H_9$ |
| C11 | $CH_2$ | $CH_2$ | $C_4H_9$ |
| C12 | covalent bond | $CH_2$ | $C_4H_9$ |
| C13 | O | $CH_2CH_2$ | $C_4H_9$ |
| C14 | NH | $CH_2CH_2$ | $C_4H_9$ |
| C15 | $CH_2$ | $CH_2CH_2$ | $C_4H_9$ |
| C16 | covalent bond | $CH_2CH_2$ | $C_4H_9$ |

Particular examples are the following compounds, their N-oxides and pharmaceutical acceptable salts:
2-butyl-5-(4-phenylpyridin-3-ylamino)isoindolin-1-one
2-butyl-5-(5-phenylpyridin-3-ylamino)isoindolin-1-one
2-butyl-5-(4-phenylpyridin-3-yloxy)isoindolin-1-one
2-butyl-7-chloro-5-[(5-phenylpyridin-3-yl)amino]-2,3-dihydro-1H-isoindol-1-one
2-butyl-5-{[5-(piperazin-1-yl)pyridin-3-yl]amino}-2,3-dihydro-1H-isoindol-1-one
2-butyl-5-{[2-chloro-5-(piperazin-1-yl)pyridin-3-yl]amino}-2,3-dihydro-1H-isoindol-1-one
2-butyl-5-[(5-chloropyridin-3-yl)amino]-2,3-dihydro-1H-isoindol-1-one
2-butyl-5-{[5-(morpholin-4-yl)pyridin-3-yl]amino}-2,3-dihydro-1H-isoindol-1-one
2-butyl-5-{[2-chloro-5-(4-methylpiperazin-1-yl)pyridin-3-yl]amino}-2,3-dihydro-1H-isoindol-1-one
2-butyl-5-{[5-(4-methylpiperazin-1-yl)pyridin-3-yl]amino}-2,3-dihydro-1H-isoindol-1-one
2-butyl-5-[(5-phenylpyridin-3-yl)oxy]-2,3-dihydro-1H-isoindol-1-one
2-butyl-4-[(5-phenylpyridin-3-yl)oxy]-2,3-dihydro-1H-isoindol-1-one trifluoroacetate
2-butyl-5-[(5-phenylpyridin-3-yl)oxy]-3,4-dihydroisoquinolin-1(2H)-one trifluoroacetate
2-butyl-6-[(5-phenylpyridin-3-yl)oxy]-3,4-dihydroisoquinolin-1(2H)-one trifluoroacetate
2-butyl-6-[(5-phenylpyridin-3-yl)oxy]-2,3-dihydro-1H-isoindol-1-one trifluoroacetate
2-butyl-5-[(5-phenylpyridin-3-yl)methyl]-2,3-dihydro-1H-isoindol-1-one
2-butyl-5-(quinolin-3-ylamino)-2,3-dihydro-1H-isoindol-1-one
2-butyl-5-(quinoxalin-2-ylamino)-2,3-dihydro-1H-isoindol-1-one
2-butyl-5-(6-phenyl-pyrazin-2-ylamino)-2,3-dihydro-isoindol-1-one
2-butyl-5-(5-phenylpyridin-3-yl)-2,3-dihydro-1H-isoindol-1-one
2-butyl-5-{[2-chloro-5-(piperazin-1-yl)pyridine-3-yl]oxy}-3,4-dihydroisoquinolin-1(2H)-one
2-[(2-butyl-1-oxo-2,3-dihydro-1H-isoindol-5-yl)amino]-6-chloro-4-(trifluoromethyl)pyridine-3-carbonitrile
2-butyl-5-[(2-chloropyridin-3-yl)amino]-2,3-dihydro-1H-isoindol-1-one
2-butyl-5-{[2-chloro-5-(4-methylpiperazin-1-yl)pyridine-3-yl]oxy}-3,4-dihydroisoquinolin-1(2H)-one
2-(2-methoxyethyl)-5-[(5-phenylpyridin-3-yl)amino]-2,3-dihydro-1H-isoindol-1-one and
2-(2-methoxyethyl)-5-[(5-phenylpyridin-3-yl)amino]-2,3-dihydro-1H-isoindol-1-one.

Compounds of formula I can principally prepared by the reactions outlined in scheme 1 or scheme 2.

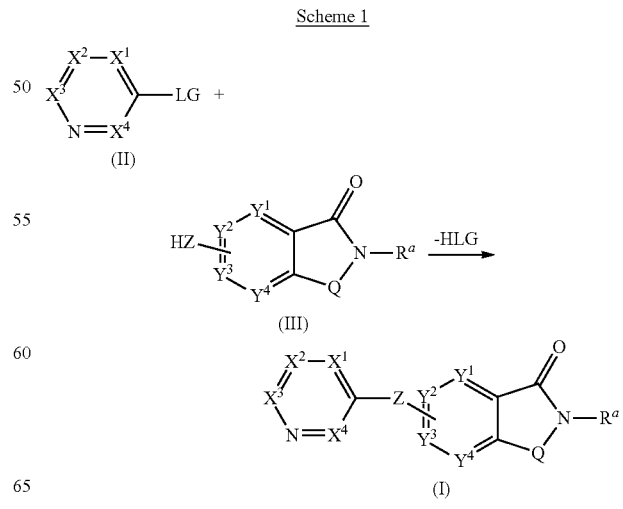

Scheme 1

Scheme 2

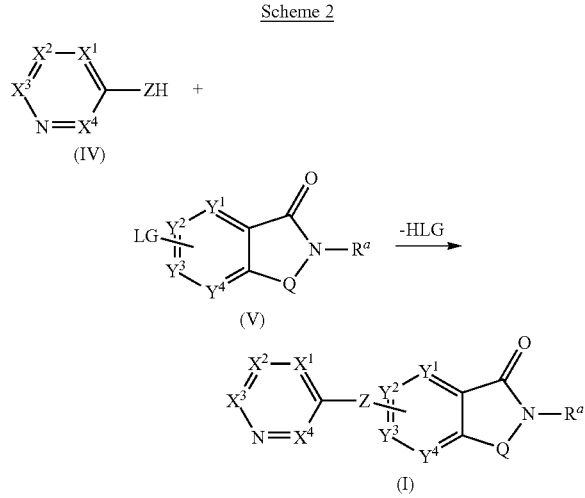

In scheme 1 the variables $R^a$, $Q$, $X^1$, $X^2$, $X^3$, $X^4$, $Y^1$, $Y^2$, $Y^3$ and $Y^4$ are defined as described above. Z is O, S or $NR^{Zc}$. LG represents a leaving group, which can be replaced by any nucleophilic group. Examples of leaving groups are halogen, such as bromine or iodine or haloalkyl- or arylsulfonates, such as mesylate, tosylate and triflate. According to scheme 1 or scheme 2, the compound II and IV, respectively, is reacted with compound III to form compound I under the condition of a nucleophilic substitution reaction, see e.g. J. March, Advanced Organic Chemistry, fourth edition, Wiley-Interscience, New York, 1992, page 293 ff. and the literature cited therein. As it is well known to a person skilled in the art, the addition of a base (auxiliary base) can be beneficial. Examples of bases includes inorganic bases, e.g. alkalimetal hydroxides or alkalimetal carbonates, such as NaOH, $K_2CO_3$, $CsCO_3$, KOH and also organic bases like tertiary amines, e.g. triethylamin, 1,8-diazabicyclo[5.4.0]undec-7-en (DBU) or 1,5-diazabicyclo[4.3.0]non-5-en (DBN). Furthermore, the addition of a catalyst can also be beneficial. Examples of catalyst are transition metal catalyst, such as palladium or platinum catalyst. Ligands such as 2,2'-bis(diphenylphosphino)-1,1'-binaphthyl (BINAP) or 2-dicyclohexylphosphino-2',4',6'-triisopropylbiphenyl (X-Phos) may improve the activity of the catalyst [Journal of the American Chemical Society 116(13), 5969-5970 (1994)].

The compounds, wherein Z is a covalent bond or $CR^{Za}R^{Zb}$, can be prepared by Suzuki cross-coupling reaction between the corresponding boronic ester and the corresponding bromide (s. JACS 2007, 129(6), 1486-7). The boronic acid is introducible as its pinacol ester protected form, by reaction with bis(pinacolato)diboron and catalysis using $PdCl_2.dppf$ in the presence of potassium acetate (s. J. Med. Chem. 2009, 52(19), 6097-106).

Compounds of the formula I, wherein Z is S(O) or $S(O)_2$, can be prepared from the compounds of the formula I, wherein Z is S by standard oxidation methods, as described e.g. in WO 2006/058753.

The N-oxides may be prepared from the compounds of formula I according to conventional oxidation methods, for example by treating said compounds with an organic peracid, such as metachloroperbenzoic acid or 3-chloroperbenzoic acid [Journal of Medicinal Chemistry 38(11), 1892-1903 (1995), WO 03/64572]; or with inorganic oxidizing agents, such as hydrogen peroxide [cf. Journal of Heterocyclic Chemistry 18 (7), 1305-1308 (1981)] or oxone [cf. Journal of the American Chemical Society 123(25), 5962-5973 (2001)]. The oxidation may lead to pure mono-N-oxides or to a mixture of different N-oxides, which can be separated by conventional methods, such as chromatography.

The reactions are usually performed in an organic solvent, including aprotic organic solvent, e.g. substituted amides, lactames and ureas, such as dimethylformamide, dimethylacetamide, N-methylpyrrolidone, tetramethyl urea, cyclic ethers such as dioxane, tetrahydrofurane, halogenated hydrocarbons, such as dichloromethane, and mixtures thereof as well as mixtures thereof with $C_1$-$C_6$-alkanols and/or water.

The reactions described above will be usually performed at temperatures ranging from −10° C. to 250° C., depending on the reactivity of the used compounds. Heating devices, such as microwaves or oil bath, can be used.

The utility of the compounds in accordance with the present invention as modulators of metabotropic glutamate receptor activity, in particular mGlu2 activity, may be demonstrated by methodology known in the art. The compounds of the present invention can be tested e.g. by evaluating intracellular $Ca^{2+}$ concentrations in cells permanently expressing human mGlu receptor, the rat glutamate transporter rGLAST and the Galpha16 subunit of the G-protein complex under standard conditions in a fluorometric imaging plate reader (FLIPR, Molecular Devices, Union City, Calif. 94587, USA) by measuring the response of the cells to a test compound in the absence of presence of glutamate. The FLIPR assay is a common functional assay to monitor native or recombinant Galphaq-coupled receptors, and native or recombinant receptors normally linked to other G-protein signalling cascades, which are coupled to calcium through co-expression of an alpha subunit of a promiscuous or chimeric G-protein. In the assay the increase of intracellular calcium is measured through a calcium-dependent fluorescent dye (e.g. Fluo-4 AM) in the FLIPR instrument.

For the purpose of the present study, a cell line permanently expressing a human mGlu receptor, such as the mGlu2 receptor, the rat glutamate transporter rGLAST and the GalphaG16 may be generated by transfection as described in the examples. For selection of a suitable cell clone and also the subsequent measurements, the selected clone the cells will be plated on suitable multiwell plates in a suitable medium (e.g. DMEM Glutamax (GIBCO #21885-025)/10% dialyzed FCS). Cells may be selected by gentamycin treatment as described in the examples. Cells will then be loaded with a suitable $Ca^{2+}$ sensitive fluorescence dye, e.g. with 2 µM Fluo-4 AM (Molecular Probes, F14201). Cells will then be washed with a suitable buffer (e.g. HEPES) and the thus treated plates will be measured in a fluorometric imaging plate reader (e.g. FLIPR, Molecular Devices, Union City, Calif. 94587, USA).

The compounds of the present invention were tested in the above-described FLIPR assay using the selected cell clone. Increased intracellular calcium levels were quantified following addition of test compound (agonism), as well as following addition of a submaximal concentration of glutamate (potentiation).

For the determination of the effect of the test compound by itself (agonism) or by increasing the response to a submaximal concentration (e.g. 1 µM) of glutamate (potentiation), the resulting signal is determined by subtraction of the background fluorescence from the maximal fluorescent peak height of the respective response. In the FLIPR instrument the compound is given to the cell and its fluorescence response quantified by the FLIPR instrument (agonism). The concentration at which the compound exerts half its maximal effect is named the 'effective concentration 50' or '$EC_{50}$'. The maximal effect induced by the test substance is normalized to the maximal effect exerted by 100 µM glutamate (set at 100%).

After addition of the test compound to the plate, a submaximal concentration of glutamate (e.g. 1 µM glutamate) will be added. A potentiator enhances the response of the receptor to glutamate. The response to glutamate in the presence of test compound is quantified. The concentration at which the test compound is able to exert half its maximal potentiation effect to glutamate is named the '$EC_{50}$'. The maximal response to the submaximal concentration of glutamate (e.g. 1 micromolar glutamate) in the presence of test compound is normalized to the maximal effect exerted by 100 micromolar glutamate (set at 100%). Least squares curve fitting with a four-parameter equation is then applied to the resulting dose-response curve to determine the resulting $EC_{50}$ values (Graph Pad Prism).

A control cell line, HEK293 cells expressing permanently rGLAST and Galpha16 was also plated to a multiwell plate for parallel testing to verify specificity of the test compound for mGlu2 receptor agonism or potentiation.

The compounds of the invention can be further characterized by measurement of their efficacy and potency to inhibit forskolin-induced cAMP levels in these cells on their own (agonism) or to potentiate the effect of glutamate (potentiation). Cyclic AMP levels were quantified using Alphascreen technology (PerkinElmer Life and Analytical Sciences, 710 Bridgeport Avenue, Shelton, Conn. USA) as described by the manufacturer for determining the effects of Galphai coupled receptors.

The concentration at which a compound exerts half its maximal effect is named the 'effective concentration 50' or '$EC_{50}$'. The maximal effect induced by the test substance is normalized to the maximal effect exerted by 100 µM glutamate (100%). Least squares curve fitting with a four-parameter equation is then applied to the resulting dose-response curve to determine the resulting $EC_{50}$ values (Graph Pad Prism).

In particular, the compounds of the following examples had activity in potentiating the mGlu2 receptor in the aforementioned assays, generally with an $EC_{50}$ of not more than about 10 µM. Preferred compounds within the present invention had activity in potentiating the mGlu2 receptor in the aforementioned assays with an $EC_{50}$ of less than 1 µM, in particular less than 0.5 µM, more preferably of at most 0.2 µM, of at most 0.1 µM. Such a result is indicative of the intrinsic activity of the compounds in use as positive modulators of mGlu2 receptor activity.

As stated above, the compounds of the present invention are positive modulators of metabotropic glutamate (mGluR) receptor function, in particular they are positive modulators of mGlu2 receptors. Thus, the compounds of the present invention can be used for treating, preventing, ameliorating, controlling or reducing the risk of a variety of neurological and psychiatric disorders associated with glutamate dysfunction, including one or more of the following conditions or diseases: acute neurological and psychiatric disorders, such as cerebral deficits subsequent to cardiac bypass surgery and grafting, stroke, cerebral ischemia, spinal cord trauma, head trauma, perinatal hypoxia, cardiac arrest, hypoglycemic neuronal damage, dementia (including AIDS-induced dementia), Alzheimer's disease, Huntington's Chorea, amyotrophic lateral sclerosis, ocular damage, retinopathy, cognitive disorders, idiopathic and drug-induced Parkinson's disease, muscular spasms and disorders associated with muscular spasticity including tremors, epilepsy, convulsions, migraine (including migraine headache), urinary incontinence, disorders associated with substance tolerance, disorders associated with substance withdrawal (including substances such as opiates, nicotine, tobacco products, alcohol, benzodiazepines, cocaine, sedatives, hypnotics, etc.), psychosis, schizophrenia, anxiety (including generalized anxiety disorder, panic disorder, and obsessive compulsive disorder), mood disorders (including depression, mania, bipolar disorders), trigeminal neuralgia, hearing loss, tinnitus, macular degeneration of the eye, emesis, brain edema, pain (including acute and chronic pain states, severe pain, intractable pain, neuropathic pain, and post-traumatic pain), tardive dyskinesia, sleep disorders (including narcolepsy), attention deficit/hyperactivity disorder, and conduct disorder.

Of the disorders above, the treatment of schizophrenia, anxiety, depression, substance-related disorders, migraine, and epilepsy are of particular importance.

Therefore, the present invention relates to a method for treating a medical disorder, selected from neurological and psychiatric disorders associated with glutamate dysfunction, said method comprising administering an effective amount of at least one compound of the present invention to a subject in need thereof.

The compounds of the present invention frequently show an affinity towards the serotonin $5HT_{2A}$ receptor. In particular the compounds of the present invention are antagonist of the serotonin $5HT_{2A}$ receptor. Preferred compounds of the present invention have binding constants $Ki(5HT_{2A})$ below 1 µM, in particular of at most 0.5 µM, more preferably at most 250 nM or especially at most 100 nM. Thus the compounds of the present invention are particularly useful for treating the above mentioned disorders, in particular psychiatric disorders, such as schizophrenia, psychosis, cognitive disorders, drug abuse (i.e. disorders associated with substance tolerance, disorders associated with substance withdrawal (including substances, such as opiates, nicotine, tobacco products, alcohol, benzodiazepines, cocaine, sedatives, hypnotics, etc.), anxiety (including generalized anxiety disorder, panic disorder, and obsessive compulsive disorder). The affinity towards the 5HT2A receptor as well as the antagonistic action can be determined by routine screening techniques, a skilled person is familiar with (for reviews see e.g. D. E. Nichols, Halocinogens, in Pharmacology & Therapeutics 101 (2004) 131-181, J. A. Lieberman et al. Biol. Psychiatry 44 (1998) 1099-1117, S. Miyamoto et al., Mol. Psychiatry. 10 (2005), 79-104).

The subject treated in the present methods is generally a mammal, preferably a human being, male or female, in whom potentiation of metabotropic glutamate receptor activity is desired. The term "therapeutically effective amount" means the amount of the subject compound that will elicit the biological or medical response of a tissue, system, animal or human that is being sought by the researcher, veterinarian, medical doctor or other clinician. It is recognized that one skilled in the art may affect the neurological and psychiatric disorders by treating a patient presently afflicted with the disorders or by prophylactically treating a patient afflicted with the disorders with an effective amount of the compound of the present invention. As used herein, the terms "treatment" and "treating" refer to all processes, wherein there may be a slowing, interrupting, arresting, controlling, or stopping of the progression of the neurological and psychiatric disorders described herein, but does not necessarily indicate a total elimination of all disorder symptoms, as well as the prophylactic therapy of the mentioned conditions, particularly in a patient who is predisposed to such disease or disorder. The term "composition" as used herein is intended to encompass a product comprising the specified ingredients in the specified amounts, as well as any product which results, directly or indirectly, from combination of the specified ingredients in the specified amounts. Such term in relation to pharmaceutical composition, is intended to encompass a product comprising the active ingredient(s), and the inert ingredient(s) that make up the carrier, as well as any product which results, directly or indirectly, from combination, complexation or aggregation of any two or more of the ingredients, or from dissociation of one or more of the ingredients, or from other types of reactions or interactions of one or more of the ingredients. Accordingly, the pharmaceutical compositions of the present invention encompass any composition made by admixing a compound of the present invention and a pharmaceutically acceptable carrier. By "pharmaceutically acceptable" it is meant the carrier, diluent or excipient must be compatible with the other ingredients of the formulation and not deleterious to the recipient thereof.

The terms "administration of and or "administering a" compound should be understood to mean providing a compound of the invention or a prodrug of a compound of the invention to the individual in need of treatment.

A preferred embodiment of the present invention provides a method for treating schizophrenia, comprising: administering to a patient in need thereof an effective amount of a compound of formula I, a N-oxide and/or a pharmaceutically acceptable salt thereof. In another preferred embodiment, the present invention provides a method for preventing or treating anxiety, comprising: administering to a patient in need thereof an effective amount of a compound of formula I, a tautomer and/or a pharmaceutically acceptable salt thereof. Particularly preferred anxiety disorders are generalized anxiety disorder, panic disorder, and obsessive compulsive disorder.

In another preferred embodiment, the present invention provides a method for treating substance-related disorders, comprising: administering to a patient in need thereof an effective amount of a compound of formula I, a tautomer and/or a pharmaceutically acceptable salt thereof. In another preferred embodiment the present invention provides a method for treating migraine, comprising: administering to a patient in need thereof an effective amount of a compound of formula I, a tautomer and/or a pharmaceutically acceptable salt thereof. In yet another preferred embodiment, the present invention provides a method for treating epilepsy, comprising: administering to a patient in need thereof an effective amount of a compound of formula I, a tautomer and/or a pharmaceutically acceptable salt thereof.

Of the neurological and psychiatric disorders associated with glutamate dysfunction which are treated according to the present invention, the treatment of schizophrenia, anxiety, depression, migraine, substance-related disorders, especially substance dependence, substance tolerance, substance withdrawal, and epilepsy are particularly preferred. Particularly preferred anxiety disorders are generalized anxiety disorder, panic disorder, and obsessive compulsive disorder.

Thus, in a preferred embodiment, the present invention provides a method for treating schizophrenia, comprising: administering to a patient in need thereof an effective amount of a compound of formula I, a tautomer and/or a pharmaceutically acceptable salt thereof. At present, the fourth edition of the Diagnostic and Statistical Manual of Mental Disorders (DSM-IV) (1994, American Psychiatric Association, Washington, D.C.), provides a diagnostic tool including schizophrenia and other psychotic disorders. These include: disorders having psychotic symptoms as the defining feature. The term psychotic refers to delusions, prominent hallucinations, disorganized speech, disorganized or catatonic behavior. The disorder includes: paranoid, disorganized, catatonic, undifferentiated, and residual schizophrenia, schizophreniform disorder, schizoaffective disorder, delusional disorder, brief psychotic disorder, shared psychotic disorder, psychotic disorder due to a general medical condition, substance-induced psychotic disorder, and psychotic disorder not otherwise specified. The skilled artisan will recognize that there are alternative nomenclatures, nosologies, and classification systems for neurological and psychiatric disorders, and particular schizophrenia, and that these systems evolve with medical scientific progress. Thus, the term "schizophrenia" is intended to include like disorders that are described in other diagnostic sources.

In another preferred embodiment, the present invention provides a method for treating anxiety, comprising: administering to a patient in need thereof an effective amount of a compound of formula I, a tautomer and/or a pharmaceutically acceptable salt thereof. At present, the fourth edition of the Diagnostic and Statistical Manual of Mental Disorders (DSM-IV) (1994, American Psychiatric Association, Washington, D.C.), provides a diagnostic tool including anxiety and related disorders. These include: panic disorder with or without agoraphobia, agoraphobia without history of panic disorder, specific phobia, social phobia, obsessive-compulsive disorder, post-traumatic stress disorder, acute stress disorder, generalized anxiety disorder, anxiety disorder due to a general medical condition, substance-induced anxiety disorder and anxiety disorder not otherwise specified. As used herein the term "anxiety" includes treatment of those anxiety disorders and related disorder as described in the DSM-IV. The skilled artisan will recognize that there are alternative nomenclatures, nosologies, and classification systems for neurological and psychiatric disorders, and particular anxiety, and that these systems evolve with medical scientific progress. Thus, the term "anxiety" is intended to include like disorders that are described in other diagnostic sources.

In another preferred embodiment, the present invention provides a method for treating depression, comprising: administering to a patient in need thereof an effective amount of a compound of formula I, a N-oxide and/or a pharmaceutically acceptable salt thereof. At present, the fourth edition of the Diagnostic and Statistical Manual of Mental Disorders (DSM-IV) (1994, American Psychiatric Association, Washington, D.C.), provides a diagnostic tool including depression and related disorders. Depressive disorders include, for example, single episodic or recurrent major depressive disorders, and dysthymic disorders, depressive neurosis, and neurotic depression; melancholic depression including anorexia, weight loss, insomnia and early morning waking, and psychomotor retardation; atypical depression (or reactive depression) including increased appetite, hypersomnia, psychomotor agitation or irritability, anxiety and phobias; seasonal affective disorder; or bipolar disorders or manic depression, for example, bipolar I disorder, bipolar II disorder and cyclothymic disorder. As used herein the term "depression" includes treatment of those depression disorders and related disorder as described in the DSM-1V.

In another preferred embodiment, the present invention provides a method for treating substance-related disorders, especially substance dependence, substance abuse, substance tolerance, and substance withdrawal, comprising: administering to a patient in need thereof an effective amount of a compound of formula I, a tautomer and/or a pharmaceutically acceptable salt thereof. At present, the fourth edition of the Diagnostic and Statistical Manual of Mental Disorders (DSM-IV) (1994, American Psychiatric Association, Washington, D.C.), provides a diagnostic tool including disorders related to taking a drug of abuse (including alcohol), to the side effects of a medication, and to toxin exposure. Substances include alcohol, amphetamine and similarly acting sympathomimetics, caffeine, cannabis, cocaine, hallucinogens, inhalants, nicotine, opioids, phencyclidine (PCP) or similarly acting arylcyclohexylamines, and sedatives, hypnotics, or anxiolytics. Also, polysubstance dependence and other unknown substance-related disorders are included. The skilled artisan will recognize that there are alternative nomenclatures, nosologies, and classification systems for neurological and psychiatric disorders, and particular substance-related disorders, and that these systems evolve with medical scientific progress. Thus, the term "substance-related disorder" is intended to include like disorders that are described in other diagnostic sources.

In another preferred embodiment the present invention provides a method for treating migraine, comprising: administering to a patient in need thereof an effective amount of a compound of formula I, a tautomer and/or a pharmaceutically acceptable salt thereof. In one of the available sources of diagnostic tools, Dorland's Medical Dictionary (23'rd Ed., 1982, W. B. Saunders Company, Philadelphia, Pa.), migraine is defined as a symptom complex of periodic headaches, usually temporal and unilateral, often with irritability, nausea, vomiting, constipation or diarrhea, and photophobia. As used herein the term "migraine includes these periodic headaches, both temporal and unilateral, the associated irritability, nausea, vomiting, constipation or diarrhea, photophobia, and other associated symptoms. The skilled artisan will recognize that there are alternative nomenclatures, nosologies, and classification systems for neurological and psychiatric disorders, including migraine, and that these systems evolve with medical scientific progress.

In another preferred embodiment, the present invention provides a method for treating epilepsy, comprising: administering to a patient in need thereof an effective amount of a compound of formula I, a tautomer and/or a pharmaceutically acceptable salt thereof. At present, there are several types and subtypes of seizures associated with epilepsy, including idiopathic, symptomatic, and cryptogenic. These epileptic seizures can be focal (partial) or generalized. They can also be simple or complex. Epilepsy is described in the art, such as Epilepsy: A comprehensive textbook. Ed. by Jerome Engel, Jr. and Timothy A. Pedley (Lippincott-Raven, Philadelphia, 1997). At present, the International Classification of Diseases, Ninth Revision, (ICD-9) provides a diagnostic tool including epilepsy and related disorders. These include: generalized nonconvulsive epilepsy, generalized convulsive epilepsy, petit mal status epilepticus, grand mal status epilepticus, partial epilepsy with impairment of consciousness, partial epilepsy without impairment of consciousness, infantile spasms, epilepsy partialis continua, other forms of epilepsy, epilepsy, unspecified, NOS. As used herein the term "epilepsy" includes these all types and subtypes. The skilled artisan will recognize that there are alternative nomenclatures, nosologies, and classification systems for neurological and psychiatric disorders, including epilepsy, and that these systems evolve with medical scientific progress.

In the treatment, prevention, control, amelioration, or reduction of risk of conditions which require potentiation of metabotorpic glutamate receptor activity an appropriate dosage level will generally be about 0.01 to 500 mg per kg patient body weight per day which can be administered in single or multiple doses. Preferably, the dosage level will be about 0.1 to about 250 mg/kg per day; more preferably about 0.5 to about 100 mg/kg per day. A suitable dosage level may be about 0.01 to 250 mg/kg per day, about 0.05 to 100 mg/kg per day, or about 0.1 to 50 mg/kg per day. Within this range the dosage may be 0.05 to 0.5, 0.5 to 5 or 5 to 50 mg/kg per day. For oral administration, the compositions are preferably provided in the form of tablets containing 1.0 to 1000 milligrams of the active ingredient, particularly 1.0, 5.0, 10.0, 15.0, 20.0, 25.0, 50.0, 75.0, 100.0, 150.0, 200.0, 250.0, 300.0, 400.0, 500.0, 600.0, 750.0, 800.0, 900.0, and 1000.0 milligrams of the active ingredient for the symptomatic adjustment of the dosage to the patient to be treated. The compounds may be administered on a regimen of 1 to 4 times per day, preferably once or twice per day. When treating, preventing, controlling, ameliorating, or reducing the risk of neurological and psychiatric disorders associated with glutamate dysfunction or other diseases for which compounds of the present invention are indicated, generally satisfactory results are obtained when the compounds of the present invention are administered at a daily dosage of from about 0.1 milligram to about 100 milligram per kilogram of animal body weight, preferably given as a single daily dose or in divided doses two to six times a day, or in sustained release form. For most large mammals, the total daily dosage is from about 1.0 milligrams to about 1000 milligrams, preferably from about 1 milligram to about 50 milligrams, hi the case of a 70 kg adult human, the total daily dose will generally be from about 7 milligrams to about 350 milligrams. This dosage regimen may be adjusted to provide the optimal therapeutic response. It will be understood, however, that the specific dose level and frequency of dosage for any particular patient may be varied and will depend upon a variety of factors including the activity of the specific compound employed, the metabolic stability and length of action of that compound, the age, body weight, general health, sex, diet, mode and time of administration, rate of excretion, drug combination, the severity of the particular condition, and the host undergoing therapy.

The compounds according to the present invention are further useful in a method for the prevention, treatment, control, amelioration, or reduction of risk of the aforementioned diseases, disorders and conditions in combination with other agents, including an mGluR agonist.

The term "potentiated amount" refers to an amount of an mGluR agonist, that is, the dosage of agonist which is effective in treating the neurological and psychiatric disorders described herein when administered in combination with an effective amount of a compound of the present invention. A potentiated amount is expected to be less than the amount that is required to provide the same effect when the mGluR agonist is administered without an effective amount of a compound of the present invention.

A potentiated amount can be readily determined by the attending diagnostician, as one skilled in the art, by the use of conventional techniques and by observing results obtained under analogous circumstances. In determining a potentiated amount, the dose of an mGluR agonist to be administered in combination with a compound of formula I, a number of factors are considered by the attending diagnostician, including, but not limited to: the mGluR agonist selected to be administered, including its potency and selectivity; the compound of formula I to be coadministered; the species of mammal; its size, age, and general health; the specific disorder involved; the degree of involvement or the severity of the disorder; the response of the individual patient; the modes of administration; the bioavailability characteristics of the preparations administered; the dose regimens selected; the use of other concomitant medication; and other relevant circumstances.

A potentiated amount of an mGluR agonist to be administered in combination with an effective amount of a compound of formula I is expected to vary from about 0.1 milligram per kilogram of body weight per day (mg/kg/day) to about 100 mg/kg/day and is expected to be less than the amount that is required to provided the same effect when administered without an effective amount of a compound of formula I. Preferred amounts of a co-administered mGlu agonist are able to be determined by one skilled in the art. The compounds of the present invention may be used in combination with one or more other drugs in the treatment, prevention, control, amelioration, or reduction of risk of diseases or conditions for which compounds of Formula I or the other drugs may have utility, where the combination of the drugs together are safer or more effective than either drug alone. Such other drug(s) may be administered, by a route and in an amount commonly used therefore, contemporaneously or sequentially with a compound of Formula I. When a compound of formula I is used contemporaneously with one or more other drugs, a pharmaceutical composition in unit dosage form containing such other drugs and the compound of formula I is preferred. However, the combination therapy may also include therapies in which the compound of formula I and one or more other drugs are administered on different overlapping schedules. It is also contemplated that when used in combination with one or more other active ingredients, the compounds of the present invention and the other active ingredients may be used in lower doses than when each is used singly. Accordingly, the pharmaceutical compositions of the present invention include those that contain one or more other active ingredients, in addition to a compound of formula I. The above combinations include combinations of a compound of the present invention not only with one other active compound, but also with two or more other active compounds.

Likewise, compounds of the present invention may be used in combination with other drugs that are used in the prevention, treatment, control, amelioration, or reduction of risk of the diseases or conditions for which compounds of the present invention are useful. Such other drugs may be administered, by a route and in an amount commonly used therefore, contemporaneously or sequentially with a compound of the present invention. When a compound of the present invention is used contemporaneously with one or more other drugs, a pharmaceutical composition containing such other drugs in addition to the compound of the present invention is preferred. Accordingly, the pharmaceutical compositions of the present invention include those that also contain one or more other active ingredients, in addition to a compound of the present invention.

The weight ratio of the compound of the compound of the present invention to the second active ingredient may be varied and will depend upon the effective dose of each ingredient. Generally, an effective dose of each will be used. Thus, for example, when a compound of the present invention is combined with another agent, the weight ratio of the compound of the present invention to the other agent will generally range from about 1000:1 to about 1:1000, preferably about 200:1 to about 1:200. Combinations of a compound of the present invention and other active ingredients will generally also be within the aforementioned range, but in each case, an effective dose of each active ingredient should be used. In such combinations the compound of the present invention and other active agents may be administered separately or in conjunction. In addition, the administration of one element may be prior to, concurrent to, or subsequent to the administration of other agent(s).

The compounds of the present invention may be administered by conventional routes of administration, including parenteral (e.g., intramuscular, intrapentoneal, intravenous, ICV, intracisternal injection or infusion, subcutaneous injection, or implant), by inhalation spray, nasal, vaginal, rectal, sublingual, or topical routes of administration.

The compounds of the present invention may be formulated alone or together with further active compounds, in suitable dosage unit formulations containing conventional non-toxic pharmaceutically excipients. Excipients can be solid, semisolid or liquid materials which serve as vehicles, carriers or medium for the active compound. Suitable excipients are listed in the specialist medicinal monographs. In addition, the formulations can comprise pharmaceutically acceptable carriers or customary auxiliary substances, such as glidants; wetting agents; emulsifying and suspending agents; preservatives; antioxidants; antiirritants; chelating agents; coating auxiliaries; emulsion stabilizers; film formers; gel formers; odor masking agents; taste corrigents; resin; hydrocolloids; solvents; solubilizers; neutralizing agents; diffusion accelerators; pigments; quaternary ammonium compounds; refatting and overfatting agents; raw materials for ointments, creams or oils; silicone derivatives; spreading auxiliaries; stabilizers; sterilants; suppository bases; tablet auxiliaries, such as binders, fillers, glidants, disintegrants or coatings; propellants; drying agents; opacifiers; thickeners; waxes; plasticizers and white mineral oils. A formulation in this regard is based on specialist knowledge as described, for example, in Fiedler, H. P., Lexikon der Hilfsstoffe für Pharmazie, Kosmetik and angrenzende Gebiete [Encyclopedia of auxiliary substances for pharmacy, cosmetics and related fields], $4^{th}$ edition, Aulendorf: ECV-Editio-Kantor-Verlag, 1996.

Examples of suitable pharmaceutical formulations are solid medicinal forms, such as powders, granules, tablets, in particular film tablets, lozenges, sachets, cachets, sugar-coated tablets, capsules, such as hard gelatin capsules and soft gelatin capsules, suppositories or vaginal medicinal forms, semisolid medicinal forms, such as ointments, creams, hydrogels, pastes or plasters, and also liquid medicinal forms, such as solutions, emulsions, in particular oil-in-water emulsions, suspensions, for example lotions, injection preparations and infusion preparations, and eyedrops and eardrops. Implanted release devices can also be used for administering inhibitors according to the invention. In addition, it is also possible to use liposomes or microspheres.

When producing the compositions, the compounds according to the invention are optionally mixed or diluted with one or more excipients.

The following examples are intended for further illustration of the present invention.

PREPARATION EXAMPLES

Abbreviations used in the Examples that follow are: Ac acetate, BINAP 2,2'-bis(diphenylphosphino)-1,1'-binaphthyl, dba dibenzylideneacetone, HPLC high performance liquid chromatography, NMP N-methylpyrrolidone.

Example 1

2-butyl-5-(4-phenylpyridin-3-ylamino)isoindolin-1-one

3-Bromo-4-phenylpyridine (125 mg, 0.534 mmol) was added to a suspension of 2,2'-bis(diphenylphosphino)-1,1'-binaphthyl (BINAP) (33 mg, 0.053 mmol) and tris(dibenzylideneacetone)dipalladium(0) ($Pd_2(dba)_3$) (49 mg, 0.053 mmol) in toluene (5 mL). 5-Amino-2-butylisoindolin-1-one (120 mg, 0.587 mmol) and sodium tert-butoxide (128 mg, 1.335 mmol) were added and the mixture was stirred and heated in the microwave (120° C., 300 W, 75 min). Water and ethyl acetate were added, the organic layer was separated and the aqueous layer was extracted with ethyl acetate. The combined organic layers were washed with water and dried over MgSO$_4$. Purification by flash chromatography (dichloromethane/methanol, gradient 1-5% methanol) provided 2-butyl-5-(4-phenylpyridin-3-ylamino)isoindolin-1-one (56 mg, 46%). ESI-MS [M+H]$^+$=358.2.

Example 2

2-butyl-5-(5-phenylpyridin-3-ylamino)isoindolin-1-one

5-Bromo-2-butylisoindolin-1-one (71.6 mg, 0.267 mmol), 5-phenylpyridin-3-amine (50.0 mg, 0.294 mmol) and Cs$_2$CO$_3$ (217.0 mg, 0.668 mmol) were added to suspension of 2-dicyclohexylphosphino-2',4',6'-triisopropylbiphenyl (X-Phos) (12.7 mg, 0.027 mmol) and palladium acetate (PdOAc$_2$) (8.0 mg, 0.040 mmol) in toluene (2 mL). The mixture was stirred and heated in the microwave (120° C., 300 W, 60 min). Water and ethyl acetate were added. The organic layer was separated, the aqueous layer was extracted with ethyl acetate and the combined organic layers were dried over MgSO$_4$. Purification by flash chromatography (dichloromethane/methanol, gradient 1-5% methanol) provided 2-butyl-5-(5-phenylpyridin-3-ylamino)isoindolin-1-one (53 mg, 54%). ESI-MS [M+H]$^+$=358.1.

Example 3

2-butyl-5-(4-phenylpyridin-3-yloxy)isoindolin-1-one

A mixture of 3-bromo-4-phenylpyridine (50 mg, 0.213 mmol), 2-butyl-5-hydroxy-isoindolin-1-one (88 mg, 0.427 mmol), Cs$_2$CO$_3$ (139 mg, 0.427 mmol), CuI (16.3 mg, 0.085 mmol) and 2,2,6,6-tetramethyl-3.5-heptanedione (53 μL, 0.256 mmol) in degassed N-methylpyrrolidone (NMP) (2 mL) was stirred and heated in the microwave (220° C., 300 W, 30 min). Two of those reactions were combined, excess water and ethyl acetate were added. The organic layer was separated and the aqueous layer was extracted with ethyl acetate. The combined organic layers were extracted with aqueous HCl (2 M) and the combined extracts were basified with aqueous NaOH (2 M) followed by extraction with ethyl acetate. The combined organic layers were washed with water and dried over MgSO$_4$. Purification by HPLC provided 2-butyl-5-(4-phenylpyridin-3-yloxy)isoindolin-1-one (16 mg, 8%).
ESI-MS [M+H]$^+$=359.1.

The following examples 4 to 18 have been prepared in a similar way:

Example 4

2-butyl-7-chloro-5-[(5-phenylpyridin-3-yl)amino]-2,3-dihydro-1H-isoindol-1-one

ESI-MS: [M+H]$^+$=392.10;
$^1$H NMR (chloroform-d, 500 MHz): δ ppm 8.56 (d, J=1.8 Hz, 1 H), 8.47 (d, J=2.4 Hz, 1 H), 7.67 (d, J=2.1 Hz, 1 H), 7.55-7.60 (m, 2 H), 7.49 (t, J=7.5 Hz, 2 H), 7.43 (m, 1 H), 6.95-7.04 (m, 2 H), 6.30 (s, 1 H), 4.25 (s, 2 H), 3.56 (t, J=7.3 Hz, 2 H), 1.57-1.67 (m, 2 H), 1.37 (m, 2 H), 0.94 (t, J=7.3 Hz, 3 H).

Example 5

2-butyl-5-{[5-(piperazin-1-yl)pyridin-3-yl]amino}-2,3-dihydro-1H-isoindol-1-one

ESI-MS: [M+H]$^+$=366.25;
$^1$H NMR (DMSO-d$_6$, 500 MHz): δ ppm 8.59 (s, 1 H), 7.88 (d, J=2.1 Hz, 2 H), 7.50 (d, J=8.2 Hz, 1 H), 7.17 (s, 1 H), 7.06 (dd, J=8.4, 1.7 Hz, 1 H), 6.86-7.02 (m, 1 H), 4.35 (s, 2 H), 2.99-3.14 (m, 4 H), 2.74-2.94 (m, 4 H), 1.54 (quin, J=7.3 Hz, 2 H), 1.26 (sxt, J=7.4 Hz, 2 H), 0.89 (t, J=7.3 Hz, 3 H).

Example 6

2-butyl-5-{[2-chloro-5-(piperazin-1-yl)pyridin-3-yl]amino}-2,3-dihydro-1H-isoindol-1-one ESI-MS: [M+H]$^+$=400.20;
$^1$H NMR (DMSO-d$_6$, 500 MHz): δ ppm 8.15 (s, 1 H), 7.77 (d, J=2.7 Hz, 1 H), 7.50 (d, J=7.9 Hz, 1 H), 7.20 (d, J=2.4 Hz, 1 H), 7.02-7.09 (m, 2 H), 4.34 (s, 2 H), 3.43-3.48 (m, 2 H), 3.01-3.10 (m, 4 H), 2.80 (d, J=4.6 Hz, 4 H), 1.54 (quin, J=7.2 Hz, 2 H), 1.27 (dq, J=14.8, 7.3 Hz, 2 H), 0.89 (t, J=7.3 Hz, 3 H).

Example 7

2-butyl-5-[(5-chloropyridin-3-yl)amino]-2,3-dihydro-1H-isoindol-1-one

ESI-MS: [M+H]$^+$=316.10;
$^1$H NMR (DMSO-d$_6$, 400 MHz): δ ppm 8.97 (s, 1 H), 8.37 (d, J=2.4 Hz, 1 H), 8.11 (d, J=2.0 Hz, 1 H), 7.53-7.64 (m, 2 H), 7.28-7.34 (s, 1 H), 7.15 (dd, J=8.3, 2.0 Hz, 1 H), 4.40 (s, 2 H), 3.47 (t, J=7.1 Hz, 2 H), 1.57 (quin, J=7.3 Hz, 2 H), 1.29 (dq, J=14.9, 7.3 Hz, 2 H), 0.91 (t, J=7.5 Hz, 3 H).

Example 8

2-butyl-5-{[5-(morpholin-4-yl)pyridin-3-yl]amino}-2,3-dihydro-1H-isoindol-1-one

ESI-MS: [M+H]$^+$=367.10;
$^1$H NMR (DMSO-d$_6$, 400 MHz): δ ppm 8.60 (s, 1 H), 7.93 (d, J=2.4 Hz, 2 H), 7.49 (d, J=8.3 Hz, 1 H), 7.19 (s, 1 H), 7.05-7.08 (m, 1 H), 7.02 (t, J=2.3 Hz, 1 H), 4.35 (s, 2 H), 3.72-3.77 (m, 4 H), 3.45 (t, J=7.1 Hz, 2 H), 3.11-3.16 (m, 4 H), 1.55 (quin, J=7.2 Hz, 2 H), 1.28 (dq, J=7.6 Hz, 2 H), 0.91 (t, J=7.3 Hz, 3 H).

Example 9

2-butyl-5-{[2-chloro-5-(4-methylpiperazin-1-yl)pyridin-3-yl]amino}-2,3-dihydro-1H-isoindol-1-one ESI-MS: [M+H]$^+$=414.20;
$^1$H NMR (DMSO-d$_6$, 500 MHz): δ ppm 8.21 (s, 1 H), 7.81 (d, J=2.7 Hz, 1 H), 7.50 (d, J=7.9 Hz, 1 H), 7.25 (d, J=2.7 Hz, 1 H), 7.03-7.13 (m, 2 H), 4.36 (s, 2 H), 3.46 (t, J=7.2 Hz, 2 H), 3.08-3.22 (m, 4 H), 2.37-2.46 (m, 4 H), 2.20 (s, 3 H), 1.55 (quin, J=7.2 Hz, 2 H), 1.21-1.35 (m, 2 H), 0.91 (t, J=7.5 Hz, 3 H).

Example 10

2-butyl-5-{[5-(4-methylpiperazin-1-yl)pyridin-3-yl]amino}-2,3-dihydro-1H-isoindol-1-one $^1$H NMR (DMSO-d$_6$, 500 MHz): δ=8.63 (s, 1 H), 7.92 (d, 2 H), 7.50 (d, J=8.2 Hz, 1 H), 7.19 (s, 1 H), 7.07 (dd, J=8.4, 1.7

Hz, 1 H), 7.01 (t, J=2.3 Hz, 1 H), 4.36 (s, 2 H), 3.46 (t, J=7.2 Hz, 2 H), 3.07-3.22 (m, 4 H), 2.45 (d, J=4.9 Hz, 4 H), 2.22 (s, 3 H), 1.48-1.64 (m, 2 H), 1.18-1.35 (m, 2 H), 0.91 (t, J=7.3 Hz, 3 H).

Example 11

2-butyl-5-[(5-phenylpyridin-3-yl)oxy]-2,3-dihydro-1H-isoindol-1-one

ESI-MS: [M+H]$^+$=359.10.

Example 12

2-butyl-4-[(5-phenylpyridin-3-yl)oxy]-2,3-dihydro-1H-isoindol-1-one trifluoroacetate ESI-MS: [M+H]$^+$=359.10;
$^1$H NMR (500 MHz, DMSO) δ ppm 8.80 (s, 1H), 8.49 (s, 1H), 7.92 (t, J=2.1, 1H), 7.75 (t, J=10.4, 2H), 7.57-7.39 (m, 5H), 7.23 (dd, J=2.4, 6.4, 1H), 4.46 (s, J=46.1, 2H), 3.50 (t, J=7.2, 2H), 1.61-1.50 (m, 2H), 1.32-1.20 (m, 2H), 0.87 (t, J=7.4, 3H).

Example 13

2-butyl-5-[(5-phenylpyridin-3-yl)oxy]-3,4-dihydroisoquinolin-1(2H)-one trifluoroacetate ESI-MS: [M+H]$^+$=373.20;
$^1$H NMR (500 MHz, DMSO) δ ppm 8.72 (s, 1H), 8.35 (s, 1H), 7.74 (m, 4H), 7.53-7.35 (m, 4H), 7.23 (d, J=8.0, 1H), 3.50 (m, 4H), 2.92 (t, J=6.6, 2H), 1.58-1.47 (m, 2H), 1.35-1.23 (m, 2H), 0.89 (t, J=7.4, 3H).

Example 14

2-butyl-6-[(5-phenylpyridin-3-yl)oxy]-3,4-dihydroisoquinolin-1(2H)-one trifluoroacetate ESI-MS: [M+H]$^+$=373.20;
$^1$H NMR (500 MHz, DMSO) δ ppm 8.81 (s, 1H), 8.46 (d, J=2.1, 1H), 7.95-7.85 (m, 2H), 7.80-7.72 (m, 2H), 7.47 (m, 3H), 7.08-6.96 (m, 2H), 3.47 (dt, J=6.9, 14.5, 4H), 2.93 (t, J=6.5, 2H), 1.56-1.45 (m, 2H), 1.34-1.21 (m, 2H), 0.89 (t, J=7.4, 3H).

Example 15

2-butyl-6-[(5-phenylpyridin-3-yl)oxy]-2,3-dihydro-1H-isoindol-1-one trifluoroacetate ESI-MS: [M+H]$^+$=359.10;
$^1$H NMR (500 MHz, DMSO) δ ppm 8.80 (s, 1H), 8.46 (s, 1H), 7.89 (s, 1H), 7.74 (d, J=7.2, 2H), 7.64 (d, J=8.2, 1H), 7.53-7.36 (m, 4H), 7.31 (d, J=2.3, 1H), 4.45 (s, 2H), 3.49 (t, J=7.2, 2H), 1.62-1.49 (m, 2H), 1.32-1.20 (m, 2H), 0.88 (t, J=7.4, 3H).

Example 16

2-butyl-5-(6-phenyl-pyrazin-2-ylamino)-2,3-dihydro-iso-indol-1-one

ESI-MS: [M+H]$^+$=359.10.

Example 17

2-butyl-5-(quinolin-3-ylamino)-2,3-dihydro-1H-isoindol-1-one

ESI-MS: [M+H]$^+$=332.10;
$^1$H NMR (chloroform-d, 500 MHz): δ ppm 8.78 (d, J=2.7 Hz, 1 H), 8.04 (d, J=8.5 Hz, 1 H), 7.85 (d, J=2.4 Hz, 1 H), 7.76 (d, J=7.9 Hz, 1 H), 7.70 (d, J=7.9 Hz, 1 H), 7.59 (td, J=7.6, 1.4 Hz, 1 H), 7.50-7.54 (m, 1 H), 7.13-7.19 (m, 2 H), 6.53 (br. s., 1 H), 4.32 (s, 2 H), 3.60 (t, J=7.3 Hz, 2 H), 1.60-1.68 (m, 2 H), 1.34-1.42 (m, 2 H), 0.95 (t, J=7.5 Hz, 3 H).

Example 18

2-butyl-5-(quinoxalin-2-ylamino)-2,3-dihydro-1H-isoindol-1-one

ESI-MS: [M+H]$^+$=333.10;
$^1$H NMR (DMSO-d$_6$, 500 MHz): δ ppm 10.29 (s, 1 H), 8.62 (s, 1 H), 8.42 (s, 1 H), 7.87-7.93 (m, 2 H), 7.78-7.83 (m, 1 H), 7.63-7.72 (m, 2 H), 7.49-7.54 (m, 1 H), 4.49 (s, 2 H), 3.50 (t, J=7.2 Hz, 2 H), 1.59 (quin, J=7.3 Hz, 2 H), 1.30 (sxt, J=7.3 Hz, 2 H), 0.92 ppm (t, J=7.5 Hz, 3 H).

Example 19

2-(2-methoxyethyl)-5-[(5-phenylpyridin-3-yl)amino]-2,3-dihydro-1H-isoindol-1-one

ESI-MS: [M+H]$^+$=360.10.

Example 20

2-butyl-5-[(2-chloropyridin-3-yl)amino]-2,3-dihydro-1H-isoindol-1-one $^1$H NMR (DMSO-d$_6$, 500 MHz): δ=7.98 (m, 1 H), 7.80 (d, 1 H), 7.64 (d, 1 H), 7.20 (s, 1 H), 7.16-7.19 (m, 2 H), 6.32 (br. s., 1 H), 4.35 (s, 2 H), 3.61 (t, J=7.3 Hz, 2 H), 1.65 (quint, 2 H), 1.39 (m sym., 2 H), 0.96 (t, J=7.3 Hz, 3 H).

Example 21

2-butyl-5-{[2-chloro-5-(piperazin-1-yl)pyridin-3-yl]oxy}-3,4-dihydroisoquinolin-1(2H)-one

ESI-MS: [M+H]$^+$=415.20.

Example 22

2-butyl-5-{[2-chloro-5-(4-methylpiperazin-1-yl)pyridin-3-yl]oxy}-3,4-dihydroisoquinolin-1(2H)-one

ESI-MS: [M+H]$^+$=429.20.

Example 23

2-butyl-5-[(5-phenylpyridin-3-yl)methyl]-2,3-dihydro-1H-isoindol-1-one

Dioxane (5 mL) was added to a solution of sodium phosphate (77 mg, 0.365 mmol) in water (0.5 ml). 3-(Bromomethyl)-5-phenylpyridine hydrobromide (50 mg, 0.152 mmol, described in BMCL 2001, 11(17), 2345-9), 2-butyl-1-oxoisoindolin-5-ylboronic acid (35.4 mg, 0.152 mmol; prepared from the corresponding bromide as described in J. Med.

Chem. 2009, 52(19), 6097-106)), X-Phos (2.90 mg, 6.08 µmol) and Pd$_2$(dba)$_3$ (5.57 mg, 6.08 µmol) were added and the mixture stirred for 12 h at room temperature. The solution was dried in vacuo, the residue solved in water and extracted with ethyl acetate. The organic phase was dried on Na$_2$SO$_4$, filtrated and dried in vacuo. Purification on a column of silicagel (eluent 30:1 CH$_2$Cl$_2$: NH$_3$ (2M in EtOH)) afforded 3 mg (6% yield) of Example 23.

ESI-MS: [M+H]$^+$=357.10;
$^1$H NMR (DMSO-d$_6$, 500 MHz): δ ppm 8.74 (d, J=2.1 Hz, 1 H), 8.54 (d, J=1.8 Hz, 1 H), 7.99 (s, 1 H), 7.70 (d, J=7.0 Hz, 2 H), 7.61 (d, J=7.6 Hz, 1 H), 7.41-7.55 (m, 5 H), 4.42 (s, 2 H), 4.17 (s, 2 H), 3.48 (t, J=7.2 Hz, 2 H), 1.55 (quin, J=7.3 Hz, 2 H), 1.23-1.30 (m, 2 H), 0.89 (t, J=7.3 Hz, 3 H).

Example 24

2-butyl-5-(5-phenylpyridin-3-yl)-2,3-dihydro-1H-isoindol-1-one

ESI-MS: [M+H]$^+$=343.10;
As described for Example 23 starting from 3-bromo-5-phenylpyridine (50 mg, 0.214 mmol, commercially available) and 2-butyl-1-oxoisoindolin-5-ylboronic acid (49.8 mg, 0.214 mmol, s. above). Yield 14% (10 mg).
$^1$H NMR (500 MHz, DMSO) δ ppm 8.93 (m, 2H), 8.36 (s, 1H), 8.07 (s, 1H), 7.96 (d, J=7.9, 1H), 7.86 (d, 2H), 7.81 (d, 1H), 7.55 (t, 2H), 7.53 (t, 1H), 4.54 (s, 2H), 3.54 (t, 2H), 1.60 (quin, 2H), 1.30 (sext, 2H), 0.91 (t, J=7.4, 3H).

Biological Tests
I Generation of a HEK293 Cell Clones Permanently Expressing mGlu Receptors and Functional Evaluation of the Cells
  a) mGlu2 Receptor For the purpose of the present study, a cell line permanently expressing the human mGlu2 receptor, the rat glutamate transporter rGLAST and the alpha subunit of G16 was generated by transfection. Briefly, HEK293 cells were seeded in petri dishes (diameter 15 cm) at a density of 2×10$^6$ cells in DMEM with glutamax (Invitrogen, GIBCO #21885-025), 10% dialyzed Fetal Calf Serum (Invitrogen, Gibco #26400-044), and incubated at 37° C. over night. The following day cells were transfected with Lipofectamine (Invitrogen, Gibco #18324-012) as recommended by the manufacturer, using linearized pcDNA3.1 (V5/His)-hmGlu2 receptor (ScaI) and pcDNA3.1 Zeo-Ga16 IRES rGLAST (SspI). After transfection the cells were selected in DMEM Glutamax Medium (Invitrogen, GIBCO #21885-025), containing 10% dialyzed fetal calf serum (FCS; (Invitrogen, Gibco #26400-044), antibiotic/antimycotic, 800 µg/ml Geneticin (G418) and 250 µg/ml Zeozin. Single clones were isolated manually and further subcloned by serial dilution.

The function of the mGlu2 receptor was determined by evaluating intracellular Ca$^{2+}$ concentrations under standard conditions in a fluorometric imaging plate reader (FLIPR, Molecular Devices, Union City, Calif. 94587, USA) by measuring the response of the cells to a test compound. The FLIPR assay is a common functional assay to monitor native or recombinant Galphaq-coupled receptors, and native or recombinant receptors normally linked to other G-protein signalling cascades, which are coupled to calcium through co-expression of an alpha subunit of a promiscuous or chimeric G-protein. In the assay the increase of intracellular calcium is measured through a calcium-dependent fluorescent dye (e.g. Fluo-4 AM) in the FLIPR instrument.

For selection of a suitable cell clone and also the subsequent measurements of the selected clone, 4×10$^4$ cells/well were plated on poly-D-lysine coated Biocoat-plates multi-well 96 in DMEM Glutamax (GIBCO #21885-025)/10% dialyzed FCS over night. The following day, the medium was aspirated and exchanged for glutamate-free DMEM (Gibco #21969-035), without FCS or glutamine, containing 50 µg/ml gentamycin (Gibco #15750). Cells were again incubated over night. Before the measurement, cells were loaded with 2 µM Fluo-4 AM (Molecular Probes, F14201; stock solution 1 mM in DMSO) and 0.02% Pluronic F127 (Molecular Probes, P3000; stock solution 10% in DMSO) in DMEM medium (Gibco #21969-035) for 45 minutes at 37° C. in a final volume of 100 µl per well. Finally, the plates were washed in a BioTec cell washer with HBSS, containing 20 mM HEPES. The end-volume in each well was 100 µl. The plates were subsequently measured in a fluorometric imaging plate reader (FLIPR, Molecular Devices, Union City, Calif. 94587, USA).

The compounds of the present invention were tested in the above-described FLIPR assay using the selected cell clone. Increased intracellular calcium levels were quantified following addition of test compound (agonism), as well as following addition of a submaximal concentration of 1 micromolar (1 µM) glutamate (potentiation).

For the determination of the effect of the test compound by itself (agonism) or by increasing the response to a submaximal concentration (e.g. 1 µM) of glutamate (potentiation), the resulting signal is determined by subtraction of the background fluorescence from the maximal fluorescent peak height of the respective response. In the FLIPR instrument the compound is given to the cell and its fluorescence response quantified by the FLIPR instrument (agonism). The concentration at which the compound exerts half its maximal effect is named the 'effective concentration 50' or 'EC$_{50}$'. The maximal effect induced by the test substance is normalized to the maximal effect exerted by 100 µM glutamate (set at 100%).

Ten minutes after addition of the test compound to the plate, 1 µM glutamate is added. A potentiator enhances the response of the receptor to glutamate. The response to glutamate in the presence of test compound is quantified. The concentration at which the test compound is able to exert half its maximal potentiation effect to glutamate is named the 'EC$_{50}$'. The maximal response to 1 micromolar glutamate in the presence of test compound is normalized to the maximal effect exerted by 100 µM glutamate (set at 100%). Least squares curve fitting with a four-parameter equation is then applied to the resulting dose-response curve to determine the resulting EC$_{50}$ values (Graph Pad Prism). A control cell line, HEK293 cells expressing permanently rGLAST and Galpha16 was also plated at 4×10$^4$ cells/well for parallel testing to verify specificity of the test compound for mGlu2 receptor agonism or potentiation. The EC$_{50}$ values are given in table I.

Highly potent or key compounds were further characterized by measurement of their efficacy and potency to inhibit forskolin-induced cAMP levels in these cells on their own (agonism) or to potentiate the effect of glutamate (potentiation). Cyclic AMP levels were quantified using Alphascreen technology (PerkinElmer Life and Analytical Sciences, 710 Bridgeport Avenue, Shelton, Conn. USA) as described by the manufacturer for determining the effects of Galphai coupled receptors. The concentration at which a compound exerts half its maximal effect is named the 'effective concentration 50' or 'EC$_{50}$'. The maximal effect induced by the test substance is normalized to the maximal effect exerted by 100 µM glutamate (100%). Least squares curve fitting with a four-parameter equation is then applied to the resulting dose-response curve to determine the resulting EC$_{50}$ values (Graph Pad Prism).

The compounds of the following examples had activity in potentiating the mGlu2 receptor in the aforementioned assays, generally with an $EC_{50}$ of not more than about 10 μM. Preferred compounds within the present invention had activity in potentiating the mGlu2 receptor in the aforementioned assays with an $EC_{50}$ of less than about 1 μM. Such a result is indicative of the intrinsic activity of the compounds in use as potentiators of mGlu2 receptor activity.

TABLE I

| EXAMPLE | $EC_{50}$[1] |
|---|---|
| 4 | ++ |
| 5 | + |
| 6 | + |
| 7 | ++ |
| 8 | +++ |
| 9 | ++ |
| 10 | + |
| 11 | +++ |
| 12 | +++ |
| 13 | +++ |
| 14 | +++ |
| 15 | ++ |
| 16 | +++ |
| 17 | ++ |
| 18 | + |
| 19 | ++ |
| 20 | + |
| 21 | ++ |
| 22 | ++ |
| 23 | ++ |
| 24 | ++ |

[1]+++: $EC_{50} < 0.5$ μM ++: $0.5$ μM $\leq EC_{50} \leq 2$ μM +: $2$ μM $< EC_{50} < 10$ μM b) mGlu3 Receptor For the purpose of the present study, we generated by transfection a cell line permanently expressing the human mGlu3 receptor, the rat glutamate transporter rGLAST and the alpha subunit of G16. Briefly, HEK293 cells were seeded in petri dishes (diameter 15 cm) at a density of $2 \times 10^6$ cells in DMEM with glutamax (Invitrogen, GIBCO #21885-025), 10% dialyzed Fetal Calf Serum (Invitrogen, Gibco #26400-044), and incubated at 37° C. over night. The following day cells were transfected with Lipofectamine (Invitrogen, Gibco #18324-012) as recommended by the manufacturer, using linearized pcDNA3.1 (V5/His)-hmGlu3 receptor (ScaI) and pcDNA3.1 Zeo-Ga16 IRES rGLAST (SspI). After transfection the cells were selected in DMEM Glutamax Medium (Invitrogen, GIBCO #21885-025), containing 10% dialyzed fetal calf serum (FCS; (Invitrogen, Gibco #26400-044), antibiotic/antimycotic, 800 μg/ml Geneticin (G418) and 250 μg/ml Zeozin. Single clones were isolated manually and further subcloned by serial dilution. Function was tested with FLIPR as described above.

c) mGlu4 Receptor

For the purpose of the present study, we generated by transfection a cell line permanently expressing human mGlu4 receptor, the rat glutamate transporter rGLAST and the alpha subunit of G15. Briefly, HEK293 cells were seeded in petri dishes (diameter 15 cm) at a density of $2 \times 10^6$ cells in DMEM glutamax, 10% dialyzed FCS, and incubated at 37° C. over night. The following day cells were transfected with Lipofectamine (Invitrogen, Karlsruhe, Germany) as recommended by the manufacturer, using linearised pcDNA3-hmGlu4 (SspI) and pcDNA3.1(+) Hygro-rGLAST IRES Ga15 (SspI). After transfection the cells were cultured in DMEM Glutamax Medium (Invitrogen), containing 10% dialyzed fetal calf serum (FCS; Invitrogen), antibiotic/antimycotic, 800 μg/ml Geneticin (G418) and 150 μg/ml Hygromycin, and single clones were isolated manually and subcloned by serial dilution. Function was tested with FLIPR as described above.

d) mGlu7 Receptor

For the purpose of the present study, we generated by transfection a cell line permanently expressing human mGlu7a receptor, the rat glutamate transporter rGLAST and the alpha subunit of G15. Briefly, HEK293 cells were seeded in petri dishes (diameter 15 cm) at a density of $2 \times 10^6$ cells in DMEM glutamax, 10% dialyzed FCS, and incubated at 37° C. over night. The following day cells were transfected with Lipofectamine (Invitrogen, Karlsruhe, Germany) as recommended by the manufacturer, using linearised pcDNA3(−)-hmGlu7a (SspI). After transfection cells were cultured in DMEM Glutamax Medium (Invitrogen), containing 10% dialyzed fetal calf serum (FCS; Invitrogen), antibiotic/antimycotic (Invitrogen) and 800 μg/ml Geneticin (G418). Single clones were isolated manually, tested for reduction of cellular cAMP (alpha screen) and subcloned by FACS. Single cell clones were retested for cAMP reduction, and transfected with pcDNA3.1 (+) Hygro rGLAST IRES Ga15 (SspI). The transfection was done identical as described above. Cells were selected in DMEM Glutamax, 10% dialyzed FCS, antibiotic/antimycotic, 800 μg/ml G418 and 150 μg/ml Hygromycin. Single clones were isolated by serial dilution and tested by FLIPR as described above.

e) mGlu1 and 5 Receptors

For the purpose of the present study, we generated by transfection a cell line permanently expressing human mGlu5a and the rat glutamate transporter rGLAST. Briefly, cells were transfected with Lipofectamine (Invitrogen, Karlsruhe, Germany), using linearised pcDNA3-hmGlu5a (ScaI) and pIRES-rGlast (SspI). After transfection the cells were cultured in DMEM Glutamax Medium (Invitrogen), containing 10% dialyzed fetal calf serum (FCS; Invitrogen), antibiotic/antimycotic, 800 μg/ml Geneticin (G418) and 150 μg/ml Hygromycin, and single clones were isolated manually. Identically, a cell line expressing mGlu1a was generated. Functional clones were selected using intracellular $Ca^{2+}$ measurements with a fluorescence imaging plate reader (FLIPR) under standard conditions as described above.

We claim:
1. A compound of formula I

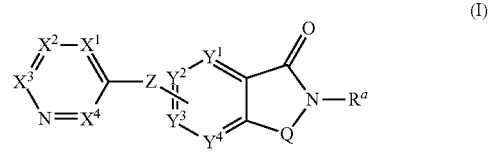

wherein
$X^1$ is N or C-$R^1$
$X^2$ is N or C-$R^2$
$X^3$ is N or C-$R^3$
$X^4$ is N or C-$R^4$
provided that none or one of $X^1$, $X^2$, $X^3$ or $X^4$ is N;
$Y^1$ is N, C or C-$R^5$
$Y^2$ is N, C or C-$R^6$
$Y^3$ is N, C or C-$R^7$
$Y^4$ is N, C or C-$R^8$
provided that only the moiety $Y^1$, $Y^2$, $Y^3$ or $Y^4$ to which Z is bound is C and further provided that 0, or 1 of $Y^1$, $Y^2$, $Y^3$ or $Y^4$ is N;
Z is $CR^{Za}R^{Zb}$, O, S, S(O), S(O)$_2$ or $NR^{Zc}$;

$R^{Za}$, $R^{Zb}$ are independently of each other selected from hydrogen, halogen and $C_1$-$C_4$-alkyl;

$R^{Zc}$ is hydrogen, $C_1$-$C_4$-haloalkyl, $C_3$-$C_6$-cycloalkyl, $C_3$-$C_6$-cycloalkylmethyl, or $C_1$-$C_4$-alkyl, which is unsubstituted or carries one radical selected from $C_1$-$C_4$-alkoxy and $NR^{Z1}R^{Z2}$;

where $R^{Z1}$ and $R^{Z2}$ are independently of each other selected from hydrogen, $C_3$-$C_6$-cycloalkyl, $C_3$-$C_6$-cycloalkylmethyl, $C_1$-$C_4$-alkyl and $C_1$-$C_4$-alkoxy-$C_1$-$C_4$-alkyl, or $R^{Z1}$ and $R^{Z2}$ together with the nitrogen to which they are attached form a 5- or 6-membered N-bound saturated heterocycle, which, in addition to the nitrogen atom, may comprise a further heteroatom, selected from O, S and N, as ring member and which is unsubstituted or carries 1, 2, 3 or 4 $C_1$-$C_4$-alkyl radicals;

or $R^{Zc}$ is a radical $S(O)_2R^{Z3}$ or a radical $S(O)_2NR^{Z4}R^{Z5}$;

where $R^{Z3}$ is $C_1$-$C_4$-alkyl, $C_1$-$C_4$-alkoxy-$C_1$-$C_4$-alkyl, $C_1$-$C_4$-haloalkyl, $C_3$-$C_6$-cycloalkyl, $C_3$-$C_6$-cycloalkylmethyl, phenyl or benzyl, wherein the phenyl ring in the last two mentioned radicals itself is unsubstituted or carries 1, 2, 3, 4 or 5 identical or different radicals selected from halogen, $C_1$-$C_4$-alkyl, $C_1$-$C_4$-haloalkyl, $C_1$-$C_4$-alkoxy and $C_1$-$C_4$-haloalkoxy;

$R^{Z4}$ and $R^{Z5}$ have one of the meanings given for $R^{Z3}$ or $R^{Z4}$ and $R^{Z5}$ together with the nitrogen to which they are attached form a 5- or 6-membered N-bound saturated heterocycle, which, in addition to the nitrogen atom, may comprise a further heteroatom, selected from O, S and N as ring member and which is unsubstituted or carries 1, 2, 3 or 4 $C_1$-$C_4$-alkyl radicals;

Q is $CH_2$ or $CH_2CH_2$, where one or two of the hydrogen atoms in $CH_2$ or $CH_2CH_2$ may be replaced by halogen, $C_1$-$C_4$-alkyl or $C_1$-$C_4$-haloalkyl;

$R^1$ is selected from hydrogen, halogen, $C_1$-$C_6$-alkyl, which is unsubstituted or carries one $C_1$-$C_4$-alkoxy radical, $C_1$-$C_6$-haloalkyl, $C_1$-$C_6$-alkoxy, $C_1$-$C_4$-haloalkoxy, $C_3$-$C_8$-cycloalkyl, a radical $NR^{1a}R^{1b}$, a radical $CH_2NR^{1a}R^{1b}$, C-bound 3- to 10-membered, saturated heterocyclyl having 1 or 2 nitrogen atoms and 0 or 1 heteroatoms, selected from O and S, as ring members, aryl, aryl-$CH_2$, aryloxy, hetaryl, hetaryloxy or hetaryl-$CH_2$, wherein the aryl, heterocyclyl and hetaryl rings ring in the last seven radicals themselves are unsubstituted or carry 1, 2, 3, 4 or 5 identical or different radicals $R^{1c}$;

$R^{1a}$ is hydrogen, $C_1$-$C_8$-alkyl, $C_1$-$C_8$-haloalkyl, $C_1$-$C_4$-alkoxy-$C_1$-$C_4$-alkyl, $C_3$-$C_8$-cycloalkyl, $C_1$-$C_8$-alkylcarbonyl, $C_1$-$C_8$-alkoxycarbonyl, benzyl, phenyl or 5- or 6-membered hetaryl, wherein the phenyl and hetaryl rings in the last three radicals itself are unsubstituted or carry 1, 2, 3, 4 or 5 identical or different radicals $R^{1c}$;

$R^{1b}$ is hydrogen or $C_1$-$C_4$-alkyl; or $NR^{1a}R^{1b}$ is a 5- to 10-membered mono- or bicyclic N-bound saturated heterocycle, which, in addition to the nitrogen atom, may comprise a further heteroatom, selected from O, S and N as ring member and which is unsubstituted or carries 1, 2, 3 or 4 $C_1$-$C_4$-alkyl radicals;

$R^{1c}$ is selected from the group consisting of halogen, CN, OH, $C_1$-$C_4$-alkyl, $C_3$-$C_6$-cycloalkyl, $C_1$-$C_4$-haloalkyl, $C_1$-$C_4$-alkoxy and $C_1$-$C_4$-haloalkoxy;

$R^2$ is selected from hydrogen, halogen, $C_1$-$C_6$-alkyl, which is unsubstituted or carries one $C_1$-$C_4$alkoxy radical, $C_1$-$C_6$-haloalkyl, $C_1$-$C_6$-alkoxy, $C_1$-$C_4$-haloalkoxy, $C_3$-$C_8$-cycloalkyl, a 5- to 10-membered mono- or bicyclic N-bound saturated heterocycle, which, in addition to the nitrogen atom, may comprise a further heteroatom, selected from O, S and N as ring member and which is unsubstituted or carries 1, 2, 3 or 4 $C_1$-$C_4$-alkyl radicals, a radical $CH_2NR^{1a}R^{1b}$, C-bound 3- to 10-membered, saturated heterocyclyl having 1 or 2 nitrogen atoms and 0 or 1 heteroatoms, selected from O and S, as ring members, aryl, aryl-$CH_2$ aryloxy, hetaryl, hetaryloxy or hetaryl-$CH_2$ wherein the aryl, heterocyclyl and hetaryl rings ring in the last seven radicals themselves are unsubstituted or carry 1, 2, 3, 4 or 5 identical or different radicals $R^{1c}$ provided that $R^2$ is different from hydrogen, if $X^1$ is N or CH, further provided that $R^1$ is different from hydrogen, if $X^2$ is N;

$R^3$ and $R^4$ are independently of each other, selected from hydrogen, halogen, $C_1$-$C_4$-alkyl, $C_1$-$C_4$-haloalkyl, $C_3$-$C_6$-cycloalkyl, $C_1$-$C_4$-alkoxy, $C_1$-$C_4$-alkoxy-$C_1$-$C_4$-alkyl, phenyl, $C_1$-$C_4$-haloalkoxy, a radical $(CH_2)_nNR'R''$, where R' and R" have one of the meanings given for $R^{Z1}$ and $R^{Z2}$ and wherein n is 0, 1, 2, 3 or 4, or C-bound 3- to 7-membered, saturated heterocyclyl having 1 or 2 nitrogen atoms and 0 or 1 heteroatoms, selected from O and S, as ring members, where the heterocyclyl itself is unsubstituted or carries 1, 2, 3, 4 or 5 identical or different radicals $R^{6c}$, where $R^{6c}$ has one of the meanings given for $R^{1c}$;

$R^2$ and $R^3$ can form together with the carbon atoms, to which they are bound, a fused 5- to 6-membered ring, which is itself unsubstituted or carries 1, 2, 3 or 4 identical or different radicals $R^{23a}$;

$R^{23a}$ is selected from the group consisting of halogen, CN, OH, $C_1$-$C_4$-alkyl, $C_3$-$C_6$-cycloalkyl, $C_1$-$C_4$-haloalkyl, $C_1$-$C_4$-alkoxy and $C_1$-$C_4$-haloalkoxy;

$R^5$ is hydrogen, halogen, CN, $C_1$-$C_4$-alkyl, $C_1$-$C_4$-haloalkyl, $C_1$-$C_4$-alkoxy, $C_1$-$C_4$-alkoxy-$C_1$-$C_4$-alkyl, $C_1$-$C_4$-haloalkoxy, $(CH_2)_nNR'R''$, where R' and R" have one of the meanings given for $R^{Z1}$ and $R^{Z2}$ and wherein n is 0, 1, 2, 3 or 4, or C-bound 3- to 7-membered, saturated heterocyclyl having 1 or 2 nitrogen atoms and 0 or 1 heteroatoms, selected from O and S, as ring members, where the heterocyclyl itself is unsubstituted or carries 1, 2, 3, 4 or 5 identical or different radicals $R^{5c}$, where $R^{5c}$ has one of the meanings given for $R^{1c}$;

$R^6$, $R^7$, $R^8$ are, independently of each other, selected from hydrogen, halogen, CN, $C_1$-$C_4$-alkyl, $C_1$-$C_4$-haloalkyl, $C_1$-$C_4$-alkoxy, $C_1$-$C_4$-haloalkyoxy, $C_1$-$C_4$-alkoxy-$C_1$-$C_4$-alkyl, $(CH_2)_nNR'R''$, where R' and R" have one of the meanings given for $R^{Z1}$ and $R^{Z2}$ and wherein n is 0, 1, 2, 3 or 4, or C-bound 3- to 7-membered, saturated heterocyclyl having 1 or 2 nitrogen atoms and 0 or 1 heteroatoms, selected from O and S, as ring members, where the heterocyclyl itself is unsubstituted or carries 1, 2, 3, 4 or 5 identical or different radicals $R^{6c}$, where $R^{6c}$ has one of the meanings given for $R^{1c}$;

$R^a$ is $C_3$-$C_6$-cycloalkyl, $C_1$-$C_6$-haloalkyl or $C_1$-$C_6$-alkyl, which is unsubstituted or carries one radical selected from $C_1$-$C_4$-alkoxy, $C_1$-$C_4$-haloalkoxy and a radical $NR^{a1}R^{a2}$, where $R^{a1}$ and $R^{a2}$ are independently of each other selected from hydrogen, $C_1$-$C_4$-alkyl, $C_3$-$C_6$-cycloalkyl, $C_3$-$C_6$-cycloalkylmethyl and $C_1$-$C_4$-alkoxy-$C_1$-$C_4$-alkyl, a radical $NR^{a3}R^{a4}$ or a radical $N=C(R^{a5})R^{a6}$, where $R^{a3}$ and $R^{a5}$ are independently of each other selected from hydrogen, $C_1$-$C_4$-alkyl, $C_1$-$C_4$haloalkyl, $C_3$-$C_6$-cycloalkyl, $C_3$-$C_6$-cycloalkylmethyl and $C_1$-$C_4$-alkoxy-$C_1$-$C_4$-alkyl;

$R^{a4}$ and $R^{a6}$ are independently of each other selected from hydrogen, $C_1$-$C_4$-alkyl, $C_1$-$C_4$-haloalkyl, $C_3$-$C_6$-cycloalkyl, $C_3$-$C_6$-cycloalkylmethyl, $C_1$-$C_4$-alkoxy-$C_1$-$C_4$-alkyl, C-bound 3- to 7-membered, saturated heterocyclyl, 3- to 7-membered, saturated heterocyclylmethyl, where heterocyclyl in the last two mentioned radicals has 1 or 2 nitrogen atoms and 0 or 1 heteroatoms, selected from O and S, as ring members, aryl, aryl-$CH_2$, hetaryl and hetaryl-$CH_2$, wherein the heterocycicyl, aryl and hetaryl rings ring in the last six radicals themselves are unsubstituted or carry 1, 2, 3, 4 or 5 identical or different radicals $R^{ac}$ where $R^{ac}$ has one of the meanings given for $R^{1c}$;

the pharmaceutically acceptable salts; or N-oxides thereof.

2. The compound of claim 1, wherein $X^2$ is $CR^2$, wherein $R^2$ is phenyl, benzyl or phenoxy, wherein the phenyl ring in the last three radicals itself is unsubstituted or carries 1, 2, 3, 4 or 5 identical or different radicals $R^{1c}$.

3. The compound of claim 1, wherein $X^2$ is $CR^2$, wherein $R^2$ is branched $C_3$-$C_6$-alkyl, $C_1$-$C_6$-haloalkyl or $C_3$-$C_6$-cycloalkyl.

4. The compound of claim 1, wherein $X^2$ is $CR^2$, wherein $R^2$ is a 5-to 10-memebered mono- or bicyclic N-bound saturated heterocycle, which in addition to the nitrogen atom, may comprise a futher heteroatom, selected from O, S and N as ring member and which is unsubstituted or carries 1, 2, 3 or 4 $C_1$-$C_4$-alkyl radicals, or C-bound 3- to 7-membered, saturated heterocyclyl having 1 or 2 nitrogen atoms and 0 or 1 heteroatoms, selected from O and S, as ring members, where the heterocyclyl itself is unsubstituted or carries 1, 2, 3, 4 or 5 identical or different radicals $R^{2c}$.

5. The compound of claim 1, wherein $X^1$ is CH.

6. The compound of claim 1, wherein $X^1$ is N.

7. The compound of claim 1, wherein $X^2$ is CH or N and $X^1$ is $CR^1$, where $R^1$ is different from hydrogen.

8. The compound of claim 1, wherein $R^1$ is branched $C_3$-$C_6$-alkyl, $C_1$-$C_6$-haloalkyl or $C_3$-$C_6$-cycloalkyl.

9. The compound of claim 1, wherein $R^1$ is a radical $NR^{1a}R^{1b}$ or C -bound 3- to 7-membered, saturated heterocyclyl having 1 or 2 nitrogen atoms and 0 or 1 heteroatoms, selected from O and S, as ring members, where the heterocyclyl itself is unsubstituted or carries 1, 2, 3, 4 or 5 identical or different radicals $R^{1c}$.

10. The compound of claim 1, wherein $R^1$ is phenyl, benzyl or phenoxy, wherein the phenyl ring in the last three radicals itself is unsubstituted or carries 1, 2, 3, 4 or 5 identical or different radicals $R^{1c}$.

11. The compound of claim 1, wherein Z is O or NH.

12. The compound of claim 1, wherein $X^3$ is $CR^3$, wherein $R^3$ is hydrogen, chlorine, fluorine, methyl, methoxy or trifluoromethyl.

13. The compound of claim 1, wherein $X^4$ is $CR^4$, wherein $R^4$ is hydrogen, chlorine, fluorine, methyl, methoxy or trifluoromethyl.

14. The compound of claim 1, wherein $Y^1$ is $CR^5$, wherein $R^5$ is hydrogen.

15. The compound of claim 1, wherein $R^a$ is $C_3$-$C_6$-cycloalkyl or $C_2$-$C_6$-alkyl which carries one radical selected from $C_1$-$C_4$-alkoxy, $C_1$-$C_4$-haloalkoxy and a radical $NR^{a1}R^{a2}$, where $R^{a1}$ and $R^{a2}$ are independently selected from hydrogen and $C_1$-$C_4$-alkyl.

16. The compound of claim 1, wherein $R^a$ is a radical $NR^{a3}R^{a4}$, where $R^{a3}$ is selected from hydrogen, $C_1$-$C_4$-alkyl, $C_1$-$C_4$-haloalkyl, $C_3$-$C_6$-cycloalkyl, $C_3$-$C_6$-cycloalkylmethyl and $C_1$-$C_4$-alkoxy-$C_1$-$C_4$-alkyl; and $R^{a4}$ is selected from hydrogen, $C_1$-$C_4$-alkyl, $C_1$-$C_4$-haloalkyl, $C_3$-$C_6$-cycloalkyl, $C_3$-$C_6$-cycloalkylmethyl, $C_1$-$C_4$-alkoxy-$C_1$-$C_4$-alkyl, C-bound 3 to 7 membered, saturated heterocyclyl, 3- to 7-membered, saturated heterocyclylmethyl, where heterocyclyl in the last two mentioned radicals has 1 or 2 nitrogen atoms and 0 or 1 heteroatoms, selected from O and S, as ring members, aryl, aryl-$CH_2$, hetaryl and hetaryl-$CH_2$, wherein the heterocycicyl, aryl and hetaryl rings ring in the last six radicals themselves are unsubstituted or carry 1, 2, 3, 4 or 5 identical or different radicals $R^{ac}$, where $R^{ac}$ has one of the meanings given for $R^{1c}$.

17. The compound of claim 1, wherein Q is $CH_2$.

18. The compound of claim 1, wherein Q is $CH_2CH_2$.

19. The compound of claim 1, wherein the one of $Y^2$, $Y^3$ and $Y^4$, to which Z is bound, is C while the others are CH.

20. The compound of claim 1 of the formula Ia

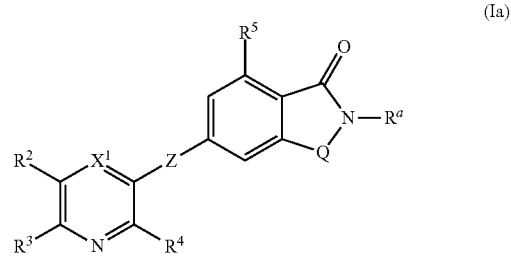

wherein $X^1$, Z, Q, $R^2$, $R^3$, $R^4$, $R^5$ and $R^a$ are as defined above.

21. The compound of claim 1 of the formula Ib

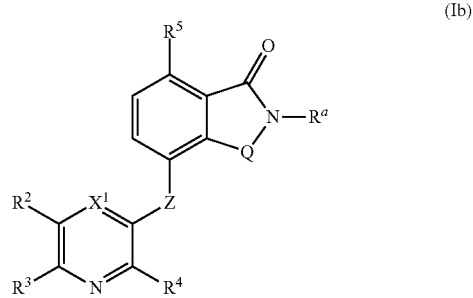

wherein $X^1$, Z, Q, $R^2$, $R^3$, $R^4$, $R^5$ and $R^a$ are as defined above.

22. The compound of claim 1 of the formula Ic

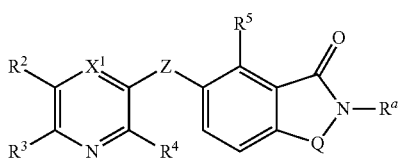

(Ic)

wherein $X^1$, Z, Q, $R^2$, $R^3$, $R^4$, $R^5$ and $R^a$ are as defined above.

23. The compound of claim 20, wherein $X^1$ is CH.
24. The compound of claim 20, wherein Q is $CH_2$.
25. The compound of claim 20, wherein Q is $CH_2CH_2$.
26. A pharmaceutical composition comprising a carrier and a compound of claim 1.
27. The compound of claim 1, selected from the group consisting of:

2-butyl-5-(4-phenylpyridin-3-ylamino)isoindolin-1-one;
2-butyl-5-(5-phenylpyridin-3-ylamino)isoindolin-1-one;
2-butyl-5-(4-phenylpyridin-3-yloxy)isoindolin-1-one;
2-butyl-7-chloro-5-[(5-phenylpyridin-3-yl)amino]-2,3-dihydro-1H-isoindol-1-one;
2-butyl-5-{[5-(piperazin-1-yl)pyridin-3-yl]amino}-2,3-dihydro-1H-isoindo1-1-one;
2-butyl-5-{[2-chloro-5-(piperazin-1-yl)pyridin-3-yl]amino}-2,3-dihydro-1H-isoindo1-1-one;
2-butyl-5-[(5-chloropyridin-3-yl)amino]-2,3-dihydro-1H-isoindol-1-one;
2-butyl-5-{[5-(morpholin-4-yl)pyridin-3-yl]amino}-2,3-dihydro-1H-isoindo1-1-one;
2-butyl-5-{[2-chloro-5-(4-methylpiperazin-1-yl)pyridin-3-yl]amino}-2,3-dihydro-1 H-isoindol-1-one;
2-butyl-5-{[5-(4-methylpiperazin-1-yl)pyridin-3-yl]amino}-2,3-dihydro-1H-isoindo1-1-one;
2-butyl-5-[(5-phenylpyridin-3-yl)oxy]-2,3-dihydro-1H-isoindol-1-one;
2-butyl-4-[(5-phenylpyridin-3-yl)oxy]-2,3-dihydro-1H-isoindol-1-one trifluoroacetate;
2-butyl-5-[(5-phenylpyridin-3-yl)oxy]-3,4-dihydroisoquinolin-1(2H)-one trifluoroacetate;
2-butyl-6-[(5-phenylpyridin-3-yl)oxy]-3,4-dihydroisoquinolin-1(2H)-one trifluoroacetate;
2-butyl-6-[(5-phenylpyridin-3-yl)oxy]-2,3-dihydro-1H-isoindol-1-one trifluoroacetate;
2-butyl-5-(6-phenyl-pyrazin-2-ylamino)-2,3-dihydro-isoindol-1-one;
2-butyl-5-(quinolin-3-ylamino)-2,3-dihydro-1H-isoindo1-1-one;
2-butyl-5-(quinoxalin-2-ylamino)-2,3-dihydro-1H-isoindo1-1-one;
2-(2-methoxyethyl)-5-[(5-phenylpyridin-3-yl)amino]-2,3-dihydro-1H-isoindol-1-one;
2-butyl-5-[(2-chloropyridin-3-yl)amino]-2,3-dihydro-1H-isoindol-1-one;
2-butyl-5-{[2-chloro-5-(piperazin-1-yl)pyridin-3-yl]oxy}-3,4-dihydroisoquinolin-1(2H)-one;
2-butyl-5-{[2-chloro-5-(4-methylpiperazin-1-yl)pyridin-3-yl]oxy}-3,4-dihydroisoquinolin-1(2H)-one; and
2-butyl-5-[(5-phenylpyridin-3-yl)methyl]-2,3-dihydro-1H-isoindol-1-one.

28. A compound that is 2-butyl-5-(5-phenylpyridin-3-yl)-2,3-dihydro-1H-isoindo1-1-one.

29. A method for treating, controlling, ameliorating, or reducing the risk of a medical disorder that responds to influencing by mGlu2 receptor antagonists or agonists, wherein the disorder is selected from the group consisting of anxiety, schizophrenia and epilepsy, the method comprising administering an effective amount of at least one compound of claim 1 to a host in need thereof.

30. The method according to claim 29 wherein the disorder is anxiety.

31. The method according to claim 29 wherein the disorder is schizophrenia.

32. The method according to claim 29 wherein the disorder is epilepsy.

* * * * *